US011149278B2

(12) United States Patent
Thess et al.

(10) Patent No.: US 11,149,278 B2
(45) Date of Patent: Oct. 19, 2021

(54) ARTIFICIAL NUCLEIC ACID MOLECULES FOR IMPROVED PROTEIN EXPRESSION

(71) Applicant: CureVac AG, Tübingen (DE)

(72) Inventors: Andreas Thess, Kusterdingen (DE); Thomas Schlake, Gundelfingen (DE); Stefanie Grund, Stuttgart (DE)

(73) Assignee: CureVac AG, Tübingen (DE)

( * ) Notice: Subject to any disclaimer, the term of this patent is extended or adjusted under 35 U.S.C. 154(b) by 53 days.

(21) Appl. No.: 15/534,496

(22) PCT Filed: Dec. 11, 2015

(86) PCT No.: PCT/EP2015/002501
§ 371 (c)(1),
(2) Date: Jun. 9, 2017

(87) PCT Pub. No.: WO2016/091391
PCT Pub. Date: Jun. 16, 2016

(65) Prior Publication Data
US 2018/0044687 A1 Feb. 15, 2018

(30) Foreign Application Priority Data
Dec. 12, 2014 (WO) ................ PCT/EP2014/003334

(51) Int. Cl.
C12N 15/67 (2006.01)
C12N 15/68 (2006.01)
C12N 15/85 (2006.01)
A61K 39/145 (2006.01)
A61K 39/12 (2006.01)
A61K 39/205 (2006.01)
A61K 48/00 (2006.01)
A61K 39/00 (2006.01)

(52) U.S. Cl.
CPC .............. C12N 15/67 (2013.01); A61K 39/12 (2013.01); A61K 39/145 (2013.01); A61K 39/205 (2013.01); C12N 15/68 (2013.01); C12N 15/85 (2013.01); A61K 48/00 (2013.01); A61K 2039/53 (2013.01); A61K 2039/54 (2013.01); A61K 2039/575 (2013.01); C12N 2760/16134 (2013.01); C12N 2760/16171 (2013.01); C12N 2760/20134 (2013.01); C12N 2760/20171 (2013.01); C12N 2830/50 (2013.01)

(58) Field of Classification Search
None
See application file for complete search history.

(56) References Cited
U.S. PATENT DOCUMENTS

2004/0110295 A1* 6/2004 Punnonen ............ C12N 15/85
435/455
2005/0032730 A1 2/2005 Von der Mulbe et al.
2005/0059624 A1 3/2005 Hoerr et al.
2005/0250723 A1 11/2005 Hoerr et al.
2006/0188490 A1 8/2006 Hoerr et al.
2008/0025944 A1 1/2008 Hoerr et al.
2008/0267873 A1 10/2008 Hoerr et al.
2009/0324584 A1 12/2009 Hoerr et al.
2010/0048883 A1 2/2010 Ketterer et al.
2010/0189729 A1 7/2010 Hoerr et al.
2010/0203076 A1 8/2010 Fotin-Mleczek et al.
2010/0291156 A1 11/2010 Barner et al.
2010/0305196 A1 12/2010 Probst et al.
2011/0053829 A1 3/2011 Baumhof et al.
2011/0250225 A1 10/2011 Fotin-Mleczek et al.
2012/0021043 A1 1/2012 Kramps et al.
2012/0258046 A1 10/2012 Mutzke
2013/0129754 A1 5/2013 Thess et al.
2013/0142818 A1 6/2013 Baumhof et al.
2013/0259879 A1 10/2013 Baumhof et al.
2013/0280283 A1 10/2013 Lorenz et al.
2013/0295043 A1 11/2013 Kallen et al.
2013/0336998 A1 12/2013 Kallen et al.
2014/0147454 A1* 5/2014 Chakraborty .......... A61K 39/00
424/185.1
2015/0037326 A1 2/2015 Butler-Ransohoff et al.
2015/0050302 A1 2/2015 Thess
2015/0057340 A1 2/2015 Thess et al.
2015/0093413 A1 4/2015 Thess et al.
(Continued)

FOREIGN PATENT DOCUMENTS
EP 3167059 5/2017
EP 3594337 1/2020
(Continued)

OTHER PUBLICATIONS

"Homo sapiens RPL36AL mRNA for ribosomal protein L36a-like, complete cds," EMBL, abstract, XP002699423, 2002.

(Continued)

Primary Examiner — Channing S Mahatan
(74) Attorney, Agent, or Firm — Parker Highlander PLLC

(57) ABSTRACT

The invention relates to an artificial nucleic acid molecule comprising an open reading frame and a 3'-UTR comprising at least one poly(A) sequence or a polyadenylation signal. The invention further relates to a vector comprising the artificial nucleic acid molecule comprising an open reading frame and a 3'-UTR comprising at least one poly(A) sequence or a polyadenylation signal, to a cell comprising the artificial nucleic acid molecule or the vector, to a pharmaceutical composition comprising the artificial nucleic acid molecule or the vector and to a kit comprising the artificial nucleic acid molecule, the vector and/or the pharmaceutical composition. The invention also relates to a method for increasing protein production from an artificial nucleic acid molecule and to the use of a 3'-UTR for a method for increasing protein production from an artificial nucleic acid molecule. Moreover, the invention concerns the use of the artificial nucleic acid molecule, the vector, the kit or the pharmaceutical composition as a medicament, as a vaccine or in gene therapy.

20 Claims, 10 Drawing Sheets
Specification includes a Sequence Listing.

(56) References Cited

U.S. PATENT DOCUMENTS

| | | |
|---|---|---|
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |

FOREIGN PATENT DOCUMENTS

| | | |
|---|---|---|
| WO | WO 2016-107877 | 7/1916 |
| WO | WO 2016-165825 | 10/1916 |
| WO | WO 2016-165831 | 10/1916 |
| WO | WO 2016-184576 | 11/1916 |
| WO | WO 2016-184822 | 11/1916 |
| WO | WO 2016474227 | 11/1916 |
| WO | WO 2016474271 | 11/1916 |
| WO | WO 2016484575 | 11/1916 |
| WO | WO 2016-203025 | 12/1916 |
| WO | WO 2016493206 | 12/1916 |
| WO | WO 2016493226 | 12/1916 |
| WO | WO 2017-001058 | 1/1917 |
| WO | WO 2017-009376 | 1/1917 |
| WO | WO 2017-021546 | 2/1917 |
| WO | WO 2017-025120 | 2/1917 |
| WO | WO 2017-025447 | 2/1917 |
| WO | WO 2017-036580 | 3/1917 |
| WO | WO 2001-007590 | 2/2001 |
| WO | WO 2002-098443 | 12/2002 |
| WO | WO 2005-075644 | 8/2005 |
| WO | WO 2007-036366 | 4/2007 |
| WO | WO 2007-068265 | 6/2007 |
| WO | WO 2008-112127 | 9/2008 |
| WO | WO 2013-120629 | 2/2013 |
| WO | 2013/143698 A1 † | 10/2013 |
| WO | 2013/143700 A2 † | 10/2013 |
| WO | WO 2013-143698 | 10/2013 |
| WO | WO 2013-143699 | 10/2013 |
| WO | WO 2013443700 | 10/2013 |
| WO | WO 2015-101415 | 7/2015 |
| WO | WO 2016-005004 | 1/2016 |
| WO | WO 2016-005324 | 1/2016 |

OTHER PUBLICATIONS

International Preliminary Report on Patentability issued in corresponding PCT Application No. PCT/EP2015/002501, dated Jun. 13, 2017.

International Search Report and Written Opinion issued in corresponding PCT Application No. PCT/EP2015/002501, dated Mar. 5, 2016.

Ledda et al., "Effect of 3'UTR length on the translational regulation of 5'-terminal oligopyrimidine mRNAs," *Gene*, 344:213-220, 2005.

Sahin et al., "mRNA-based therapeutics—developing a new class of drugs," *Nat Rev Drug Discov.*, 13(10):759-780, 2014.

Holtkamp et al. "Modification of antigen-encoding RNA increases stability, translational efficacy, and T-cell stimulatory capacity of dendritic cells," *Blood*, 108(13):4009-4017, 2006.

\* cited by examiner
† cited by third party

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAAAAATGCATCCCC
CCCCCCCCCCCCCCCCCCCCCCCCCAAAGGCTCTTTTCAGAGCCACCAGAATT

Figure 1

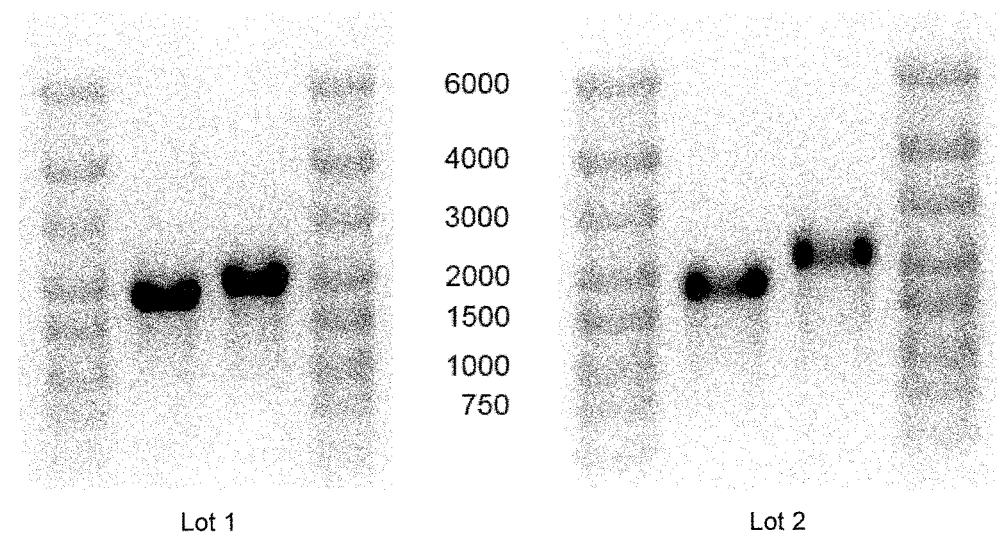
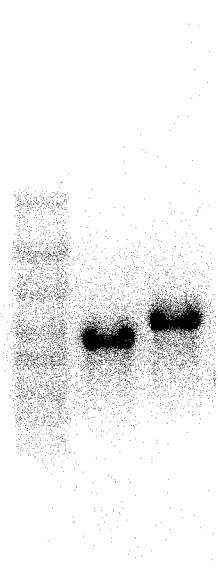
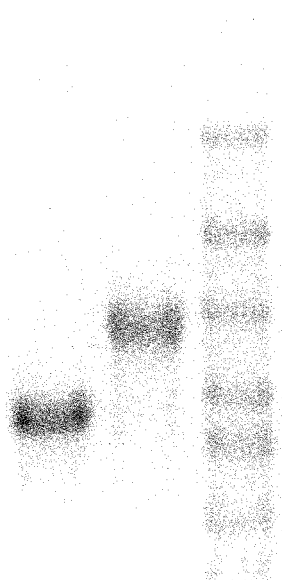
Figure 2

32L4-H1N1(Netherlands2009)-HA(GC)-albumin7- A64-N5-C30-histoneSL

```
GGGGCGCTGCCTACGGAGGTGGCAGCCATCTCCTTCTCGGCATCAAGCTTACCATGAAGGCCATCCTG
GTGGTCCTCCTGTACACCTTCGCCACCGCGAACGCCGACACGCTGTGCATCGGCTACCACGCCAACAA
CAGCACCGACACCGTGGACACCGTGCTCGAGAAGAACGTCACGGTGACCCACTCCGTGAACCTGCTGG
AGGACAAGCACAACGGGAAGCTCTGCAAGCTGCGGGGCGTCGCCCCGCTGCACCTCGGGAAGTGCAAC
ATCGCCGGCTGGATCCTGGGGAACCCGGAGTGCGAGAGCCTGTCCACCGCGAGCTCCTGGAGCTACAT
CGTGGAGACCTCCAGCTCCGACAACGGCACGTGCTACCCCGGCGACTTCATCGACTACGAGGAGCTCC
GCGAGCAGCTGAGCTCCGTGAGCTCCTTCGAGCGGTTCGAGATCTTCCCCAAGACCAGCTCCTGGCCC
AACCACGACAGCAACAAGGGGGTCACCGCCGCCTGCCCGCACGCCGGCGCGAAGTCCTTCTACAAGAA
CCTGATCTGGCTCGTGAAGAAGGGGAACAGCTACCCCAAGCTGTCCAAGAGCTACATCAACGACAAGG
GCAAGGAGGTGCTGGTCCTCTGGGGGATCCACCACCCCAGCACCTCCGCCGACCAGCAGAGCCTGTAC
CAGAACGCCGACGCCTACGTGTTCGTGGGCTCCAGCCGCTACTCCAAGAAGTTCAAGCCCGAGATCGC
CATCCGGCCGAAGGTCCGCGACCAGGAGGGCCGGATGAACTACTACTGGACGCTGGTGGAGCCCGGGG
ACAAGATCACCTTCGAGGCGACCGGCAACCTCGTGGTCCCCCGCTACGCCTTCGCCATGGAGCGGAAC
GCCGGGAGCGGCATCATCATCTCCGACACCCCCGTGCACGACTGCAACACGACCTGCCAGACCCCGAA
GGGCGCCATCAACACCAGCCTGCCCTTCCAGAACATCCACCCCATCACGATCGGGAAGTGCCCCAAGT
ACGTGAAGTCCACCAAGCTGCGCCTCGCGACCGGCCTGCGGAACGTCCCGAGCATCCAGTCCCGCGGG
CTGTTCGGCGCCATCGCCGGGTTCATCGAGGGCGGCTGGACCGGGATGGTGGACGGCTGGTACGGGTA
CCACCACCAGAACGAGCAGGGCAGCGGGTACGCCGCCGACCTCAAGTCCACGCAGAACGCGATCGACG
AGATCACCAACAAGGTGAACAGCGTCATCGAGAAGATGAACACCCAGTTCACCGCCGTGGGCAAGGAG
TTCAACCACCTGGAGAAGCGGATCGAGAACCTGAACAAGAAGGTCGACGACGGCTTCCTCGACATCTG
GACGTACAACGCCGAGCTGCTGGTGCTCCTGGAGAACGAGCGCACCCTGGACTACCACGACTCCAACG
TGAAGAACCTCTACGAGAAGGTCCGGAGCCAGCTGAAGAACAACGCCAAGGAGATCGGGAACGGCTGC
TTCGAGTTCTACCACAAGTGCGACAACACCTGCATGGAGTCCGTGAAGAACGGGACCTACGACTACCC
CAAGTACAGCGAGGAGGCCAAGCTGAACCGCGAGGAGATCGACGGCGTGAAGCTCGAGTCCACGCGGA
TCTACCAGATCCTGGCGATCTACAGCACCGTCGCCAGCTCCCTGGTGCTCGTGGTCAGCCTGGGGGCC
ATCTCCTTCTGGATGTGCAGCAACGGCTCCCTGCAGTGCCGCATCTGCATCTGACCACTAGTGCATCA
CATTTAAAAGCATCTCAGCCTACCATGAGAATAAGAGAAAGAAAATGAAGATCAATAGCTTATTCATC
TCTTTTTCTTTTTCGTTGGTGTAAAGCCAACACCCTGTCTAAAAAACATAAATTTCTTTAATCATTTT
GCCTCTTTTCTCTGTGCTTCAATTAATAAAAATGGAAAGAACCTAGATCTAAAAAAAAAAAAAAAAAA
AAAAAAAAAAAAAAAAAAAAAAAAAAAAAAAAAAAAAAAAAAAAAAATGCATCCCCCCCCCCCCCCC
CCCCCCCCCCCCCCAAAGGCTCTTTTCAGAGCCACCAGAATT
```

Figure 8

32L4-RAV-G(GC)-albumin7-A64-N5-C30-histoneSL

```
GGGGCGCTGCCTACGGAGGTGGCAGCCATCTCCTTCTCGGCATCAAGCTTACCATGGTGCCCCAGGCC
CTGCTCTTCGTCCCGCTGCTGGTGTTCCCCCTCTGCTTCGGCAAGTTCCCCATCTACACCATCCCCGA
CAAGCTGGGGCCGTGGAGCCCCATCGACATCCACCACCTGTCCTGCCCCAACAACCTCGTGGTCGAGG
ACGAGGGCTGCACCAACCTGAGCGGGTTCTCCTACATGGAGCTGAAGGTGGGCTACATCAGCGCCATC
AAGATGAACGGGTTCACGTGCACCGGCGTGGTCACCGAGGCGGAGACCTACACGAACTTCGTGGGCTA
CGTGACCACCACCTTCAAGCGGAAGCACTTCCGCCCCACGCCGGACGCCTGCCGGGCCGCCTACAACT
GGAAGATGGCCGGGGACCCCCGCTACGAGGAGTCCCTCCACAACCCCTACCCCGACTACCACTGGCTG
CGGACCGTCAAGACCACCAAGGAGAGCCTGGTGATCATCTCCCGAGCGTGGCGGACCTCGACCCCTA
CGACCGCTCCCTGCACAGCGGGTCTTCCCCGGCGGGAACTGCTCCGGCGTGGCCGTGAGCTCCACGT
ACTGCAGCACCAACCACGACTACACCATCTGGATGCCCGAGAACCCGCGCCTGGGGATGTCCTGCGAC
ATCTTCACCAACAGCCGGGGCAAGCGCGCCTCCAAGGGCAGCGAGACGTGCGGGTTCGTCGACGAGCG
GGGCCTCTACAAGTCCCTGAAGGGGGCCTGCAAGCTGAAGCTCTGCGGCGTGCTGGGCCTGCGCCTCA
TGGACGGGACCTGGGTGGCGATGCAGACCAGCAACGAGACCAAGTGGTGCCCCCCCGGCCAGCTGGTC
AACCTGCACGACTTCCGGAGCGACGAGATCGAGCACCTCGTGGTGGAGGAGCTGGTCAAGAAGCGCGA
GGAGTGCCTGGACGCCCTCGAGTCCATCATGACGACCAAGAGCGTGTCCTTCCGGCGCCTGAGCCACC
TGCGGAAGCTCGTGCCCGGGTTCGGCAAGGCCTACACCATCTTCAACAAGACCCTGATGGAGGCCGAC
GCCCACTACAAGTCCGTCCGACGTGGAACGAGATCATCCCGAGCAAGGGGTGCCTGCGGGTGGGCGG
CCGCTGCCACCCCACGTCAACGGGGTGTTCTTCAACGGCATCATCCTCGGGCCCGACGGCAACGTGC
TGATCCCCGAGATGCAGTCCAGCCTGCTCCAGCAGCACATGGAGCTGCTGGTCTCCAGCGTGATCCCG
CTCATGCACCCCCTGGCGGACCCCTCCACCGTGTTCAAGAACGGGGACGAGGCCGAGGACTTCGTCGA
GGTGCACCTGCCCGACGTGCACGAGCGGATCAGCGGCGTCGACCTCGGCCTGCCGAACTGGGGGAAGT
ACGTGCTGCTCTCCGCCGGCGCCCTGACCGCCCTGATGCTGATCATCTTCCTCATGACCTGCTGGCGC
CGGGTGAACCGGAGCGAGCCCACGCAGCACAACCTGCGCGGGACCGGCCGGGAGGTCTCCGTGACCCC
GCAGAGCGGGAAGATCATCTCCAGCTGGGAGTCCTACAAGAGCGGCGGCGAGACCGGGCTGTGAGGAC
TAGTGCATCACATTTAAAAGCATCTCAGCCTACCATGAGAATAAGAGAAAGAAAATGAAGATCAATAG
CTTATTCATCTCTTTTTCTTTTTCGTTGGTGTAAAGCCAACACCCTGTCTAAAAAACATAAATTTCTT
TAATCATTTTGCCTCTTTTCTCTGTGCTTCAATTAATAAAAAATGGAAAGAACCTAGATCTAAAAAAA
AAAAAAAAAAAAAAAAAAAAAAAAAAAAAAAAAAAAAAAAAAAAAAAAAAAAAAAATGCATCCCCCC
CCCCCCCCCCCCCCCCCCCCCCCAAAGGCTCTTTTCAGAGCCACCAGAATT
```

Figure 10

SEQUENCE LISTING

```
<160> NUMBER OF SEQ ID NOS: 15

<210> SEQ ID NO 1
<211> LENGTH: 140
<212> TYPE: DNA
<213> ORGANISM: Artificial Sequence
<220> FEATURE:
<223> OTHER INFORMATION: Exemplary DNA sequence comprising a poly(A)
      sequence

<400> SEQUENCE: 1
gtccacctgt ccctcctggg ctgctggatt gtctcgtttt cctgccaaat aaacaggatc      60
agcgctttac agatctaaaa aaaaaaaaaa aaaaaaaaaa aaaaaaaaaa aaaaaaaaaa     120
aaaaaaaaaa aaaaaaaaaa                                                 140

<210> SEQ ID NO 2
<211> LENGTH: 140
<212> TYPE: RNA
<213> ORGANISM: Artificial Sequence
<220> FEATURE:
<223> OTHER INFORMATION: Exemplary RNA sequence comprising a poly(A)
      sequence

<400> SEQUENCE: 2
guccaccugu cccuccuggg cugcuggauu gucucguuuu ccugccaaau aaacaggauc      60
agcgcuuuac agaucuaaaa aaaaaaaaaa aaaaaaaaaa aaaaaaaaaa aaaaaaaaaa     120
aaaaaaaaaa aaaaaaaaaa                                                 140
```

<210> SEQ ID NO 3
<211> LENGTH: 186
<212> TYPE: DNA
<213> ORGANISM: Homo sapiens

<400> SEQUENCE: 3

| | | | |
|---|---|---|---|
| catcacattt aaaagcatct cagcctacca tgagaataag agaaagaaaa tgaagatcaa | | | 60 |
| aagcttattc atctgttttt cttttcgtt ggtgtaaagc caacccctg tctaaaaaac | | | 120 |
| ataaatttct ttaatcattt tgcctctttt ctctgtgctt caattaataa aaaatggaaa | | | 180 |
| gaatct | | | 186 |

<210> SEQ ID NO 4
<211> LENGTH: 186
<212> TYPE: DNA
<213> ORGANISM: Homo sapiens

<400> SEQUENCE: 4
catcacattt aaaagcatct cagcctacca tgagaataag agaaagaaaa tgaagatcaa    60
tagcttattc atctctttt cttttcgtt ggtgtaaagc caacccctg tctaaaaaac    120
ataaatttct ttaatcattt tgcctctttt ctctgtgctt caattaataa aaaatggaaa    180
gaacct    186

<210> SEQ ID NO 5
<211> LENGTH: 110
<212> TYPE: DNA
<213> ORGANISM: Homo sapiens

<400> SEQUENCE: 5
gctggagcct cggtggccat gcttcttgcc ccttgggcct ccccccagcc cctcctcccc    60
ttcctgcacc cgtacccccg tggtctttga ataaagtctg agtgggcggc    110

<210> SEQ ID NO 6
<211> LENGTH: 108
<212> TYPE: DNA
<213> ORGANISM: Homo sapiens

<400> SEQUENCE: 6
gctggagcct cggtagccgt tcctcctgcc cgctgggcct cccaacgggc cctcctcccc    60
tccttgcacc ggcccttcct ggtctttgaa taaagtctga gtgggcag    108

<210> SEQ ID NO 7
<211> LENGTH: 132
<212> TYPE: DNA
<213> ORGANISM: Homo sapiens

<400> SEQUENCE: 7
gctcgctttc ttgctgtcca atttctatta aaggttcctt tgttccctaa gtccaactac    60
taaactgggg gatattatga agggccttga gcatctggat tctgcctaat aaaaaacatt    120
tattttcatt gc    132

<210> SEQ ID NO 8
<211> LENGTH: 44
<212> TYPE: DNA
<213> ORGANISM: Homo sapiens

<400> SEQUENCE: 8

```
gcccgatggg cctcccaacg ggccctcctc ccctccttgc accg                    44
```

<210> SEQ ID NO 9
<211> LENGTH: 70
<212> TYPE: DNA
<213> ORGANISM: Artificial Sequence
<220> FEATURE:
<223> OTHER INFORMATION: 3'-UTR sequence of ribosomal protein Small 9
      (RPS9)

<400> SEQUENCE: 9

```
gtccacctgt ccctcctggg ctgctggatt gtctcgtttt cctgccaaat aaacaggatc   60
agcgctttac                                                          70
```

<210> SEQ ID NO 10
<211> LENGTH: 70
<212> TYPE: RNA
<213> ORGANISM: Artificial Sequence
<220> FEATURE:
<223> OTHER INFORMATION: 3'-UTR sequence of ribosomal protein Small 9
      (RPS9)

<400> SEQUENCE: 10

```
guccaccugu cccuccuggg cugcuggauu gucucguuuu ccugccaaau aaacaggauc   60
agcgcuuuac                                                          70
```

<210> SEQ ID NO 11
<211> LENGTH: 24
<212> TYPE: DNA
<213> ORGANISM: Artificial Sequence
<220> FEATURE:
<223> OTHER INFORMATION: histone stem-loop sequence

<400> SEQUENCE: 11

```
caaaggctct tttcagagcc acca                                          24
```

<210> SEQ ID NO 12
<211> LENGTH: 42
<212> TYPE: DNA
<213> ORGANISM: Artificial Sequence
<220> FEATURE:
<223> OTHER INFORMATION: 5'-UTR of human ribosomal protein Large 32
      lacking the 5' terminal oligopyrimidine tract

<400> SEQUENCE: 12

```
ggcgctgcct acggaggtgg cagccatctc cttctcggca tc                      42
```

<210> SEQ ID NO 13
<211> LENGTH: 2035
<212> TYPE: DNA
<213> ORGANISM: Artificial Sequence
<220> FEATURE:
<223> OTHER INFORMATION: rpl32 - PpLuc(GC) - albumin7 - A64 - C30 -
      histone stem-loop

<400> SEQUENCE: 13

```
ggggcgctgc ctacggaggt ggcagccatc tccttctcgg catcaagctt gaggatggag   60
gacgccaaga acatcaagaa gggcccggcg cccttctacc cgctggagga cgggaccgcc   120
ggcgagcagc tccacaaggc catgaagcgg tacgccctgg tgccgggcac gatcgccttc   180
accgacgccc acatcgaggt cgacatcacc tacgcggagt acttcgagat gagcgtgcgc   240
ctggccgagg ccatgaagcg gtacggcctg aacaccaacc accggatcgt ggtgtgctcg   300
gagaacagcc tgcagttctt catgccggtg ctgggcgccc tcttcatcgg cgtggccgtc   360
```

```
gccccggcga acgacatcta caacgagcgg gagctgctga acagcatggg gatcagccag    420
ccgaccgtgg tgttcgtgag caagaagggc ctgcagaaga tcctgaacgt gcagaagaag    480
ctgcccatca tccagaagat catcatcatg gacagcaaga ccgactacca gggcttccag    540
tcgatgtaca cgttcgtgac cagccacctc ccgccgggct tcaacgagta cgacttcgtc    600
ccggagagct tcgaccggga caagaccatc gccctgatca tgaacagcag cggcagcacc    660
ggcctgccga gggggtggc cctgccgcac cggaccgcct gcgtgcgctt ctcgcacgcc    720
cgggacccca tcttcggcaa ccagatcatc ccggacaccg ccatcctgag cgtggtgccg    780
ttccaccacg gcttcggcat gttcacgacc ctgggctacc tcatctgcgg cttccgggtg    840
gtcctgatgt accggttcga ggaggagctg ttcctgcgga gcctgcagga ctacaagatc    900
cagagcgcgc tgctcgtgcc gaccctgttc agcttcttcg ccaagagcac cctgatcgac    960
aagtacgacc tgtcgaacct gcacgagatc gccagcgggg gcgccccgct gagcaaggag   1020
gtgggcgagg ccgtggccaa gcggttccac ctcccgggca tccgccaggg ctacggcctg   1080
accgagacca cgagcgcgat cctgatcacc cccgaggggg acgacaagcc gggcgccgtg   1140
ggcaaggtgg tcccgttctt cgaggccaag gtggtggacc tggacaccgg caagaccctg   1200
ggcgtgaacc agcggggcga gctgtgcgtg cggggggccga tgatcatgag cggctacgtg   1260
aacaacccgg aggccaccaa cgccctcatc gacaaggacg gctggctgca cagcggcgac   1320
atcgcctact gggacgagga cgagcacttc ttcatcgtcg accggctgaa gtcgctgatc   1380
aagtacaagg ctaccaggt ggcgccggcc gagctggaga gcatcctgct ccagcacccc   1440
aacatcttcg acgccggcgt ggccgggctg ccggacgacg acgccggcga gctgccggcc   1500
gcggtggtgg tgctggagca cggcaagacc atgacggaga aggagatcgt cgactacgtg   1560
gccagccagg tgaccaccgc caagaagctg cggggcggcg tggtgttcgt ggacgaggtc   1620
ccgaagggcc tgaccgggaa gctcgacgcc cggaagatcc gcgagatcct gatcaaggcc   1680
aagaagggcg gcaagatcgc cgtgtaagac tagtgcatca catttaaaag catctcagcc   1740
taccatgaga ataagagaaa gaaaatgaag atcaatagct tattcatctc ttttctcttt   1800
tcgttggtgt aaagccaaca ccctgtctaa aaaacataaa tttctttaat cattttgcct   1860
cttttctctg tgcttcaatt aataaaaaat ggaaagaacc tagatctaaa aaaaaaaaa   1920 aaaaaaaaaa aaaaaaaaaa aaaaaaaaaa aaaaaaaaa aaaaaaaaa atgcatcccc   1980 cccccccccc cccccccccc cccccccaaa ggctcttttc agagccacca gaatt        2035
```

<210> SEQ ID NO 14
<211> LENGTH: 2083
<212> TYPE: DNA
<213> ORGANISM: Artificial Sequence
<220> FEATURE:
<223> OTHER INFORMATION: 32L4-H1N1(Netherlands2009)-HA(GC)-albumin7-
A64-N5-C30-histoneSL

<400> SEQUENCE: 14

```
ggggcgctgc ctacggaggt ggcagccatc tccttctcgg catcaagctt accatgaagg     60
ccatcctggt ggtcctcctg tacaccttcg ccaccgcgaa cgccgacacg ctgtgcatcg    120
gctaccacgc caacaacagc accgacaccg tggacaccgt gctcgagaag aacgtcacgg    180
tgacccactc cgtgaacctg ctggaggaca agcacaacgg gaagctctgc aagctgcggg    240
gcgtcgcccc gctgcacctc gggaagtgca acatcgccgg ctggatcctg gggaacccgg    300
agtgcgagag cctgtccacc gcgagctcct ggagctacat cgtggagacc tccagctccg    360
```

```
acaacggcac gtgctacccc ggcgacttca tcgactacga ggagctccgc gagcagctga      420
gctccgtgag ctccttcgag cggttcgaga tcttccccaa gaccagctcc tggcccaacc      480
acgacagcaa caaggggtc accgccgcct gcccgcacgc cggcgcgaag tccttctaca       540
agaacctgat ctggctcgtg aagaagggga acagctaccc caagctgtcc aagagctaca     600
tcaacgacaa gggcaaggag gtgctggtcc tctgggggat ccaccacccc agcacctccg     660
ccgaccagca gagcctgtac cagaacgccg acgcctacgt gttcgtgggc tccagccgct     720
actccaagaa gttcaagccc gagatcgcca tccggccgaa ggtccgcgac caggagggcc     780
ggatgaacta ctactggacg ctggtggagc cggggacaa gatcaccttc gaggcgaccg      840
gcaacctcgt ggtccccgc tacgccttcg ccatggagcg gaacgccggg agcggcatca      900
tcatctccga caccccgtg cacgactgca acacgacctg ccagaccccg aagggcgcca     960
tcaacaccag cctgcccttc agaacatcc accccatcac gatcgggaag tgccccaagt     1020
acgtgaagtc caccaagctg cgcctcgcga ccggcctgcg gaacgtcccg agcatccagt     1080
cccgcgggct gttcggcgcc atcgccgggt tcatcgaggg cggctggacc gggatggtgg     1140
acggctggta cgggtaccac caccagaacg agcagggcag cgggtacgcc gccgacctca     1200
agtccacgca gaacgcgatc gacgagatca ccaacaaggt gaacagcgtc atcgagaaga     1260
tgaacaccca gttcaccgcc gtgggcaagg agttcaacca cctggagaag cggatcgaga     1320
acctgaacaa gaaggtcgac gacggcttcc tcgacatctg gacgtacaac gccgagctgc     1380
tggtgctcct ggagaacgag cgcacccctgg actaccacga ctccaacgtg aagaaccttct    1440 acgagaaggt ccggagccag ctgaagaaca cgccaagga gatcgggaac ggctgcttcg     1500
agttctacca caagtgcgac aacacctgca tggagtccgt gaagaacggg acctacgact     1560
accccaagta cagcgaggag gccaagctga accgcgagga gatcgacggc gtgaagctcg     1620
agtccacgcg gatctaccag atcctggcga tctacagcac cgtcgccagc tccctggtgc     1680
tcgtggtcag cctgggggcc atctccttct ggatgtgcag caacggctcc ctgcagtgcc     1740
gcatctgcat ctgaccacta gtgcatcaca tttaaaagca tctcagccta ccatgagaat     1800
aagagaaaga aaatgaagat caatagctta ttcatctctt tttctttttc gttggtgtaa     1860
agccaacacc ctgtctaaaa aacataaatt tctttaatca ttttgcctct tttctctgtg     1920
cttcaattaa taaaaatgg aaagaaccta gatcaaaaa aaaaaaaaaa aaaaaaaaa       1980 aaaaaaaaaaa aaaaaaaaaa aaaaaaaaaa aaaaaaaat gcatcccccc ccccccccc    2040 cccccccccc ccccaaagg ctctttttcag agccaccaga att                            2083
```

<210> SEQ ID NO 15
<211> LENGTH: 1957
<212> TYPE: DNA
<213> ORGANISM: Artificial Sequence
<220> FEATURE:
<223> OTHER INFORMATION: 32L4-RAV-G(GC)-albumin7-A64-N5-C30-histoneSL

<400> SEQUENCE: 15

```
ggggcgctgc ctacggaggt ggcagccatc tccttctcgg catcaagctt accatggtgc        60
cccaggccct gctcttcgtc ccgctgctgg tgttccccct ctgcttcggc aagttccccca    120 tctacaccat ccccgacaag ctggggccgt ggagccccat cgacatccac cacctgtcct     180
gccccaacaa cctcgtggtc gaggacgagg gctgcaccaa cctgagcggg ttctcctaca    240
tggagctgaa ggtgggctac atcagcgcca tcaagatgaa cgggttcacg tgcaccggcg    300
```

```
tggtcaccga ggcggagacc tacacgaact tcgtgggcta cgtgaccacc accttcaagc    360
ggaagcactt ccgccccacg ccggacgcct gccgggccgc ctacaactgg aagatggccg    420
gggaccccg ctacgaggag tccctccaca acccctaccc cgactaccac tggctgcgga     480
ccgtcaagac caccaaggag agcctggtga tcatctcccc gagcgtggcg gacctcgacc    540
cctacgaccg ctccctgcac agccgggtct tccccggcgg gaactgctcc ggcgtggccg    600
tgagctccac gtactgcagc accaaccacg actacaccat ctggatgccc gagaacccgc    660
gcctggggat gtcctgcgac atcttcacca acagccgggg caagcgcgcc tccaagggca    720
gcgagacgtg cgggttcgtc gacgagcggg gcctctacaa gtccctgaag ggggcctgca    780
agctgaagct ctgcggcgtg ctgggcctgc gcctcatgga cgggacctgg gtggcgatgc    840
agaccagcaa cgagaccaag tggtgccccc ccggccagct ggtcaacctg cacgacttcc    900
ggagcgacga gatcgagcac ctcgtggtgg aggagctggt caagaagcgc gaggagtgcc    960
tggacgccct cgagtccatc atgacgacca agagcgtgtc cttccggcgc ctgagccacc   1020
tgcggaagct cgtgcccggg ttcggcaagg cctacaccat cttcaacaag accctgatgg   1080
aggccgacgc ccactacaag tccgtccgca cgtggaacga gatcatcccg agcaaggggt   1140
gcctgcgggt gggcggccgc tgccaccccc acgtcaacgg ggtgttcttc aacggcatca   1200
tcctcgggcc cgacggcaac gtgctgatcc ccgagatgca gtccagcctg ctccagcagc   1260
acatggagct gctggtctcc agcgtgatcc cgctcatgca ccccctggcg gacccctcca   1320
ccgtgttcaa gaacggggac gaggccgagg acttcgtcga ggtgcacctg cccgacgtgc   1380
acgagcggat cagcggcgtc gacctcggcc tgccgaactg ggggaagtac gtgctgctct   1440
ccgccggcgc cctgaccgcc ctgatgctga tcatcttcct catgacctgc tggcgccggg   1500
tgaaccggag cgagcccacg cagcacaacc tgcgcgggac cggccgggag gtctccgtga   1560
ccccgcagag cgggaagatc atctccagct gggagtccta caagagcggc ggcgagaccg   1620
ggctgtgagg actagtgcat cacatttaaa agcatctcag cctaccatga gaataagaga   1680
aagaaaatga agatcaatag cttattcatc tcttttttctt tttcgttggt gtaaagccaa   1740
caccctgtct aaaaaacata aatttcttta atcattttgc ctctttttctc tgtgcttcaa   1800
ttaataaaaa atggaaagaa cctagatcta aaaaaaaaaa aaaaaaaaaa aaaaaaaaaa   1860
aaaaaaaaaa aaaaaaaaaa aaaaaaaaaa aaatgcatcc ccccccccccc ccccccccc   1920
cccccccca aaggctcttt tcagagccac cagaatt                              1957
```

ARTIFICIAL NUCLEIC ACID MOLECULES FOR IMPROVED PROTEIN EXPRESSION

This invention was made with Government support under Agreement No. HR0011-11-3-0001 awarded by DARPA. The Government has certain rights in the invention.

This application is a national phase application under 35 U.S.C. § 371 of International Application No. PCT/EP2015/002501, filed Dec. 11, 2015, which claims the benefit of international patent application PCT/EP2014/003334, filed Dec. 12, 2014, each of which is incorporated herein by reference in its entirety.

FIELD OF THE INVENTION

The invention relates to an artificial nucleic acid molecule comprising an open reading frame and a 3'-UTR comprising at least one poly(A) sequence or a polyadenylation signal. The invention further relates to a vector comprising the artificial nucleic acid molecule comprising an open reading frame and a 3'-UTR comprising at least one poly(A) sequence or a polyadenylation signal, to a cell comprising the artificial nucleic acid molecule or the vector, to a pharmaceutical composition comprising the artificial nucleic acid molecule or the vector and to a kit comprising the artificial nucleic acid molecule, the vector and/or the pharmaceutical composition. The invention also relates to a method for increasing protein production from an artificial nucleic acid molecule and to the use of a 3'-UTR for a method for increasing protein production from an artificial nucleic acid molecule. Moreover, the invention concerns the use of the artificial nucleic acid molecule, the vector, the kit or the pharmaceutical composition as a medicament, as a vaccine or in gene therapy.

BACKGROUND OF THE INVENTION

Gene therapy and genetic vaccination belong to the most promising and quickly developing methods of modern medicine. They may provide highly specific and individual options for therapy of a large variety of diseases. Particularly, inherited genetic diseases but also autoimmune diseases, cancerous or tumour-related diseases as well as inflammatory diseases may be the subject of such treatment approaches. Also, it is envisaged to prevent (early) onset of such diseases by these approaches.

The main conceptual rational behind gene therapy is appropriate modulation of impaired gene expression associated with pathological conditions of specific diseases. Pathologically altered gene expression may result in lack or overproduction of essential gene products, for example, signalling factors such as hormones, housekeeping factors, metabolic enzymes, structural proteins or the like. Altered gene expression may not only be due to mis-regulation of transcription and/or translation, but also due to mutations within the ORF coding for a particular protein. Pathological mutations may be caused by e.g. chromosomal aberration, or by more specific mutations, such as point or frame-shift-mutations, all of them resulting in limited functionality and, potentially, total loss of function of the gene product. However, misregulation of transcription or translation may also occur, if mutations affect genes encoding proteins, which are involved in the transcriptional or translational machinery of the cell. Such mutations may lead to pathological up- or down-regulation of genes, which are—as such—functional. Genes encoding gene products which exert such regulating functions, may be, e.g., transcription factors, signal receptors, messenger proteins or the like. However, loss of function of such genes encoding regulatory proteins may, under certain circumstances, be reversed by artificial introduction of other factors acting further downstream of the impaired gene product. Such gene defects may also be compensated by gene therapy via substitution of the affected gene itself.

Genetic vaccination allows to evoke a desired immune response to selected antigens, such as characteristic components of bacterial surfaces, viral particles, tumour antigens or the like. Generally, vaccination is one of the pivotal achievements of modern medicine. However, effective vaccines are currently available only for a smaller number of diseases. Accordingly, infections that are not preventable by vaccination still affect millions of people every year.

Commonly, vaccines may be subdivided into "first", "second" and "third" generation vaccines. "First generation" vaccines are, typically, whole-organism vaccines. They are based on either live and attenuated or killed pathogens, e.g. viruses, bacteria or the like. The major drawback of live and attenuated vaccines is the risk for a reversion to life-threatening variants. Thus, although attenuated, such pathogens may still intrinsically bear unpredictable risks. Killed pathogens may not be as effective as desired for generating a specific immune response. In order to minimize these risks, "second generation" vaccines were developed. These are, typically, subunit vaccines, consisting of defined antigens or recombinant protein components, which are derived from pathogens.

Genetic vaccines, i.e. vaccines for genetic vaccination, are usually understood as "third generation" vaccines. They are typically composed of genetically engineered nucleic acid molecules, which allow expression of peptide or protein (antigen) fragments characteristic for a pathogen or a tumor antigen in vivo. Genetic vaccines are expressed upon administration to a patient and uptake by competent cells. Expression of the administered nucleic acids results in production of the encoded proteins. In the event these proteins are recognized as foreign by the patient's immune system, an immune response is triggered.

As can be seen from the above, both methods, gene therapy and genetic vaccination, are essentially based on the administration of nucleic acid molecules to a patient and subsequent transcription and/or translation of the encoded genetic information. Alternatively, genetic vaccination or gene therapy may also comprise methods, which include isolation of specific body cells from a patient to be treated, subsequent in vitro transfection of such cells, and re-administration of the treated cells to the patient.

DNA as well as RNA may be used as nucleic acid molecules for administration in the context of gene therapy or genetic vaccination. DNA is known to be relatively stable and easy to handle. However, the use of DNA bears the risk of undesired insertion of the administered DNA-fragments into the patient's genome potentially resulting in loss of function of the impaired genes. As a further risk, the undesired generation of anti-DNA antibodies has emerged. Another drawback is the limited expression level of the encoded peptide or protein that is achievable upon DNA administration and its transcription/translation. Among other reasons, the expression level of the administered DNA will be dependent on the presence of specific transcription factors, which regulate DNA transcription. In the absence of such factors, DNA transcription will not yield satisfying amounts of RNA. As a result, the level of translated peptide or protein obtained is limited.

By using RNA instead of DNA for gene therapy or genetic vaccination, the risk of undesired genomic integration and generation of anti-DNA antibodies is minimized or avoided. However, RNA is considered to be a rather unstable molecular species which may readily be degraded by ubiquitous RNAses.

In vivo, RNA-degradation contributes to the regulation of the RNA half-life time. That effect was considered and proven to fine tune the regulation of eukaryotic gene expression (Friedel et al., Conserved principles of mammalian transcriptional regulation revealed by RNA half-life, Nucleic Acid Research, 2009, 1-12). Accordingly, each naturally occurring mRNA has its individual half-life depending on the gene from which the mRNA is derived. It contributes to the regulation of the expression level of this gene. Unstable RNAs are important to realize transient gene expression at distinct points in time. However, long-lived RNAs may be associated with accumulation of distinct proteins or continuous expression of genes. In vivo, the half life of mRNAs may also be dependent on environmental factors, such as hormonal treatment, as has been shown, e.g., for insulin-like growth factor I, actin, and albumin mRNA (Johnson et al., Newly synthesized RNA: Simultaneous measurement in intact cells of transcription rates and RNA stability of insulin-like growth factor I, actin, and albumin in growth hormone-stimulated hepatocytes, Proc. Natl. Acad. Sci., Vol. 88, pp. 5287-5291, 1991).

For gene therapy and genetic vaccination, usually stable RNA is desired. This is, on the one hand, due to the fact that the product encoded by the RNA-sequence shall accumulate in vivo. On the other hand, the RNA has to maintain its structural and functional integrity when prepared for a suitable dosage form, in the course of its storage, and when administered. Thus, considerable attention was dedicated to provide stable RNA molecules for gene therapy or genetic vaccination in order to prevent them from being subject to early degradation or decay.

It has been reported that the G/C-content of nucleic acid molecules may influence their stability. Thus, nucleic acids comprising an increased amount of guanine (G) and/or cytosine (C) residues may be functionally more stable than nucleic acids containing a large amount of adenine (A) and thymine (T) or uracil (U) nucleotides. In this context, WO02/098443 provides a pharmaceutical composition containing an mRNA that is stabilised by sequence modifications in the translated region. Such a sequence modification takes advantage of the degeneracy of the genetic code. Accordingly, codons which contain a less favourable combination of nucleotides (less favourable in terms of RNA stability) may be substituted by alternative codons without altering the encoded amino acid sequence. This method of RNA stabilization is limited by the provisions of the specific nucleotide sequence of each single RNA molecule which is not allowed to leave the space of the desired amino acid sequence. Also, that approach is restricted to coding regions of the RNA.

As an alternative option for mRNA stabilisation, it has been found that naturally occurring eukaryotic mRNA molecules contain characteristic stabilising elements. For example, they may comprise so-called untranslated regions (UTR) at their 5'-end (5'UTR) and/or at their 3'-end (3'UTR) as well as other structural features, such as a 5'-cap structure or a 3'-poly(A) tail. Both, 5'UTR and 3'UTR are typically transcribed from the genomic DNA and are, thus, an element of the premature mRNA. Characteristic structural features of mature mRNA, such as the 5'-cap and the 3'-poly(A) tail (also called poly(A) tail or poly(A) sequence) are usually added to the transcribed (premature) mRNA during mRNA processing.

A 3'-poly(A) tail is typically a monotonous sequence stretch of adenine nucleotides, which is enzymatically added to the 3'-end of the nascent mRNA. Typically, the poly(A) tail of a mammalian mRNA contains about 250 adenine nucleotides. It was found that the length of such a 3'-poly(A) tail is a potentially critical element for the stability of the individual mRNA. In this context, Holtkamp et al. reported that a poly(A) tail consisting of 120 nucleotides resulted in a more stable mRNA molecule, which was expressed more efficiently, than a shorter poly(A) tail (Holtkamp et al., Modification of antigen-encoding RNA increases stability, translational efficacy, and T-cell stimulatory capacity of dendritic cells, Blood, Vol. 108, pp. 4009-4017, 2006). However, according to Holtkamp et al., a further extension of the poly(A) tail does not lead to an additional increase in mRNA stability or expression. It was further reported that enzymatic adenylation of an mRNA comprising a poly(A) tail further enhances expression of the mRNA after electroporation into T cells (Zhao et al., Multiple Injections of Electroporated Autologous T Cells Expressing a Chimeric Antigen Receptor Mediate Regression of Human Disseminated Tumor, Caner Res., Vol. 70(22), pp. 9053-9061, 2010). Nearly all eukaryotic mRNAs end with a poly(A) sequence that is added to their 3'-end by the ubiquitous cleavage/polyadenylation machinery. The presence of a poly(A) sequence at the 3'-end is one of the most recognizable features of eukaryotic mRNAs. After cleavage, most pre-mRNAs, with the exception of replication-dependent histone transcripts, acquire a polyadenylated tail. In this context, 3'-end processing is a nuclear co-transcriptional process that promotes transport of mRNAs from the nucleus to the cytoplasm and affects the stability and the translation of mRNAs. Formation of this 3' end occurs in a two step reaction directed by the cleavage/polyadenylation machinery and de-pends on the presence of two sequence elements in mRNA precursors (pre-mRNAs); a highly conserved hexanucleotide AAUAAA (polyadenylation signal) and a downstream G/U-rich sequence. In a first step, pre-mRNAs are cleaved between these two elements. In a second step tightly coupled to the first step the newly formed 3' end is extended by addition of a poly(A) sequence consisting of 200-250 adenylates which affects subsequently all aspects of mRNA metabolism, including mRNA export, stability and translation (Dominski, Z. and W. F. Marzluff (2007), Gene 396(2): 373-90.).

The only known exception to this rule are the replication-dependent histone mRNAs, which terminate with a histone stem-loop instead of a poly(A) sequence. Exemplary histone stem-loop sequences are described in Lopez et al. (Dávila López, M., & Samuelsson, T. (2008), RNA (New York, N.Y.), 14(1), 1-10. doi:10.1261/rna.782308.).

The stem-loops in histone pre-mRNAs are typically followed by a purine-rich sequence known as the histone downstream element (HDE). These pre-mRNAs are processed in the nucleus by a single endonucleolytic cleavage approximately 5 nucleotides downstream of the stem-loop, catalyzed by the U7 snRNP through base pairing of the U7 snRNA with the HDE.

Due to the requirement to package newly synthesized DNA into chromatin, histone synthesis is regulated in concert with the cell cycle. Increased synthesis of histone proteins during S phase is achieved by transcriptional activation of histone genes as well as post-transcriptional regulation of histone mRNA levels. It could be shown that the histone stem-loop is essential for all posttranscriptional steps of histone expression regulation. It is necessary for efficient processing, export of the mRNA into the cytoplasm, loading onto polyribosomes, and regulation of mRNA stability.

In the above context, a 32 kDa protein was identified, which is associated with the histone stem-loop at the 3'-end of the histone messages in both the nucleus and the cytoplasm. The expression level of this stem-loop binding protein (SLBP) is cell cycle regulated and is highest during S-phase when histone mRNA levels are increased. SLBP is necessary for efficient 3'-end processing of histone pre-mRNA by the U7 snRNP. After completion of processing, SLBP remains associated with the stem-loop at the end of mature histone mRNAs and stimulates their translation into histone proteins in the cytoplasm. (Dominski, Z. and W. F. Marzluff (2007), Gene 396(2): 373-90). Interestingly, the RNA binding domain of SLBP is conserved throughout metazoa and protozoa (Dávila López, M., & Samuelsson, T. (2008), RNA (New York, N.Y.), 14(1), 1-10. doi:10.1261/rna.782308) and it could be shown that its binding to the histone stem-loop sequence is dependent on the stem-loop structure and that the minimum binding site contains at least 3 nucleotides 5' and 2 nucleotides 3' of the stem-loop (Pandey, N. B., et al. (1994), Molecular and Cellular Biology, 14(3), 1709-1720 and Williams, A. S., & Marzluff, W. F., (1995), Nucleic Acids Research, 23(4), 654-662.).

Even though histone genes are generally classified as either "replication-dependent", giving rise to mRNA ending in a histone stem-loop, or "replacement-type", giving rise to mRNA bearing a poly(A)-tail instead, naturally occurring mRNAs containing both a histone stem-loop and poly(A) or oligo(A) 3' thereof have been identified in some very rare cases. Sanchez et al. examined the effect of naturally occurring oligo(A) tails appended 3' of the histone stem-loop of histone mRNA during *Xenopus oogenesis* using luciferase as a reporter protein and found that the oligo(A) tail is an active part of the translation repression mechanism that silences histone mRNA during oogenesis and its removal is part of the mechanism that activates translation of histone mRNAs (Sanchez, R. and W. F. Marzluff (2004), Mol Cell Biol 24(6): 2513-25).

Furthermore, the requirements for regulation of replication dependent histones at the level of pre-mRNA processing and mRNA stability have been investigated using artificial constructs coding for the marker protein alpha globin, taking advantage of the fact that the globin gene contains introns as opposed to the intron-less histone genes. For this purpose, constructs were generated in which the alpha globin coding sequence was followed by a histone stem-loop signal (histone stem-loop followed by the histone downstream element) and a polyadenylation signal (Whitelaw, E., et al. (1986). Nucleic Acids Research, 14(17), 7059-7070; Pandey, N. B., & Marzluff, W. F. (1987). Molecular and Cellular Biology, 7(12), 4557-4559; Pandey, N. B., et al. (1990). Nucleic Acids Research, 18(11), 3161-3170).

Also, it was shown that the 3'UTR of α-globin mRNA may be an important factor for the well-known stability of α-globin mRNA (Rodgers et al., Regulated α-globin mRNA decay is a cytoplasmic event proceeding through 3'-to-5' exosome-dependent decapping, RNA, 8, pp. 1526-1537, 2002). The 3'UTR of α-globin mRNA is obviously involved in the formation of a specific ribonucleoprotein-complex, the α-complex, whose presence correlates with mRNA stability in vitro (Wang et al., An mRNA stability complex functions with poly(A)-binding protein to stabilize mRNA in vitro, Molecular and Cellular Biology, Vol 19, No. 7, July 1999, p. 4552-4560).

Irrespective of factors influencing mRNA stability, effective translation of the administered nucleic acid molecules by the target cells or tissue is crucial for any approach using nucleic acid molecules for gene therapy or genetic vaccination. Along with the regulation of stability, also translation of the majority of mRNAs is regulated by structural features like UTRs, 5'-cap and 3'-poly(A) tail. In this context, it has been reported that the length of the poly(A) tail may play an important role for translational efficiency as well. Stabilizing 3'-elements, however, may also have an attenuating effect on translation.

Further regulative elements, which may have an influence on expression levels, may be found in the 5'UTR. For example, it has been reported that synthesis of particular proteins, e.g. proteins belonging to the translational apparatus, may be regulated not only at the transcriptional but also at the translational level. For example, translation of proteins encoded by so called 'TOP-genes' may be down-regulated by translational repression. Therein, the term 'TOP-gene' relates to a gene corresponding to an mRNA that is characterized by the presence of a TOP sequence at the 5'end and in most cases by a growth-associated translation regulation (Iadevaia et al., All translation elongation factors and the e, f, and h subunits of translation initiation factor 3 are encoded by 5'-terminal oligopyrimidine (TOP) mRNAs; RNA, 2008, 14:1730-1736). In this context, a TOP sequence—also called the '5'-terminal oligopyrimidine tract'—typically consists of a C residue at the cap site, followed by an uninterrupted sequence of up to 13 or even more pyrimidines (Avni et al., Vertebrate mRNAs with a 5'-terminal pyrimidine tract are Candidates for translational repression in quiescent cells: characterization of the translational cis-regulatory element, Molecular and Cellular Biology, 1994, p. 3822-3833). These TOP sequences are reported to be present in many mRNAs encoding components of the translational machinery and to be responsible for selective repression of the translation of these TOP containing mRNAs due to growth arrest (Meyuhas, et al., Translational Control of Ribosomal Protein mRNAs in Eukaryotes, Translational Control. Cold Spring Harbor Monograph Archive. Cold Spring Harbor Laboratory Press, 1996, p. 363-388).

It is the object of the invention to provide artificial nucleic acid molecules, which may be suitable for use as a medicament or a vaccine, preferably for application in gene therapy and/or genetic vaccination. Particularly, it is the object of the invention to provide artificial nucleic acid molecules, such as an mRNA species, which provide for improved protein production from said artificial nucleic acid molecules. Another object of the present invention is to provide nucleic acid molecules encoding such a superior mRNA species, which may be amenable for use as a medicament or a vaccine, preferably in gene therapy and/or genetic vaccination. It is a further object of the present invention to provide a pharmaceutical composition, preferably for use as a medicament or a vaccine, preferably in gene therapy and/or genetic vaccination. In summary, it is the object of the present invention to provide improved nucleic acid species, which overcome the above discussed disadvantages of the prior art by means of a cost-effective and straightforward approach.

The object underlying the present invention is solved by the claimed subject-matter.

For the sake of clarity and readability the following definitions are provided. Any technical feature mentioned for these definitions may be read on each and every embodiment of the invention. Additional definitions and explanations may be specifically provided in the context of these embodiments.

Adaptive immune response: The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs, through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T cells. Therein, presenting the antigen on MHC molecules leads to activation of T cells, which induces their proliferation and differentiation into armed effector T cells. The most important function of effector T cells is the killing of infected cells by CD8+ cytotoxic T cells and the activation of macrophages by Th1 cells, which together make up cell-mediated immunity, and the activation of B cells by both Th2 and Th1 cells to produce different classes of antibody, thus driving the humoral immune response. T cells recognize an antigen by their T cell receptors, which do not recognize and bind the antigen directly, but instead recognize short peptide fragments, e.g. of pathogen-derived protein antigens, e.g. so-called epitopes, which are bound to MHC molecules on the surfaces of other cells.

Adaptive immune system: The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Adjuvant/adjuvant component: An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Antigen: In the context of the present invention, "antigen" refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein, which may be presented by the MHC to T-cells. In the sense of the present invention, an antigen may be the product of translation of a provided nucleic acid molecule, preferably an mRNA, as defined herein. In this context, also fragments, variants and derivatives of peptides and proteins comprising at least one epitope are understood as antigens. In the context of the present invention, tumour antigens and pathogenic antigens as defined herein are particularly preferred.

Artificial nucleic acid molecule: An artificial nucleic acid molecule may typically be understood to be a nucleic acid molecule, e.g. a DNA or an RNA, that does not occur naturally. In other words, an artificial nucleic acid molecule may be understood as a non-natural nucleic acid molecule. Such nucleic acid molecule may be non-natural due to its individual sequence (which does not occur naturally) and/or due to other modifications, e.g. structural modifications of nucleotides which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context, an artificial sequence is usually a sequence that may not occur naturally, i.e. it differs from the wild type sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

Bicistronic RNA, multicistronic RNA: A bicistronic or multicistronic RNA is typically an RNA, preferably an mRNA, that may typically have two (bicistronic) or more (multicistronic) open reading frames (ORF). An open reading frame in this context is a sequence of codons that is translatable into a peptide or protein.

Carrier/polymeric carrier: A carrier in the context of the invention may typically be a compound that facilitates transport and/or complexation of another compound (cargo). A polymeric carrier is typically a carrier that is formed of a polymer. A carrier may be associated to its cargo by covalent or non-covalent interaction. A carrier may transport nucleic acids, e.g. RNA or DNA, to target cells. The carrier may—for some embodiments be a cationic component.

Cationic component: The term "cationic component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic component may be any positively charged compound or polymer, preferably a cationic peptide or protein, which is positively charged under physiological conditions, particularly under physiological conditions in vivo. A "cationic peptide or protein" may contain at least one positively charged amino acid, or more than one positively charged amino acid, e.g. selected from Arg, His, Lys or Orn. Accordingly, "polycationic" components are also within the scope exhibiting more than one positive charge under the conditions given.

5'-cap: A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'-phosphorothioate, phosphorodithioate, or bridging or non-bridging methylphosphonate moiety.

Cellular immunity/cellular immune response: Cellular immunity typically relates to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens, and stimulation of cells to secrete a variety of cytokines that influence the function of other cells involved in adaptive immune responses and innate immune responses.

DNA: DNA is the usual abbreviation for deoxy-ribo-nucleic acid. It is a nucleic acid molecule, i.e. a polymer consisting of nucleotides. These nucleotides are usually deoxy-adenosine-monophosphate, deoxy-thymidine-monophosphate, deoxy-guanosine-monophosphate and deoxy-cytidine-monophosphate monomers, which are—by themselves—composed of a sugar moiety (deoxyribose), a base moiety and a phosphate moiety, and polymerise to form a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA sequence. DNA may be single stranded or double stranded. In the double stranded form, the nucleotides of the first strand typically hybridize with the nucleotides of the second strand, e.g. by A/T-base-pairing and G/C-base-pairing.

Epitope: Epitopes (also called "antigen determinants") can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in the form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form. Such epitopes of proteins or peptides may furthermore be selected from any of the herein mentioned variants of such proteins or peptides. In this context, antigenic determinants can be conformational or discontinuous epitopes, which are composed of segments of the proteins or peptides as defined herein that are discontinuous in the amino acid sequence of the proteins or peptides as defined herein, but are brought together in the three-dimensional structure or continuous or linear epitopes, which are composed of a single polypeptide chain.

Fragment of a sequence: A fragment of a sequence may typically be a shorter portion of a full-length sequence of e.g. a nucleic acid molecule or an amino acid sequence. Accordingly, a fragment typically consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 5%, 10%, 20%, preferably at least 30%, more preferably at least 40%, more preferably at least 50%, even more preferably at least 60%, even more preferably at least 70%, and most preferably at least 80% of the total (i.e. full-length) molecule, from which the fragment is derived.

G/C modified: A G/C-modified nucleic acid may typically be a nucleic acid, preferably an artificial nucleic acid molecule as defined herein, based on a modified wild-type sequence comprising a preferably increased number of guanosine and/or cytosine nucleotides as compared to the wild-type sequence. Such an increased number may be generated by substitution of codons containing adenosine or thymidine nucleotides by codons containing guanosine or cytosine nucleotides. If the enriched G/C content occurs in a coding region of DNA or RNA, it makes use of the degeneracy of the genetic code. Accordingly, the codon substitutions preferably do not alter the encoded amino acid residues, but exclusively increase the G/C content of the nucleic acid molecule.

Gene therapy: Gene therapy may typically be understood to mean a treatment of a patient's body or isolated elements of a patient's body, for example isolated tissues/cells, by nucleic acids encoding a peptide or protein. It may typically comprise at least one of the steps of a) administration of a nucleic acid, preferably an artificial nucleic acid molecule as defined herein, directly to the patient—by whatever administration route—or in vitro to isolated cells/tissues of the patient, which results in transfection of the patient's cells either in vivo/ex vivo or in vitro; b) transcription and/or translation of the introduced nucleic acid molecule; and optionally c) re-administration of isolated, transfected cells to the patient, if the nucleic acid has not been administered directly to the patient.

Genetic vaccination: Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an artificial nucleic acid molecule as defined herein, to a subject, preferably a patient, or to isolated cells of a subject, preferably a patient, which usually results in transfection of the subject's cells, either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Heteroloqous sequence: Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Humoral immunity/humoral immune response: Humoral immunity refers typically to antibody production and optionally to accessory processes accompanying antibody production. A humoral immune response may typically be characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Immunogen: In the context of the present invention, an immunogen may typically be understood to be a compound that is able to stimulate an immune response. Preferably, an immunogen is a peptide, polypeptide, or protein. In a particularly preferred embodiment, an immunogen in the sense of the present invention is the product of translation of a provided nucleic acid molecule, preferably an artificial nucleic acid molecule as defined herein. Typically, an immunogen elicits at least an adaptive immune response.

Immunostimulatory composition: In the context of the invention, an immunostimulatory composition may be typically understood to be a composition containing at least one component, which is able to induce an immune response or from which a component which is able to induce an immune response is derivable. Such immune response may be preferably an innate immune response or a combination of an adaptive and an innate immune response. Preferably, an immunostimulatory composition in the context of the invention contains at least one artificial nucleic acid molecule, more preferably an RNA, for example an mRNA molecule.

The immunostimulatory component, such as the mRNA may be complexed with a suitable carrier. Thus, the immunostimulatory composition may comprise an mRNA/carrier-complex. Furthermore, the immunostimulatory composition may comprise an adjuvant and/or a suitable vehicle for the immunostimulatory component, such as the mRNA.

Immune response: An immune response may typically be a specific reaction of the adaptive immune system to a particular antigen (so called specific or adaptive immune response) or an unspecific reaction of the innate immune system (so called unspecific or innate immune response), or a combination thereof.

Immune system: The immune system may protect organisms from infection. If a pathogen succeeds in passing a physical barrier of an organism and enters the organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained also after the pathogen has been eliminated, in the form of an immunological memory, and allows the adaptive immune system to mount faster and stronger attacks each time this pathogen is encountered. Accordingly, the immune system comprises the innate and the adaptive immune system. Each of these two parts typically contains so called humoral and cellular components.

Immunostimulatory RNA: An immunostimulatory RNA (isRNA) in the context of the invention may typically be an RNA that is able to induce an innate immune response. It usually does not have an open reading frame and thus does not provide a peptide-antigen or immunogen but elicits an immune response e.g. by binding to a specific kind of Toll-like-receptor (TLR) or other suitable receptors. However, of course also mRNAs having an open reading frame and encoding a peptide/protein may induce an innate immune response and, thus, may be immunostimulatory RNAs.

Innate immune system: The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNFalpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. The pharmaceutical composition according to the present invention may comprise one or more such substances. Typically, a response of the innate immune system includes recruiting immune cells to sites of infection, through the production of chemical factors, including specialized chemical mediators, which are called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes, which cleave the DNA at these sites. A cloning site, which comprises more than one restriction site may also be termed a multiple cloning site (MCS) or a polylinker.

Nucleic acid molecule: A nucleic acid molecule is a molecule comprising, preferably consisting of nucleic acid components. The term nucleic acid molecule preferably refers to DNA or RNA molecules. It is preferably used synonymously with the term "polynucleotide". Preferably, a nucleic acid molecule is a polymer comprising or consisting of nucleotide monomers, which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Open reading frame: An open reading frame (ORF) in the context of the invention may typically be a sequence of several nucleotide triplets, which may be translated into a peptide or protein. An open reading frame preferably contains a start codon, i.e. a combination of three subsequent nucleotides coding usually for the amino acid methionine (ATG), at its 5'-end and a subsequent region, which usually exhibits a length, which is a multiple of 3 nucleotides. An ORF is preferably terminated by a stop-codon (e.g., TAA, TAG, TGA). Typically, this is the only stop-codon of the open reading frame. Thus, an open reading frame, in the context of the present invention, is preferably a nucleotide sequence, consisting of a number of nucleotides that may be divided by three, which starts with a start codon (e.g. ATG) and which preferably terminates with a stop codon (e.g., TAA, TGA, or TAG). The open reading frame may be isolated or it may be incorporated into a longer nucleic acid sequence, for example into a vector or an mRNA. An open reading frame may also be termed "protein coding region".

Peptide: A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Protein: A protein typically comprises one or more peptides or polypeptides. A protein is typically folded into 3-dimensional form, which may be required for the protein to exert its biological function.

Poly(A) sequence: A poly(A) sequence, also called poly (A) tail or 3'-poly(A) tail, is usually understood to be a sequence of adenine nucleotides, e.g., of up to about 400 adenosine nucleotides, e.g. from about 20 to about 400, preferably from about 50 to about 400, more preferably from about 50 to about 300, even more preferably from about 50 to about 250, most preferably from about 60 to about 250 adenosine nucleotides, which is preferably added to the 3'-terminus of an mRNA. A poly(A) sequence is typically located at the 3'-end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector. In the context of the present invention, the term 'poly(A) sequence' further comprises also sequence elements, preferably artificial sequence elements, that are part of the 3'-UTR or located at the 3'-terminus of the artificial nucleic acid molecule, and which preferably comprise up to 1100 adenine nucleotides, more preferably at least 60, 70, 80, 90, 100, 110, 120, 130, 140, 150, 160, 170, 180, 190, 200, 210, 220, 230, 240, 250, 300, 350, 400, 500, 600, 700, 800, 900, or at least 1000 adenine nucleotides.

Polyadenylation: Polyadenylation is typically understood to be the addition of a poly(A) sequence to a nucleic acid molecule, such as an RNA molecule, e.g. to a premature mRNA. Polyadenylation may be induced by a so-called polyadenylation signal. This signal is preferably located within a stretch of nucleotides close to or at the 3'-end of a nucleic acid molecule, such as an RNA molecule, to be polyadenylated. In the context of the present invention, a polyadenylation signal may also be comprised by the 3'-UTR of the artificial nucleic acid molecule. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation. As used in the context of the present invention, the term may relate to polyadenylation of RNA as a cellular process as well as to polyadenylation carried out by enzymatic reaction in vitro or by chemical synthesis.

Restriction site: A restriction site, also termed restriction enzyme recognition site, is a nucleotide sequence recognized by a restriction enzyme. A restriction site is typically a short, preferably palindromic, nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence.

RNA, mRNA: RNA is the usual abbreviation for ribonucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA sequence. Usually, RNA may be obtainable by transcription of a DNA sequence, e.g., inside a cell. In eukaryotic cells, transcription is typically performed inside the nucleus or the mitochondria. In vivo, transcription of DNA usually results in the so-called premature RNA, which has to be processed into so-called messenger RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, a 5'-UTR, an open reading frame, a 3'-UTR and a poly(A) sequence. Aside from messenger RNA, several non-coding types of RNA exist, which may be involved in the regulation of transcription and/or translation.

Sequence of a nucleic acid molecule: The sequence of a nucleic acid molecule is typically understood to be the particular and individual order, i.e. the succession of its nucleotides. The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence. For the determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence, which have the same position in two or more sequences having the same length. Gaps are usually regarded as non-identical positions, irrespective of their actual position in an alignment.

Stabilized nucleic acid molecule: A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Transfection: The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Vaccine: A vaccine is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response.

Vector: The term "vector" refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. Such vectors may be storage vectors, expression vectors, cloning vectors, transfer vectors etc. A storage vector is a vector, which allows the convenient storage of a nucleic acid molecule, for example, of an mRNA molecule. Thus, the vector may comprise a sequence corresponding, e.g., to a desired mRNA sequence or a part thereof, such as a sequence corresponding to the open reading frame and the 3'-UTR of an mRNA. An expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA polymerase promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector, which is suitable for transferring nucleic acid molecules into cells or organisms, for example, viral vectors. A vector in the context of the present invention may be, e.g., an RNA vector or a DNA vector. Preferably, a vector is a DNA molecule. Preferably, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Vehicle: A vehicle is typically understood to be a material that is suitable for storing, transporting, and/or administering a compound, such as a pharmaceutically active compound. For example, it may be a physiologically acceptable liquid, which is suitable for storing, transporting, and/or administering a pharmaceutically active compound.

3'-untranslated region (3'-UTR): Generally, the term "3'-UTR" refers to a part of the artificial nucleic acid molecule, which is located 3' (i.e. "downstream") of an open reading frame and which is not translated into protein. Typically, a 3'-UTR is the part of an mRNA, which is located between the protein coding region (open reading frame (ORF) or coding sequence (CDS)) and the poly(A) sequence of the mRNA. In the context of the invention, a 3'-UTR of the artificial nucleic acid molecule may comprise more than one 3'-UTR elements, which may be of different origin, such as sequence elements derived from the 3'-UTR of several (unrelated) naturally occurring genes. Accordingly, the term 3'-UTR may also comprise elements, which are not encoded in the template, from which an RNA is transcribed, but which are added after transcription during maturation, e.g. a poly(A) sequence. A 3'-UTR of the mRNA is not translated into an amino acid sequence. The 3'-UTR sequence is generally encoded by the gene, which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'capping, splicing the pre-mature mRNA to excize optional introns and modifications of the 3'-end, such as polyadenylation of the 3'-end of the pre-mature mRNA and optional endo-/or exonuclease cleavages etc. In the context of the present invention, a 3'-UTR corresponds to the sequence of a mature mRNA which is located between the stop codon of the protein coding region, preferably immediately 3' to the stop codon of the protein coding region, and the poly(A) sequence of the mRNA. The term "corresponds to" means that the 3'-UTR sequence may be an RNA sequence, such as in the mRNA sequence used for defining the 3'-UTR sequence, or a DNA sequence, which corresponds to such RNA sequence. In the context of the present invention, the term "a 3'-UTR of a gene", such as "a 3'-UTR of a ribosomal protein gene", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence (both sense and antisense strand and both mature and immature) of the 3'-UTR. As used herein, the term "3'-UTR element" typically refers to a fragment of a 3'-UTR as defined herein. In particular, the term comprises any nucleic acid sequence element, which is located 3' to the ORF in the artificial nucleic acid molecule, preferably the mRNA, according to the invention. Accordingly, the term covers, for example, sequence elements derived from the 3'-UTR of a heterologous gene as well as elements such as a poly(C) sequence or a histone stem-loop.

5'-untranslated region (5'-UTR): A 5'-UTR is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, which are also called regulatory elements. Such regulatory elements may be, for example, ribosomal binding sites. The 5'-UTR may be posttranscriptionally modified, for example by addition of a 5'-cap. In the context of the present invention, a 5'-UTR corresponds to the sequence of a mature mRNA, which is located between the 5'-cap and the start codon. Preferably, the 5'-UTR corresponds to the sequence, which extends from a nucleotide located 3' to the 5'-cap, preferably from the nucleotide located immediately 3' to the 5'-cap, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence, which corresponds to such RNA sequence. In the context of the present invention, the term "a 5'-UTR of a gene" is the sequence, which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR.

5' Terminal Oliqopyrimidine Tract (TOP): The 5'terminal oligopyrimidine tract (TOP) is typically a stretch of pyrimidine nucleotides located in the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence, which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'-end with a cytosine nucleotide. In TOP genes and TOP mRNAs, the TOP motif preferably starts at its 5'-end with the transcriptional start site and ends one nucleotide 5' to the first purine residue in said gene or mRNA. A TOP motif in the sense of the present invention is preferably located at the 5'-end of a sequence, which represents a 5'-UTR or at the 5'-end of a sequence, which codes for a 5'-UTR. Thus, preferably, a stretch of 3 or more pyrimidine nucleotides is called "TOP motif" in the sense of the present invention if this stretch is located at the 5'end of a respective sequence, such as the artificial nucleic acid molecule, the 5'-UTR element of the artificial nucleic acid molecule, or the nucleic acid sequence which is derived from the 5'-UTR of a TOP gene as described herein. In other words, a stretch of 3 or more pyrimidine nucleotides, which is not located at the 5'-end of a 5'-UTR or a 5'-UTR element but anywhere within a 5'-UTR or a 5'-UTR element, is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'-UTR of a TOP gene corresponds to the sequence of a 5'-UTR of a mature mRNA derived from a TOP gene, which preferably extends from the nucleotide located 3' to the 5'-cap to the nucleotide located 5' to the start codon. A 5'-UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'-UTRs of TOP genes are generally rather short. The lengths of 5'-UTRs of TOP genes may vary from 20 nucleotides up to 500 nucleotides, and are typically less than about 200 nucleotides, preferably less than about 150 nucleotides, more preferably less than about 100 nucleotides. Exemplary 5'-UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363 of the patent application WO2013/143700, whose disclosure is incorporated herewith by reference. In this context, a particularly preferred fragment of a 5'-UTR of a TOP gene is a 5'-UTR of a TOP gene lacking the 5'TOP motif. The terms "5'-UTR of a TOP gene" or "5'-TOP UTR" preferably refer to the 5'-UTR of a naturally occurring TOP gene.

In a first aspect, the present invention relates to an artificial nucleic acid molecule comprising
 a) at least one open reading frame (ORF); and
 b) a 3'-untranslated region (3'-UTR) comprising
  b)i) at least one poly(A) sequence, wherein the at least one poly(A) sequence comprises at least 70 adenine nucleotides, or
  b)ii) a polyadenylation signal.

The artificial nucleic acid molecule according to the present invention may be an RNA, such as an mRNA, a DNA, such as a DNA vector, or may be a modified RNA or DNA molecule. It may be provided as a double-stranded molecule having a sense strand and an anti-sense strand, for example, as a DNA molecule having a sense strand and an anti-sense strand.

It is preferred that the artificial nucleic acid molecule according to the invention is preferably characterized by an increased protein expression with respect to a reference nucleic acid molecule.

In the context of the present invention, a "reference nucleic acid molecule" is a nucleic acid molecule, which typically comprises the same ORF as the artificial nucleic acid molecule, and which lacks a 3'-UTR or which comprises a reference 3'-UTR. Preferably, the reference nucleic acid molecule comprises a 3'-UTR (i.e. a "reference 3'-UTR"), which either does not comprise a poly(A) sequence, or which comprises a poly(A) sequence, wherein the total number of adenine nucleotides comprised in one or more poly(A) sequence of the 3'-UTR is lower than the total number of adenine nucleotides comprised in the at least one poly(A) sequence of the 3'-UTR of the artificial nucleic acid molecule according to the invention, preferably lower than 70. Preferably, the reference nucleic acid molecule has—besides the different content of adenine nucleotides in a poly(A) sequence—the same overall structure, i.e. comprises the same structural features, such as, for example, a 5'-cap structure, a 5'-UTR or a 3'-UTR. More preferably, the reference nucleic acid molecule comprises or consists of—besides the different content of adenine nucleotides in a poly(A) sequence—the same nucleic acid sequence as the artificial nucleic acid molecule. In the context of the present invention, the naturally occurring nucleic acid sequence (e.g. an mRNA) comprising the ORF of the artificial nucleic acid molecule may also be the reference nucleic acid molecule.

In certain embodiments, a RNA molecule comprises a 5' UTR, an ORF and 3' UTR sequence, wherein the 5' UTR sequence or the 3' UTR sequence is heterologous relative the ORF of the mRNA (e.g., wherein the RNA does not comprise the 5' UTR sequence and/or the 3' UTR sequence of a wild type RNA encoding the ORF).

As used herein, the term "total number of adenine nucleotides" typically refers to the sum of all adenine nucleotides, which are comprised in one or more poly(A) sequences in the 3'-UTR of the inventive artificial nucleic acid molecule. In particular, in the case, where the 3'-UTR comprises more than one poly(A) sequences, the term refers to the sum of the adenine nucleotides comprised in all poly(A) sequences comprised in the 3'-UTR of the artificial nucleic acid molecule.

In one embodiment of the present invention, the artificial nucleic acid molecule according to the present invention comprises a 3'-UTR, wherein the total number of adenine nucleotides comprised in one or more poly(A) sequences of the 3'-UTR is at least 60, 70, 80, 90, 100, 110, 120, 130, 140, 150, 160, 170, 180, 190, 200, 210, 220, 230, 240, 250, 300, 350, 400, 500, 600, 700, 800, 900, 1000 or 1100 adenine nucleotides. According to that embodiment, the 3'-UTR may comprise, for example, two, preferably separate, poly(A) sequences, wherein the sum of adenine nucleotides comprised in said two poly(A) sequences is at least 60, 70, 80, 90, 100, 110, 120, 130, 140, 150, 160, 170, 180, 190, 200, 210, 220, 230, 240, 250, 300, 350, 400, 500, 600, 700, 800, 900, 1000 or 1100.

In a further embodiment there is provided a composition comprising a plurality of RNA molecules of the embodiments in pharmaceutically acceptable carrier, wherein at least about 90%, 91%, 92%, 93%, 94%, 95%, 96%, 97%, 98%, 99% or greater of the RNA in the composition comprises a poly(A) sequence that differs in length by no more than 10 nucleotides. In a preferred embodiment at least about 90%, 91%, 92%, 93%, 94%, 95%, 96%, 97%, 98%, 99% or greater of the RNA in the composition comprises a poly(A) sequence of identical length. In certain embodiments, the poly(A) sequence is positioned at the 3' end of the RNA, with no other nucleotides positioned 3' relative the poly(A) sequence. In still a further embodiment, there is provided a composition comprising a plurality of RNA molecules of the embodiments in pharmaceutically acceptable carrier, wherein said plurality of RNA molecules comprise both capped and uncapped RNAs. For example, in some aspects, a composition comprises a plurality of RNA molecules wherein no more than 95%, 90%, 80%, 70% or 60% of the RNAs comprise a cap and the remaining RNA molecules are uncapped.

In a preferred embodiment, the artificial nucleic acid molecule comprises a 3'-UTR comprising at least one poly (A) sequence, wherein the at least one poly(A) sequence comprises at least 60, 70, 80, 90, 100, 110, 120, 130, 140, 150, 160, 170, 180, 190, 200, 210, 220, 230, 240, 250, 300, 350, 400, 500, 600, 700, 800, 900, or 1000 adenine nucleotides.

The total number of adenine nucleotides comprised in the one or more poly(A) sequences may be up to about 1200 adenine nucleotides, e.g. from about 70 to about 1100, preferably from about 80 to about 800, more preferably from about 90 to about 700, even more preferably from about 100 to about 500, most preferably from about 120 to about 450 adenosine nucleotides. Preferably, the 3'-UTR of the artificial nucleic acid molecule comprises at least 75, 80, 85, 95, 100, 105, 110, 115, 120, 125, 130, 135, 140, 145, 150, 155, 160, 165, 170, 175, 180, 185, 190, 195, 200, 205, 210, 215, 220, or at least 225, more preferably at least 220, adenine nucleotides comprised in the one or more poly(A) sequences. Preferably, the 3'-UTR of the artificial nucleic acid molecule comprises from 180 to 1100 adenine nucleotides comprised in the one or more poly(A) sequences, more preferably from 200 to 1100 adenine nucleotides, even more preferably from 210 to 250 adenine nucleotides, most preferably from 215 to 240 adenine nucleotides. In a particularly preferred embodiment, the 3'-UTR comprises about 220 nucleotides, preferably about 224 nucleotides. Alternatively, the 3'-UTR comprises at least 300 adenine nucleotides comprised in the one or more poly(A) sequences, preferably at least 300, 310, 320, 330, 340, 350, 360, 370, 380, 390, 400, 410, 420, 430, or at least 440 adenin nucleotides comprised in the one or more poly(A) sequences. In that embodiment, the 3'-UTR of the artificial nucleic acid molecule preferably comprises from 300 to 650 adenine nucleotides comprised in the one or more poly(A) sequences, more preferably from 400 to 500 adenine nucleotides, even more preferably from 420 to 470 adenine nucleotides, most preferably from 430 to 460 adenine nucleotides. In a particularly preferred embodiment, the 3'-UTR comprises a total number of about 440 adenine nucleotides, preferably about 444 adenine nucleotides, comprised in the one or more poly(A) sequences. Alternatively, the 3'-UTR comprises at least 900 adenine nucleotides comprised in the one or more poly(A) sequences, preferably at least 900, 950 or at least 1000 adenine nucleotides comprised in the one or more poly(A) sequences. In that embodiment, the 3'-UTR of the artificial nucleic acid molecule preferably comprises from 900 to 1100 adenine nucleotides comprised in the one or more poly(A) sequences. In a particularly preferred embodiment, the 3'-UTR comprises a total number of about 1064 adenine nucleotides comprised in the one or more poly(A) sequences.

In a preferred embodiment, the artificial nucleic acid molecule comprises a 3'-UTR comprising at least one poly (A) sequence, which comprises at least 60, 70, 80, 90, 100, 110, 120, 130, 140, 150, 160, 170, 180, 190, 200, 210, 220, 230, 240 or 250 adenine nucleotides, more preferably at least 150 adenine nucleotides, even more preferably at least 160 adenine nucleotides. Preferably, the number of adenine nucleotides comprised in the at least one poly(A) sequence is from 110 to 200, from 120 to 200, from 130 to 190, from 140 to 180, or from 150 to 170. Alternatively, the 3'-UTR comprises at least one poly(A) sequence, which preferably comprises at least 300 adenine nucleotides, more preferably at least 350 adenine nucleotides, even more preferably at least 380 adenine nucleotides. Preferably, the at least one poly(A) sequence comprises from 320 to 430, from 330 to 420, from 340 to 410, from 350 to 400, from 360 to 400, or from 370 to 390. Alternatively, the 3'-UTR comprises at least one poly(A) sequence, which preferably comprises at least 900 adenine nucleotides, more preferably at least 900, 950 or at least 1000 adenine nucleotides. In that embodiment, the 3'-UTR of the artificial nucleic acid molecule preferably comprises at least one poly(A) sequence, which preferably comprises from 900 to 1100 or from 1000 to 1100 adenine nucleotides.

The at least one poly(A) sequence may be located at any position within the 3'-UTR. Thus, the at least one poly(A) sequence may be located at the 3' terminus of the 3'-UTR, i.e. the 3'-UTR does preferably not contain more than 12, 11, 10, 9, 8, 7, 6, 5, 4, 3, 2 or 1 nucleotides located 3' of said poly(A) sequence; more preferably the 3'-UTR does not contain further elements located 3' to said poly(A) sequence. In a preferred embodiment, the at least one poly(A) sequence is located at the 3' terminus of the artificial nucleic acid molecule, i.e. the artificial nucleic acid molecule does preferably not contain more than 12, 11, 10, 9, 8, 7, 6, 5, 4, 3, 2 or 1 nucleotides located 3' of said poly(A) sequence. Alternatively, the at least one poly(A) sequence may be located at the 5' terminus of the 3'-UTR, i.e. immediately 3' of the ORF of the artificial nucleic acid molecule, or located within the 3'-UTR, i.e. flanked on the 5' and on the 3' side by other 3'-UTR elements. Preferably, the at least one poly(A) sequence is flanked on the 3' side by a poly(C) sequence and/or a histone stem-loop sequence. In addition or alternatively, the at least one poly(A) sequence is flanked on the 5' side by a 3'-UTR element derived from a, preferably human, albumin or globin gene, preferably albumin7 as defined herein.

In a preferred embodiment, the artificial nucleic acid molecule comprises a 3'-UTR comprising at least one poly (A) sequence, wherein at least one poly(A) sequence is located at the 3' terminus of the 3'-UTR and wherein the poly(A) sequence at the 3' terminus of the 3'-UTR comprises at least 60, 70, 80, 90, 100, 110, 120, 130, 140, 150, 160, 170, 180, 190, 200, 210, 220, 230, 240, 250, 300, 350, 400, 500, 600, 700, 800, 900, or 1000 adenine nucleotides, more preferably at least 150 adenine nucleotides, even more preferably at least 160 adenine nucleotides. Preferably, the number of adenine nucleotides comprised in the poly(A) sequence located at the 3' terminus of the 3'-UTR is from 110 to 200, from 120 to 200, from 130 to 190, from 140 to 180, or from 150 to 170. Alternatively, the poly(A) sequence at the 3' terminus of the 3'-UTR preferably comprises at least 300 adenine nucleotides, more preferably at least 350 adenine nucleotides, even more preferably at least 380 adenine nucleotides. Preferably, the number of adenine nucleotides comprised in the poly(A) sequence located at the 3' terminus of the 3'-UTR is from 320 to 430, from 330 to 450, from 340 to 410, from 350 to 400, from 360 to 400, or from 370 to 390. In a preferred embodiment, the poly(A) sequence located at the 3' terminus of the 3'-UTR comprises about 160, about 380 or about 430 adenine nucleotides. Further alternatively, the poly(A) sequence at the 3' terminus of the 3'-UTR preferably comprises at least at least 900 adenine nucleotides, more preferably at least 900, 950 or at least 1000 adenine nucleotides. Preferably, the number of adenine nucleotides comprised in the poly(A) sequence located at the 3' terminus of the 3'-UTR is from 900 to 1100 or from 1000 to 1100 adenine nucleotides. In a particularly preferred embodiment, the poly(A) sequence at the 3' terminus of the 3'-UTR preferably comprises about 1000 adenine nucleotides.

In one embodiment, the artificial nucleic acid molecule comprises a 3'-UTR comprising only one poly(A) sequence and, optionally, other 3'-UTR elements as defined herein. Therein, the 3'-UTR preferably further comprises an optional 3'-UTR element, preferably as defined herein, a poly(C) sequence and/or a histone stem-loop sequence. In a particularly preferred embodiment, the 3'-UTR comprises, preferably in 5' to 3' direction, an optional 3'-UTR element, preferably as defined herein, a poly(A) sequence, a poly(C) sequence and a histone stem-loop sequence.

In another embodiment, the artificial nucleic acid molecule comprises a 3'-UTR comprising at least two poly(A) sequences. Preferably, a first poly(A) sequence is located at the 5' terminus of the 3'-UTR or located at a position within the 3'-UTR, i.e. flanked on the 5' and on the 3' side by other UTR-elements, while a second poly(A) sequence is located at a position within the 3'-UTR or at the 3' terminus of the 3'-UTR. Preferably, the first poly(A) sequence is flanked on the 3' side by a poly(C) sequence and/or a histone stem-loop sequence. In addition or alternatively, the first poly(A) sequence is flanked on the 5' side by a 3'-UTR element derived from a, preferably human, albumin or globin gene, preferably albumin7 as defined herein.

In a preferred embodiment, the artificial nucleic acid molecule comprises at least two poly(A) sequences, which are separated from each other by a nucleotide sequence comprising or consisting of at least 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145 or 150 nucleotides, wherein the nucleotide sequence does preferably not comprise more than 10, 9, 8, 7, 6, 5, 4, 3 or 2 consecutive adenine nucleotides. Preferably, the nucleotide sequence, which separates the first and the second poly(A) sequence comprises from 1 to about 200 nucleotides, preferably from 10 to 90, from 20 to 85, from 30 to 80, from 40 to 80, from 50 to 75 or from 55 to 85 nucleotides, more preferably from 55 to 80 nucleotides, wherein the nucleotide sequence does preferably not comprise more than 10, 9, 8, 7, 6, 5, 4, 3 or 2 consecutive adenine nucleotides.

Preferably, the artificial nucleic acid molecule comprises a 3'-UTR comprising at least two poly(A) sequences, wherein the first and/or the second poly(A) sequence preferably comprises at least 60, 70, 80, 90, 100, 110, 120, 130, 140, 150, 160, 170, 180, 190, 200, 210, 220, 230, 240, 250, 300, 350, 400, 500, 600, 700, 800, 900, or 1000 adenine nucleotides, more preferably at least 150 adenine nucleotides, even more preferably at least 160 adenine nucleotides. In a preferred embodiment, the first poly(A) sequence comprises at least 20, 30, 40, 50, 60, 70, 80 or 90 adenine nucleotides. The first poly(A) sequence may further comprise from 20 to 90, from 25 to 85, from 35 to 80 or from 45 to 75, preferably from 60 to 70, adenine nucleotides. In a further preferred embodiment, the first poly(A) sequence comprises about 60 adenine nucleotides. In a particularly preferred embodiment, the first poly(A) sequence comprises or consists of about 64 adenine nucleotides. The second poly(A) sequence preferably comprises at least 60, 70, 80, 90, 100, 110, 120, 130, 140, 150, 160, 170, 180, 190, 200, 210, 220, 230, 240, 250, 300, 350, 400, 500, 600, 700, 800, 900, or 1000 adenine nucleotides, more preferably at least 150 adenine nucleotides, even more preferably at least 160 adenine nucleotides. In a particularly preferred embodiment, the second poly(A) sequence comprises about 160 adenine nucleotides. Alternatively, the second poly(A) sequence preferably comprises at least 300 adenine nucleotides, more preferably at least 350 adenine nucleotides, even more preferably at least 380 adenine nucleotides or at least 430 adenine nucleotides. In a preferred embodiment, the second poly(A) sequence comprises about 380 or about 430 adenine residues. Preferably, the number of adenine nucleotides comprised in the second poly(A) sequence is preferably from 110 to 200, from 120 to 200, from 130 to 190, from 140 to 180, or from 150 to 170. Alternatively, the number of adenine nucleotides comprised in the second poly(A) sequence is preferably from 320 to 450, from 330 to 420, from 340 to 410, from 350 to 400, from 360 to 400, or from 370 to 390. Further alternatively, the second poly(A) sequence preferably comprises at least 900 adenine nucleotides, more preferably at least 900, 950 or at least 1000 adenine nucleotides. Preferably, the number of adenine nucleotides comprised in the second poly(A) sequence is from 900 to 1100 or from 1000 to 1100 adenine nucleotides. In a particularly preferred embodiment, the second poly(A) sequence preferably comprises about 1000 adenine nucleotides.

In a preferred embodiment, the artificial nucleic acid molecule comprises a 3'-UTR comprising at least two poly (A) sequences, wherein the first poly(A) sequence is located at the 5' terminus of the 3'-UTR or located at a position within the 3'-UTR, i.e. flanked on the 5' and on the 3' side by other UTR-elements, and comprises at least 20, 30, 40, 50, 60, 70, 80 or 90 adenine nucleotides, preferably from 20 to 90, from 25 to 85, from 35 to 80 or from 45 to 75, preferably from 60 to 70, more preferably about 64, adenine nucleotides. In that embodiment, the second poly(A) sequence preferably comprises at least 60, 70, 80, 90, 100, 110, 120, 130, 140, 150, 160, 170, 180, 190, 200, 210, 220, 230, 240, 250, 300, 350, 400, 500, 600, 700, 800, 900, or 1000 adenine nucleotides, more preferably at least 150 adenine nucleotides, even more preferably at least 160 adenine nucleotides, preferably from 110 to 200, from 120 to 200, from 130 to 190, from 140 to 180, or from 150 to 170 adenine nucleotides. Therein, the second poly(A) sequence is preferably located 3' of the first poly(A) sequence, more preferably at the 3'-terminus of the 3'-UTR as defined herein, or even more preferably at the 3'-terminus of the inventive artificial nucleic acid molecule as defined herein, wherein the first and the second poly(A) sequences are preferably separated, more preferably separated as defined herein.

In a further preferred embodiment, the artificial nucleic acid molecule comprises a 3'-UTR comprising at least two poly(A) sequences, wherein the first poly(A) sequence is located at the 5' terminus of the 3'-UTR or located at a position within the 3'-UTR, i.e. flanked on the 5' and on the 3' side by other UTR-elements, and comprises at least 20, 30, 40, 50, 60, 70, 80 or 90 adenine nucleotides, preferably from 20 to 90, from 25 to 85, from 35 to 80 or from 45 to 75, preferably from 60 to 70, more preferably about 64, adenine nucleotides. In that embodiment, the second poly (A) sequence preferably comprises at least 60, 70, 80, 90, 100, 110, 120, 130, 140, 150, 160, 170, 180, 190, 200, 210, 220, 230, 240, 250, 300, 350, 400, 500, 600, 700, 800, 900, or 1000, more preferably 300 adenine nucleotides, further preferably at least 350 adenine nucleotides, even more preferably at least 380 adenine nucleotides, preferably from 320 to 430, from 330 to 420, from 340 to 410, from 350 to 400, from 360 to 400, or from 370 to 390 adenine nucleotides. Therein, the second poly(A) sequence is preferably located 3' of the first poly(A) sequence, more preferably at the 3'-end of the 3'-UTR of the inventive artificial nucleic acid molecule, wherein the first and the second poly(A) sequences are preferably separated, more preferably separated as defined herein.

In a further preferred embodiment, the artificial nucleic acid molecule comprises a 3'-UTR comprising at least two poly(A) sequences, wherein the first poly(A) sequence is located at the 5' terminus of the 3'-UTR or located at a position within the 3'-UTR, i.e. flanked on the 5' and on the 3' side by other UTR-elements, and comprises at least 20, 30, 40, 50, 60, 70, 80 or 90 adenine nucleotides, preferably from 20 to 90, from 25 to 85, from 35 to 80 or from 45 to 75, preferably from 60 to 70, more preferably about 64, adenine nucleotides. In that embodiment, the second poly (A) sequence preferably comprises at least 60, 70, 80, 90, 100, 110, 120, 130, 140, 150, 160, 170, 180, 190, 200, 210, 220, 230, 240, 250, 300, 350, 400, 500, 600, 700, 800, 900, or 1000, more preferably at least 900 adenine nucleotides, more preferably at least 900, at least 950 or at least 1000 adenine nucleotides. Preferably, the number of adenine nucleotides comprised in the second poly(A) sequence is from 900 to 1100 or from 1000 to 1100 adenine nucleotides. In a particularly preferred embodiment, the second poly(A) sequence preferably comprises about 1000 adenine nucleotides. Therein, the second poly(A) sequence is preferably located 3' of the first poly(A) sequence, more preferably at the 3'-end of the 3'-UTR of the inventive artificial nucleic acid molecule, wherein the first and the second poly(A) sequences are preferably separated, more preferably separated as defined herein.

An artificial nucleic acid molecule according to the invention, such as a DNA molecule comprising an ORF followed by a 3'-UTR, may contain at least one stretch of thymidine nucleotides, which corresponds to the at least one poly(A) sequence as defined herein and which can be transcribed into a poly(A) sequence as defined herein in the resulting mRNA.

For example, the artificial nucleic acid molecule according to the present invention may comprise a nucleic acid sequence corresponding to the DNA sequence (SEQ ID No. 1)
GTCCACCTGTCCCTCCTGGGCTGCTGGATTGTCTCGTTTTCCTGCCAA

ATAAACAGGATCAGCGCTTTACAGATCTAAAAAAAAAAAAAAAAAAAA

AAAAAAAAAAAAAAAAAAAAAAAAAAAAAAAAAAAAAAAAAAAA.

Transcription of such sequences may result in artificial nucleic acid molecules comprising the sequence (SEQ ID No. 2)
GUCCACCUGUCCCUCCUGGGCUGCUGGAUUGUCUCGUUUUCCUGCCAA

AUAAACAGGAUCAGCGCUUUACAGAUCUAAAAAAAAAAAAAAAAAAAA

AAAAAAAAAAAAAAAAAAAAAAAAAAAAAAAAAAAAAAAAAAAA.

Such artificial RNA molecules, i.e. artificial nucleic acid molecules comprising a sequence according to SEQ ID No. 2 may also be obtainable in vitro by common methods of chemical-synthesis without being necessarily transcribed from a DNA-progenitor.

Alternatively or in addition, multiple adenine nucleotides may be added to an artificial nucleic acid molecule according to the invention by any other technique known in the art, for example via chemical synthesis or via an adenylation reaction. Preferably, adenine nucleotides are added to an inventive artificial nucleic acid molecule as described herein by an enzymatic adenylation reaction. For instance, an inventive RNA molecule may be enzymatically polyadenylated by incubation with a suitable enzyme, such as E. coli poly(A) polymerase.

In one embodiment, the artificial nucleic acid molecule according to the invention comprises an ORF and a 3'-UTR, wherein the 3'-UTR comprises a polyadenylation signal. In the context of the present invention, the polyadenylation signal is located within the 3'-UTR, at the 3'-terminus of the 3'-UTR or downstream of the 3' terminus of the 3'-UTR element. Preferably, the polyadenylation signal as used herein is comprised by the 3'-UTR of the artificial nucleic acid molecule. Even more preferably, the polyadenylation signal is located at the 3' terminus of the 3'-UTR, i.e. the 3'-UTR does preferably not contain more than 12, 11, 10, 9, 8, 7, 6, 5, 4, 3, 2 or 1 nucleotides located 3' of said polyadenylation signal; more preferably the 3'-UTR does not contain further elements located 3' to said polyadenylation signal. In a preferred embodiment, the polyadenylation signal is located at the 3' terminus of the artificial nucleic acid molecule, i.e. the artificial nucleic acid molecule does preferably not contain more than 12, 11, 10, 9, 8, 7, 6, 5, 4, 3, 2 or 1 nucleotides located 3' of said poly(A) sequence.

In a preferred embodiment, the artificial nucleic acid molecule according to the invention comprises a 3'-UTR, which comprises at least one poly(A) sequence, preferably as defined herein, and a polyadenylation signal. Therein, the polyadenylation signal is preferably located 3' of the at least one poly(A) sequence comprised in the 3'-UTR, more preferably located 3' of the most 3' poly(A) sequence in the 3'-UTR. More preferably, the polyadenylation signal is located 3' of the at least one poly(A) signal, more preferably 3' of the most 3' poly(A) sequence, and is separated from the said poly(A) signal by a nucleotide sequence comprising or consisting of at least 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145 or 150 nucleotides, wherein the nucleotide sequence does preferably not comprise more than 10, 9, 8, 7, 6, 5, 4, 3 or 2 consecutive adenine nucleotides. Preferably, the nucleotide sequence, which separates the at least one poly(A) sequence and the polyadenylation signal comprises from 1 to about 200 nucleotides, preferably from 10 to 90, from 20 to 85, from 30 to 80, from 40 to 80, from 50 to 75 or from 55 to 85 nucleotides, more preferably from 55 to 80 nucleotides, wherein the nucleotide sequence does preferably not comprise more than 10, 9, 8, 7, 6, 5, 4, 3 or 2 consecutive adenine nucleotides.

In a preferred embodiment, the artificial nucleic acid molecule according to the invention comprises a 3'-UTR, which comprises at least two poly(A) sequences, preferably as defined herein, and a polyadenylation signal, wherein the polyadenylation is located 3' of the at least two poly(A) sequences, and wherein preferably each of the at least two poly(A) sequences and the polyadenylation signal is separated from another poly(A) sequence or from the polyadenylation signal, respectively, wherein the separating nucleotide sequences are as defined above. Therein, the polyadenylation signal is preferably located at the 3' terminus of the 3'-UTR as defined herein, more preferably at the 3' terminus of the artificial nucleic acid molecule as defined herein.

In one embodiment, the artificial nucleic acid molecule is a DNA molecule comprising a 3'-UTR comprising a polyadenylation signal, preferably as defined herein, wherein the DNA molecule further optionally comprises at least one poly(A) sequence, preferably as defined herein. Alternatively, the artificial nucleic acid molecule is an RNA molecule comprising a 3'-UTR comprising a polyadenylation signal, preferably as defined herein, wherein the RNA molecule optionally further comprises at least one poly(A) sequence, preferably as defined herein.

The polyadenylation signal preferably comprises the consensus sequence NN(U/T)ANA, with N=A or U, preferably AA(U/T)AAA or A(U/T)(U/T)AAA. Such consensus sequence may be recognised by most animal and bacterial cell-systems, for example by the polyadenylation-factors, such as cleavage/polyadenylation specificity factor (CPSF) cooperating with CstF, PAP, PAB2, CFI and/or CFII. Preferably, the polyadenylation signal, preferably the consensus sequence NNUANA, is located less than about 50 nucleotides, more preferably less than about 30 bases, most preferably less than about 25 bases, for example 21 bases, downstream of the 3'-end of the optional 3'-UTR element as defined herein. Further preferably, the polyadenylation signal, preferably the consensus sequence defined above, is located as described above.

Transcription of an artificial nucleic acid molecule according to the present invention, e.g. of an artificial DNA molecule comprising a polyadenylation signal downstream (i.e. in the 3' direction) of the 3'-UTR will result in a premature-RNA containing the polyadenylation signal downstream of its 3'-UTR.

Using an appropriate transcription system will then lead to the attachment of a poly(A) sequence to the premature-RNA. For example, the inventive artificial nucleic acid molecule may be a DNA molecule comprising a 3'-UTR as described herein comprising a polyadenylation signal, which may result in polyadenylation of an RNA upon transcription of this DNA molecule. Accordingly, a resulting RNA may comprise a 3'-UTR, which comprises at least one poly(A) sequence, and wherein the 3'-UTR is followed by an additional poly(A) sequence.

Potential transcription systems are in vitro transcription systems or cellular transcription systems etc. Accordingly, transcription of an artificial nucleic acid molecule according to the invention, e.g. transcription of an artificial nucleic acid molecule comprising an open reading frame, a 3'-UTR as defined herein comprising a polyadenylation-signal, may result in an mRNA molecule comprising an open reading frame, a 3'-UTR as defined herein comprising an additional poly(A) sequence.

The inventors have surprisingly found that the 3'-UTR comprising at least one poly(A) sequence as defined herein or a polyadenylation signal as defined herein results in an increased expression of the protein encoded by the ORF of the artificial nucleic acid molecule.

"Increased protein expression" or "enhanced protein expression" in the context of the present invention preferably means an increased/enhanced protein expression at one time point after initiation of expression or an increased/enhanced total amount of expressed protein compared to the expression induced by a reference nucleic acid molecule. Thus, the protein level observed at a certain time point after initiation of expression, e.g. after transfection, of the artificial nucleic acid molecule according to the present invention or after administration, e.g. by injection, of the artificial nucleic acid molecule to a tissue, e.g. after transfection or administration of an mRNA according to the present invention, for example, 6, 12, 24, 48 or 72 hours post transfection or administration, respectively, is preferably higher than the protein level observed at the same time point after initiation of expression, e.g. after transfection or administration, of a reference nucleic acid molecule, such as a reference mRNA comprising a reference 3'-UTR or lacking a 3'-UTR. In a preferred embodiment, the maximum amount of protein (as determined e.g. by protein activity or mass) expressed from the artificial nucleic acid molecule is increased with respect to the protein amount expressed from a reference nucleic acid comprising a reference 3'-UTR or lacking a 3'-UTR. Peak expression levels are preferably reached within 48 hours, more preferably within 24 hours and even more preferably within 12 hours after, for instance, transfection or administration to a tissue.

Preferably, the total protein production from an artificial nucleic acid molecule according to the invention is increased or enhanced with respect to a reference nucleic acid. In particular, protein production is preferably increased or enhanced over the time span, in which protein is produced from an artificial nucleic acid molecule, preferably in a target tissue or in a mammalian expression system, such as in mammalian cells, e.g. in HeLa or HDF cells in comparison to a reference nucleic acid molecule lacking a 3'-UTR or comprising a reference 3'-UTR. According to a preferred embodiment, the cumulative amount of protein expressed over time is increased when using the artificial nucleic acid molecule according to the invention.

The artificial nucleic acid molecule according to the invention is preferably characterized by increased expression of the encoded protein in comparison to a respective nucleic acid molecule lacking the at least one 3'-UTR element or comprising a reference 3'-UTR ("reference nucleic acid") comprising a nucleic acid sequence which is derived from the 3'-UTR of a ribosomal protein gene or from a variant of the 3'-UTR of a ribosomal protein gene In order to assess the in vivo protein production by the inventive artificial nucleic acid molecule, the expression of the encoded protein is determined following injection/transfection of the inventive artificial nucleic acid molecule into target cells/tissue and compared to the protein expression induced by the reference nucleic acid. Quantitative methods for determining protein expression are known in the art (e.g. Western-Blot, FACS, ELISA, mass spectometry). Particularly useful in this context is the determination of the expression of reporter proteins like luciferase, Green fluorescent protein (GFP), or secreted alkaline phosphatase (SEAP). Thus, an artificial nucleic acid according to the invention or a reference nucleic acid is introduced into the target tissue or cell, e.g. via transfection or injection. Several hours or several days (e.g. 6, 12, 24, 48 or 72 hours) post initiation of expression or post introduction of the nucleic acid molecule, a target cell sample is collected and measured via FACS and/or lysed. Afterwards the lysates can be used to detect the expressed protein (and thus determine the efficiency of protein expression) using several methods, e.g. Western-Blot, FACS, ELISA, mass spectrometry or by fluorescence or luminescence measurement.

Therefore, if the protein expression from an artificial nucleic acid molecule according to the invention is compared to the protein expression from a reference nucleic acid molecule at a specific time point (e.g. 6, 12, 24, 48 or 72 hours post initiation of expression or post introduction of the nucleic acid molecule), both nucleic acid molecules are introduced separately into target tissue/cells, a sample from the tissue/cells is collected after a specific time point, protein lysates are prepared according to the particular protocol adjusted to the particular detection method (e.g. Western Blot, ELISA, etc. as known in the art) and the protein is detected by the chosen detection method. As an alternative to the measurement of expressed protein amounts in cell lysates—or, in addition to the measurement of protein amounts in cell lysates prior to lysis of the collected cells or using an aliquot in parallel—protein amounts may also be determined by using FACS analysis.

If the total amount of protein for a specific time period is to be measured, tissue or cells can be collected after several time points after introduction of the artificial nucleic acid molecule (e.g. 6, 12, 24, 48 and 72 hours post initiation of expression or post introduction of the nucleic acid molecule; usually from different test animals), and the protein amount per time point can be determined as explained above. In order to calculate the cumulative protein amount, a mathematical method of determining the total amount of protein can be used, e.g. the area under the curve (AUC) can be determined according to the following formula:

$$AUC = \int_a^b f(x)d(x)$$

In order to calculate the area under the curve for total amount of protein, the integral of the equation of the expression curve from each end point (a and b) is calculated.

Thus, "total protein production" preferably refers to the area under the curve (AUC) representing protein production over time.

Preferably, the nucleic acid molecule according to the invention comprises a 3'-UTR comprising at least one poly (A) sequence as defined herein, which optionally further comprises at least one further 3'-UTR element, which is distinct from a poly(A) sequence.

Therein, the at least one further 3'-UTR element preferably increases protein expression from said artificial nucleic acid molecule.

In this context, the term "3'-UTR element" typically refers to an optional element of the 3'-UTR of the artificial nucleic acid molecule according to the invention, wherein the 3'-UTR element is a nucleic acid sequence that is distinct from a poly(A) sequence, i.e. is not a poly(A) sequence. In particular, the term refers to a nucleic acid sequence, which comprises or consists of a nucleic acid sequence that is derived from a 3'-UTR or from a variant of a 3'-UTR. A "3'-UTR element" preferably refers to a nucleic acid sequence, which represents a 3'-UTR—or a part thereof—of an artificial nucleic acid sequence, such as an artificial mRNA, or which codes for a 3'-UTR of an artificial nucleic acid molecule. Accordingly, in the sense of the present invention, preferably, a 3'-UTR element may be the 3'-UTR of an mRNA, preferably of an artificial mRNA, or it may be the transcription template for a 3'-UTR of an mRNA. Thus, a 3'-UTR element preferably is a nucleic acid sequence, which corresponds to the 3'-UTR of an mRNA, preferably to the 3'-UTR of an artificial mRNA, such as an mRNA obtained by transcription of a genetically engineered vector construct. Preferably, a 3'-UTR element in the sense of the present invention functions as a 3'-UTR or codes for a nucleotide sequence that fulfils the function of a 3'-UTR.

Preferably, the at least one open reading frame and the 3'-UTR are heterologous. The term "heterologous" in this context means that the open reading frame and the 3'-UTR or the 3'-UTR element are not occurring naturally (in nature) in this combination. Preferably, the 3'-UTR or the 3'-UTR element is derived from a different gene than the open reading frame. For example, the ORF may be derived from a different gene than the 3'-UTR, e.g. encoding a different protein or the same protein but of a different species etc. Preferably, the open reading frame does not code for a ribosomal protein. In specific embodiments it is preferred that the open reading frame does not code for a reporter protein, e.g., selected from the group consisting of globin proteins (particularly beta-globin), luciferase protein, GFP proteins or variants thereof, for example, variants exhibiting at least 70% sequence identity to a globin protein, a luciferase protein, or a GFP protein.

Preferably, the at least one 3'-UTR is functionally linked to the ORF. This means preferably that the 3'-UTR is associated with the ORF such that it may exert a function, such as an increasing, enhancing or stabilizing function on the expression of the encoded peptide or protein or a stabilizing function on the artificial nucleic acid molecule. Preferably, the ORF and the 3'-UTR are associated in 5'-3' direction. Thus, preferably, the artificial nucleic acid molecule comprises the structure 5'-ORF-(optional)-linker-3'-UTR-3', wherein the linker may be present or absent. For example, the linker may be one or more nucleotides, such as a stretch of 1 to 50 or 1 to 20 nucleotides, e.g., comprising or consisting of one or more restriction enzyme recognition sites (restriction sites).

In one embodiment, the 3'-UTR of the inventive artificial nucleic acid molecule optionally comprises a 3'-UTR element, which may be derivable from a gene that relates to an mRNA with an enhanced half-life (that provides a stable mRNA), for example, a 3'UTR element as defined and described below.

In a particularly preferred embodiment, the optional 3'-UTR element comprises or consists of a nucleic acid sequence, which is derived from a 3'-UTR of a gene selected from the group consisting of an albumin gene, an α-globin gene, a β-globin gene, a ribosomal protein gene, a tyrosine hydroxylase gene, a lipoxygenase gene, and a collagen alpha gene, such as a collagen alpha 1(I) gene, or from a variant of a 3'-UTR of a gene selected from the group consisting of an albumin gene, an α-globin gene, a β-globin gene, a ribosomal protein gene, a tyrosine hydroxylase gene, a lipoxygenase gene, and a collagen alpha gene, such as a collagen alpha 1(I) gene according to SEQ ID No. 1369-1390 of the patent application WO2013/143700, whose disclosure is incorporated herein by reference. In a particularly preferred embodiment, the 3'-UTR element comprises or consists of a nucleic acid sequence, which is derived from a 3'UTR of an albumin gene, preferably a vertebrate albumin gene, more preferably a mammalian albumin gene, most preferably a human albumin gene according to SEQ ID No. 3

```
Human albumin 3'-UTR SEQ ID No. 3:
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT
(corresponding to SEQ ID No: 1369 of the
patent application WO2013/143700).
```

In this context, it is particularly preferred that the 3'-UTR of the inventive artificial nucleic acid molecule optionally comprises a 3'-UTR element comprising a corresponding RNA sequence derived from the nucleic acids according to SEQ ID No. 1369-1390 of the patent application WO2013/143700 or a fragment, homolog or variant thereof.

Most preferably, the optional 3'-UTR element comprises the nucleic acid sequence derived from a fragment of the human albumin gene according to SEQ ID No. 4:

```
albumin7 3'UTR
CATCACATTTAAAAGCATCTCAGCCTACCATGAGAATAAGAGAAAGAA

AATGAAGATCAATAGCTTATTCATCTCTTTTTCTTTTTCGTTGGTGTA

AAGCCAACACCCTGTCTAAAAAACATAAATTTCTTTAATCATTTTGCC

TCTTTTCTCTGTGCTTCAATTAATAAAAAATGGAAAGAACCT
(SEQ ID No. 4 corresponding to SEQ ID No: 1376
of the patent application WO2013/143700)
```

In this context, it is particularly preferred that the optional 3'-UTR element of the inventive artificial nucleic acid molecule comprises or consists of a corresponding RNA sequence of the nucleic acid sequence according to SEQ ID No. 4.

In another particularly preferred embodiment, the 3'UTR element comprises or consists of a nucleic acid sequence, which is derived from a 3'UTR of an α-globin gene, preferably a vertebrate α- or β-globin gene, more preferably a mammalian α- or β-globin gene, most preferably a human α- or β-globin gene according to SEQ ID No. 5-7:

3'-UTR of *Homo sapiens* hemoglobin, alpha 1 (HBA1)
```
GCTGGAGCCTCGGTGGCCATGCTTCTTGCCCCTTGGGCCTCCCCCCAG

CCCCTCCTCCCCTTCCTGCACCCGTACCCCCGTGGTCTTTGAATAAAG

TCTGAGTGGGCGGC
```
(SEQ ID No: 5 corresponding to SEQ ID No. 1370 of the patent application WO2013/143700)

3'-UTR of *Homo sapiens* hemoglobin, alpha 2 (HBA2)
```
GCTGGAGCCTCGGTAGCCGTTCCTCCTGCCCGCTGGGCCTCCCAACGG

GCCCTCCTCCCCTCCTTGCACCGGCCCTTCCTGGTCTTTGAATAAAGT

CTGAGTGGGCAG
```
(SEQ ID No: 6 corresponding to SEQ ID No. 1371 of the patent application WO2013/143700)

3'-UTR of *Homo sapiens* hemoglobin, beta (HBB)
```
GCTCGCTTTCTTGCTGTCCAATTTCTATTAAAGGTTCCTTTGTTCCCT

AAGTCCAACTACTAAACTGGGGGATATTATGAAGGGCCTTGAGCATCT

GGATTCTGCCTAATAAAAAACATTTATTTTCATTGC
```
(SEQ ID No: 7 corresponding to SEQ ID No. 1372 of the patent application WO2013/143700).

For example, the optional 3'UTR element may comprise or consist of the center, α-complex-binding portion of the 3'UTR of an α-globin gene, such as of a human α-globin gene, preferably according to SEQ ID No. 8:

Center, α-complex-binding portion of the 3'UTR of an α-globin gene (also named herein as "muag")

```
GCCCGATGGGCCTCCCAACGGGCCCTCCTCCCCTCCTTGCACCG
```
(SEQ ID NO. 8 corresponding to SEQ ID No. 1393 of the patent application WO2013/143700).

In this context, it is particularly preferred that the 3'-UTR element of the inventive mRNA comprises or consists of a corresponding RNA sequence of the nucleic acid sequence according to SEQ ID No. 8 or a homolog, a fragment or variant thereof.

In a preferred embodiment, the (optional) at least one 3'-UTR element comprises a nucleic acid sequence, which is derived from the 3'-UTR of a eukaryotic ribosomal protein gene, preferably from the 3'-UTR of a vertebrate ribosomal protein gene, more preferably from the 3'-UTR of a mammalian ribosomal protein gene, even more preferably from the 3'-UTR of a primate ribosomal protein gene, in particular of a human ribosomal protein gene.

In a preferred embodiment, the optional 3'-UTR element comprises or corresponds to a nucleic acid sequence, which is derived from the 3'-UTR sequence of a transcript selected from the group consisting of NM_000661.4, NM_001024921.2, NM_000967.3, NM_001033853.1, NM_000968.3, NM_000969.3, NM_001024662.1, NM_000970.3, NM_000971.3, NM_000972.2, NM_000975.3, NM_001199802.1, NM_000976.3, NM_000977.3, NM_033251.2, NM_001243130.1, NM_001243131, NM_000978.3, NM_000979.3, NM_001270490.1, NM_000980.3, NM_000981.3, NM_000982.3, NM_000983.3, NM_000984.5, NM_000985.4, NM_001035006.2, NM_001199340.1, NM_001199341.1, NM_001199342.1, NM_001199343.1, NM_001199344.1, NM_001199345.1, NM_000986.3, NM_000987.3, NM_000988.3, NM_000989.3, NM_000990.4, NM_001136134.1, NM_000991.4, NM_001136135.1, NM_001136136.1, NM_001136137.1, NM_000992.2, NM_000993.4, NM_001098577.2, NM_001099693.1, NM_000994.3, NM_001007073.1, NM_001007074.1, NM_000996.2, NM_000997.4, NM_000998.4, NM_000999.3, NM_001035258.1, NM_001000.3, NM_001002.3, NM_053275.3, NM_001003.2, NM_213725.1, NM_001004.3, NM_001005.4, NM_001256802.1, NM_001260506.1, NM_001260507.1, NM_001006.4, NM_001267699.1, NM_001007.4, NM_001008.3, NM_001009.3, NM_001010.2, NM_001011.3, NM_001012.1, NM_001013.3, NM_001203245.2, NM_001014.4, NM_001204091.1, NM_001015.4, NM_001016.3, NM_001017.2, NM_001018.3, NM_001030009.1, NM_001019.4, NM_001020.4, NM_001022.3, NM_001146227.1, NM_001023.3, NM_001024.3, NM_001025.4, NM_001028.2, NM_001029.3, NM_001030.4, NM_002954, NM_001135592.2, NM_001177413.1, NM_001031.4, NM_001032.4, NM_001030001.2, NM_002948.3, NM_001253379.1, NM_001253380.1, NM_001253382.1, NM_001253383.1, NM_001253384.1, NM_002952.3, NM_001034996.2, NM_001025071.1, NM_001025070.1, NM_005617.3, NM_006013.3, NM_001256577.1, NM_001256580.1, NM_007104.4, NM_007209.3, NM_012423.3, NM_001270491.1, NM_033643.2, NM_015414.3, NM_021029.5, NM_001199972.1, NM_021104.1, NM_022551.2, NM_033022.3, NM_001142284.1, NM_001026.4, NM_001142285.1, NM_001142283.1, NM_001142282.1, NM_000973.3, NM_033301.1, NM_000995.3, NM_033625.2, NM_001021.3, NM_002295.4, NM_001012321.1, NM_001033930.1, NM_003333.3, NM_001997.4, NM_001099645.1, NM_001021.3, NM_052969.1, NM_080746.2, NM_001001.4, NM_005061.2, NM_015920.3, NM_016093.2, NM_198486.2, NG_011172.1, NG_011253.1, NG_000952.4, NR_002309.1, NG_010827.2, NG_009952.2, NG_009517.1

In a preferred embodiment, the 3'-UTR element of the artificial nucleic acid molecule according to the present invention is derived from the 3'-UTR region of a gene encoding a ribosomal protein, preferably from the 3'-UTR region of ribosomal protein L9 (RPL9), ribosomal protein L3 (RPL3), ribosomal protein L4 (RPL4), ribosomal protein L5 (RPL5), ribosomal protein L6 (RPL6), ribosomal protein L7 (RPL7), ribosomal protein L7a (RPL7A), ribosomal protein L11 (RPL11), ribosomal protein L12 (RPL12), ribosomal protein L13 (RPL13), ribosomal protein L23 (RPL23), ribosomal protein L18 (RPL18), ribosomal protein L18a (RPL18A), ribosomal protein L19 (RPL19), ribosomal protein L21 (RPL21), ribosomal protein L22 (RPL22), ribosomal protein L23a (RPL23A), ribosomal protein L17 (RPL17), ribosomal protein L24 (RPL24), ribosomal protein L26 (RPL26), ribosomal protein L27 (RPL27), ribosomal protein L30 (RPL30), ribosomal protein L27a (RPL27A), ribosomal protein L28 (RPL28), ribosomal protein L29 (RPL29), ribosomal protein L31 (RPL31), ribosomal protein L32 (RPL32), ribosomal protein L35a (RPL35A), ribosomal protein L37 (RPL37), ribosomal protein L37a (RPL37A), ribosomal protein L38 (RPL38), ribosomal protein L39 (RPL39), ribosomal protein, large, P0 (RPLP0), ribosomal protein, large, P1 (RPLP1), ribosomal protein, large, P2 (RPLP2), ribosomal protein S3 (RPS3), ribosomal protein S3A (RPS3A), ribosomal protein S4, X-linked (RPS4X), ribosomal protein S4, Y-linked 1 (RPS4Y1), ribosomal protein S5 (RPS5), ribosomal protein S6 (RPS6), ribosomal protein S7 (RPS7), ribosomal protein S8 (RPS8), ribosomal protein S9 (RPS9), ribosomal protein S10 (RPS10), ribosomal protein S11 (RPS11), ribosomal protein S12 (RPS12), ribosomal protein S13 (RPS13), ribosomal protein S15

(RPS15), ribosomal protein S15a (RPS15A), ribosomal protein S16 (RPS16), ribosomal protein S19 (RPS19), ribosomal protein S20 (RPS20), ribosomal protein S21 (RPS21), ribosomal protein S23 (RPS23), ribosomal protein S25 (RPS25), ribosomal protein S26 (RPS26), ribosomal protein S27 (RPS27), ribosomal protein S27a (RPS27a), ribosomal protein S28 (RPS28), ribosomal protein S29 (RPS29), ribosomal protein L15 (RPL15), ribosomal protein S2 (RPS2), ribosomal protein L14 (RPL14), ribosomal protein S14 (RPS14), ribosomal protein L10 (RPL10), ribosomal protein L10a (RPL10A), ribosomal protein L35 (RPL35), ribosomal protein L13a (RPL13A), ribosomal protein L36 (RPL36), ribosomal protein L36a (RPL36A), ribosomal protein L41 (RPL41), ribosomal protein S18 (RPS18), ribosomal protein S24 (RPS24), ribosomal protein L8 (RPL8), ribosomal protein L34 (RPL34), ribosomal protein S17 (RPS17), ribosomal protein SA (RPSA) or ribosomal protein S17 (RPS17). In an alternative embodiment, the 3'-UTR element may be derived from a gene encoding a ribosomal protein or from a gene selected from ubiquitin A-52 residue ribosomal protein fusion product 1 (UBA52), Finkel-Biskis-Reilly murine sarcoma virus (FBR-MuSV) ubiquitously expressed (FAU), ribosomal protein L22-like 1 (RPL22L1), ribosomal protein L39-like (RPL39L), ribosomal protein L10-like (RPL10L), ribosomal protein L36a-like (RPL36AL), ribosomal protein L3-like (RPL3L), ribosomal protein S27-like (RPS27L), ribosomal protein L26-like 1 (RPL26L1), ribosomal protein L7-like 1 (RPL7L1), ribosomal protein L13a pseudogene (RPL13AP), ribosomal protein L37a pseudogene 8 (RPL37AP8), ribosomal protein S10 pseudogene 5 (RPS10P5), ribosomal protein S26 pseudogene 11 (RPS26P11), ribosomal protein L39 pseudogene 5 (RPL39P5), ribosomal protein, large, P0 pseudogene 6 (RPLP0P6) and ribosomal protein L36 pseudogene 14 (RPL36P14).

Preferably, the at least one 3'-UTR element of the artificial nucleic acid molecule according to the present invention comprises or consists of a nucleic acid sequence which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of a 3'-UTR of a ribosomal protein gene, such as to the nucleic acid sequences according to SEQ ID NOs:10 to 115 as defined in international patent application PCT/EP2013/003946, or the corresponding RNA sequence.

In a preferred embodiment, the (optional) at least one 3'-UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the 3'-UTR sequence of ribosomal protein Small 9 (RPS9). Most preferably, the (optional) at least one 3'-UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to SEQ ID NO: 9 or SEQ ID NO: 10

```
                                        SEQ ID NO: 9
GTCCACCTGTCCCTCCTGGGCTGCTGGATTGTCTCGTTTTCCTGC
CAAATAAACAGGATCAGCGCTTTAC

SEQ ID NO: 10
GUCCACCUGUCCCUCCUGGGCUGCUGGAUUGUCUCGUUUUCCUGC
CAAAUAAACAGGAUCAGCGCUUUAC
```

The term 'a nucleic acid sequence, which is derived from the 3'UTR of a [ . . . ] gene' preferably refers to a nucleic acid sequence, which is based on the 3'UTR sequence of a [ . . . ] gene or on a part thereof, such as on the 3'UTR of an albumin gene, an α-globin gene, a β-globin gene, a ribosomal protein gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, ribosomal protein gene, tyrosine hydroxylase gene, lipoxygenase gene, or collagen alpha gene, such as a collagen alpha 1(I) gene, preferably of an albumin gene.

The phrase "nucleic acid sequence, which is derived from the 3'UTR of a [ . . . ] gene" preferably refers to a nucleic acid sequence, which is based on the 3'-UTR sequence of a [ . . . ] gene, preferably a gene described above, or on a fragment or part thereof. This phrase includes sequences corresponding to the entire 3'-UTR sequence, i.e. the full length 3'-UTR sequence of said gene, and sequences corresponding to a fragment of the 3'-UTR sequence of said gene. Preferably, a fragment of a 3'-UTR of a [ . . . ] gene consists of a continuous stretch of nucleotides corresponding to a continuous stretch of nucleotides in the full-length 3'-UTR of a [ . . . ] gene, which represents at least 5%, 10%, 20%, preferably at least 30%, more preferably at least 40%, more preferably at least 50%, even more preferably at least 60%, even more preferably at least 70%, even more preferably at least 80%, and most preferably at least 90% of the full-length 3'-UTR of a [ . . . ] gene. Such a fragment, in the sense of the present invention, is preferably a functional fragment as described herein. Preferably, the fragment retains a regulatory function for the translation of the ORF linked to the 3'-UTR or fragment thereof. The term "3'-UTR of a [ . . . ] gene" preferably refers to the 3'-UTR of a naturally occurring gene, preferably as described herein.

The terms "variant of the 3'-UTR of a [ . . . ] gene" and "variant thereof", in that context, refers to a variant of the 3'-UTR of a naturally occurring gene. Such variant may be a modified 3'-UTR of said gene. For example, a variant 3'-UTR may exhibit one or more nucleotide deletions, insertions, additions and/or substitutions compared to the naturally occurring 3'-UTR, from which the variant is derived. Preferably, a variant of a 3'-UTR of a gene as used herein is at least 40%, preferably at least 50%, more preferably at least 60%, more preferably at least 70%, even more preferably at least 80%, even more preferably at least 90%, most preferably at least 95% identical to the naturally occurring 3'-UTR the variant is derived from. Preferably, the variant is a functional variant as described herein.

The terms "functional variant", "functional fragment", and "functional fragment of a variant" (also termed "functional variant fragment") in the context of the present invention, mean that the fragment of the 3'-UTR of a gene, the variant of the 3'-UTR of a gene, or the fragment of a variant of the 3'-UTR of a gene fulfils at least one, preferably more than one, function of the naturally occurring 3'-UTR of the respective gene, of which the variant, the fragment, or the fragment of a variant is derived. Such function may be, for example, stabilizing mRNA and/or enhancing, stabilizing and/or prolonging protein production from an mRNA and/or increasing protein expression or total protein production from an mRNA, preferably in a mammalian cell, such as in a human cell. Preferably, the function of the 3'-UTR of a gene as described herein concerns the translation of the protein encoded by the ORF. More preferably, the function comprises enhancing translation efficiency of the ORF linked to the 3'-UTR or fragment or variant thereof. It is particularly preferred that the variant, the fragment, and the variant fragment in the context of the present invention fulfil the function of stabilizing an mRNA, preferably in a mammalian cell, such as a human cell, compared to an mRNA comprising a reference 3'-UTR or lacking a 3'-UTR, and/or the function of enhancing, stabilizing and/or prolonging protein production from an mRNA, preferably in a mammalian cell, such as in a human cell, compared to an mRNA comprising a reference 3'-UTR or lacking a 3'-UTR, and/or the function of increasing protein production from an mRNA, preferably in a mammalian cell, such as in a human cell, compared to an mRNA comprising a reference 3'-UTR or lacking a 3'-UTR. A reference 3'-UTR may be, for example, a 3'-UTR naturally occurring in combination with the ORF. Furthermore, a functional variant, a functional fragment, or a functional variant fragment of a 3'-UTR of a gene as described herein preferably does not have a substantially diminishing effect on the efficiency of translation of the mRNA, which comprises such variant, fragment, or variant fragment of a 3'-UTR compared to the wild type 3'-UTR, from which the variant, the fragment, or the variant fragment is derived. A particularly preferred function of a "functional fragment", a "functional variant" or a "functional fragment of a variant" of the 3'-UTR of a gene in the context of the present invention is the increase, enhancement, stabilization and/or prolongation of protein production by expression of an mRNA carrying the functional fragment, functional variant or functional fragment of a variant as described above.

Preferably, the efficiency of the one or more functions exerted by the functional variant, the functional fragment, or the functional variant fragment, such as mRNA and/or protein production stabilizing efficiency and/or the protein production increasing efficiency, is increased by at least 5%, more preferably by at least 10%, more preferably by at least 20%, more preferably by at least 30%, more preferably by at least 40%, more preferably by at least 50%, more preferably by at least 60%, even more preferably by at least 70%, even more preferably by at least 80%, most preferably by at least 90% with respect to the mRNA and/or protein production stabilizing efficiency and/or the protein production increasing efficiency exhibited by the naturally occurring 3'-UTR of the respective gene, from which the variant, the fragment or the variant fragment is derived.

In the context of the present invention, a fragment of the 3'-UTR of a gene as described herein or of a variant of the 3'-UTR of such a gene preferably exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. Preferably, such fragment of the 3'-UTR of a gene or of a variant of the 3'-UTR of a gene is a functional fragment as described above. In a preferred embodiment, the 3'-UTR of a gene or a fragment or variant thereof exhibits a length of between 3 and about 500 nucleotides, preferably of between 5 and about 150 nucleotides, more preferably of between 10 and 100 nucleotides, even more preferably of between 15 and 90, most preferably of between 20 and 70.

Preferably, the at least one 3'-UTR element of the artificial nucleic acid molecule according to the present invention comprises or consists of a "functional fragment", a "functional variant" or a "functional fragment of a variant" of the 3'-UTR of a gene as described herein.

In a preferred embodiment, the at least one further 3'-UTR element, which may optionally be comprised in the 3'-UTR of the artificial nucleic acid molecule and which is distinct from a poly(A) sequence, increases the stability of the artificial nucleic acid molecule, e.g. increases the stability of an mRNA according to the present invention, compared to a respective nucleic acid (reference nucleic acid) lacking a 3'-UTR or comprising a reference 3'-UTR lacking the optional 3'-UTR element, such as a 3'-UTR naturally occurring in combination with the ORF. Preferably, the at least one 3'-UTR element of the artificial nucleic acid molecule according to the present invention increases the stability of protein production from the artificial nucleic acid molecule according to the present invention, e.g. from an mRNA according to the present invention, compared to a respective nucleic acid lacking a 3'-UTR or comprising a reference 3'-UTR, such as a 3'-UTR naturally occurring in combination with the ORF. Preferably, the at least one 3'-UTR element of the artificial nucleic acid molecule according to the present invention prolongs protein production from the artificial nucleic acid molecule according to the present invention, e.g. from an mRNA according to the present invention, compared to a respective nucleic acid lacking a 3'-UTR or comprising a reference 3'-UTR, such as a 3'-UTR naturally occurring in combination with the ORF. Preferably, the at least one 3'-UTR element of the artificial nucleic acid molecule according to the present invention increases the protein expression and/or total protein production from the artificial nucleic acid molecule according to the present invention, e.g. from an mRNA according to the present invention, compared to a respective nucleic acid lacking a 3'-UTR or comprising a reference 3'-UTR, such as a 3'-UTR naturally occurring in combination with the ORF. Preferably, the at least one 3'-UTR element of the artificial nucleic acid molecule according to the present invention does not negatively influence translational efficiency of a nucleic acid compared to the translational efficiency of a respective nucleic acid lacking a 3'-UTR or comprising a reference 3'-UTR, such as a 3'-UTR naturally occurring in combination with the ORF. Even more preferably, the translation efficiency is enhanced by the 3'-UTR in comparison to the translation efficiency of the protein encoded by the respective ORF in its natural context.

The term "respective nucleic acid molecule" or "reference nucleic acid molecule", in this context, means that—apart from the different 3'-UTRs—the reference nucleic acid molecule is comparable, preferably identical, to the inventive artificial nucleic acid molecule comprising the 3'-UTR element. In particular, a reference nucleic acid molecule may comprise a nucleotide sequence and elements, such as ORF and 3'-UTR, which differs from the inventive artificial nucleic acid molecule only in the optional at least one 3'-UTR element, which is distinct from a poly(A) sequence.

The term "stabilizing and/or prolonging protein production" from an artificial nucleic acid molecule such as an artificial mRNA preferably means that the protein production from the artificial nucleic acid molecule such as the artificial mRNA is stabilized and/or prolonged compared to the protein production from a reference nucleic acid molecule such as a reference mRNA, e.g. comprising a reference 3'-UTR lacking the 3'-UTR element or lacking a 3'-UTR altogether, preferably in a mammalian expression system, such as in HeLa or HDF cells. Thus, protein produced from the artificial nucleic acid molecule, such as the artificial mRNA, is observable for a longer period of time than what may be seen for a protein produced from a reference nucleic acid molecule. In other words, the amount of protein produced from the artificial nucleic acid molecule such as the artificial mRNA measured over time undercuts a threshold value at a later time point than the amount of protein produced from a reference nucleic acid molecule such as a reference mRNA measured over time. Such a threshold value may be, for example, the amount of protein measured in the initial phase of expression, such as 1, 2, 3, 4, 5 or 6 hours post initiation of expression, such as post transfection of the nucleic acid molecule.

For example, the protein production from the artificial nucleic acid molecule, such as an artificial mRNA,—in an amount which is at least the amount observed in the initial phase of expression, such as 1, 2, 3, 4, 5, or 6 hours post initiation of expression, such as post transfection of the nucleic acid molecule—is prolonged by at least about 5 hours, preferably by at least about 10 hours, more preferably by at least about 24 hours compared to the protein production from a reference nucleic acid molecule, such as a reference mRNA, in a mammalian expression system, such as in mammalian cells, e.g. in HeLa or HDF cells. Thus, the artificial nucleic acid molecule according to the present invention preferably allows for prolonged protein production in an amount, which is at least the amount observed in the initial phase of expression, such as 1, 2, 3, 4, 5, or 6 hours post initiation of expression, such as post transfection, by at least about 5 hours, preferably by at least about 10 hours, more preferably by at least about 24 hours compared to a reference nucleic acid molecule lacking a 3'-UTR or comprising a reference 3'-UTR lacking the 3'-UTR element.

In preferred embodiments, the period of protein production from the artificial nucleic acid molecule according to the present invention is extended at least 1.5 fold, preferably at least 2 fold, more preferably at least 2.5 fold compared to the protein production from a reference nucleic acid molecule lacking a 3'-UTR or comprising a reference 3'-UTR lacking the 3'-UTR element.

This effect of prolonging protein production may be determined by (i) measuring protein amounts, e.g. obtained by expression of an encoded reporter protein such as luciferase, preferably in a mammalian expression system such as in HeLa or HDF cells, over time, (ii) determining the time point, at which the protein amount undercuts the amount of protein observed, e.g., at 1, 2, 3, 4, 5, or 6 hours post initiation of expression, e.g. 1, 2, 3, 4, 5, or 6 hours post transfection of the artificial nucleic acid molecule, and (iii) comparing the time point, at which the protein amount undercuts the protein amount observed at 1, 2, 3, 4, 5, or 6 hours post initiation of expression to said time point determined for a nucleic acid molecule lacking a 3'-UTR or comprising a reference 3'-UTR lacking the 3'-UTR element.

Preferably, this stabilizing and/or prolonging effect on protein production is achieved, while the total amount of protein produced from the artificial nucleic acid molecule according to the present invention, e.g. within a time span of 48 or 72 hours, is at least the amount of protein produced from a reference nucleic acid molecule lacking a 3'-UTR or comprising a reference 3'-UTR lacking the 3'-UTR element, such as a 3'-UTR naturally occurring with the ORF of the artificial nucleic acid molecule. Thus, the present invention provides an artificial nucleic acid molecule, which allows for prolonged and/or stabilized protein production in a mammalian expression system, such as in mammalian cells, e.g. in HeLa or HDF cells, as specified above, wherein the total amount of protein produced from said artificial nucleic acid molecule, e.g. within a time span of 48 or 72 hours, is at least the total amount of protein produced, e.g. within said time span, from a reference nucleic acid molecule lacking a 3'-UTR or comprising a reference 3'-UTR, such as a 3'-UTR naturally occurring with the ORF of the artificial nucleic acid molecule.

Thus, "stabilized protein expression" preferably means that there is more uniform protein production from the artificial nucleic acid molecule according to the present invention over a predetermined period of time, such as over 24 hours, more preferably over 48 hours, even more preferably over 72 hours, when compared to a reference nucleic acid molecule, for example, an mRNA comprising a reference 3'-UTR lacking the 3'-UTR element or lacking a 3'-UTR altogether. Accordingly, the level of protein production, e.g. in a mammalian system, from the artificial nucleic acid molecule comprising a 3'-UTR element according to the present invention, e.g. from an mRNA according to the present invention, preferably does not drop to the extent observed for a reference nucleic acid molecule, such as a reference mRNA as described above. For example, the amount of a protein (encoded by the ORF) observed 6 hours after initiation of expression, e.g. 6 hours post transfection of the artificial nucleic acid molecule according to the present invention into a cell, such as a mammalian cell, may be comparable to the amount of protein observed 48 hours after initiation of expression, e.g. 48 hours post transfection. Thus, the ratio of the amount of protein encoded by the ORF, such as of a reporter protein, e.g., luciferase, observed at 48 hours post initiation of expression, e.g. 48 hours post transfection, to the amount of protein observed 6 hours after initiation of expression, e.g. 6 hours post transfection, is preferably at least about 0.4, more preferably at least about 0.5, more preferably at least about 0.6, even more preferably at least about 0.7. Preferably, the ratio is between about 0.4 and about 4, preferably between about 0.65 and about 3, more preferably between about 0.7 and 2 for a nucleic acid molecule according to the present invention. For a respective reference nucleic acid molecule, e.g. an mRNA comprising a reference 3'-UTR lacking the 3'-UTR element or lacking a 3'-UTR altogether, said ratio may be, e.g. between about 0.05 and about 0.3.

Thus, in a preferred embodiment, the present invention provides an artificial nucleic acid molecule comprising an ORF and a 3'-UTR comprising an optional 3'-UTR element as described above, wherein the ratio of the (reporter) protein amount, e.g. the amount of luciferase, observed 48 hours after initiation of expression to the (reporter) protein amount observed 6 hours after initiation of expression, preferably in a mammalian expression system, such as in mammalian cells, e.g. in HeLa cells, is preferably above about 0.4, more preferably above about 0.5, more preferably above about 0.6, even more preferably above about 0.7, e.g. between about 0.4 and about 4, preferably between about 0.65 and about 3, more preferably between about 0.7 and 2, wherein preferably the total amount of protein produced from said artificial nucleic acid molecule, e.g. within a time span of 48 hours, is at least the total amount of protein produced, e.g. within said time span, from a reference nucleic acid molecule lacking a 3'-UTR or comprising a reference 3'-UTR lacking the optional 3'-UTR element, such as a 3'-UTR naturally occurring with the ORF of the artificial nucleic acid molecule. In a preferred embodiment, the present invention provides an artificial nucleic acid molecule comprising an ORF and a 3'-UTR comprising an optional 3'-UTR element as described above, wherein the ratio of the (reporter) protein amount, e.g. the amount of luciferase, observed 72 hours after initiation of expression to the (reporter) protein amount observed 6 hours after initiation of expression, preferably in a mammalian expression system, such as in mammalian cells, e.g. in HeLa cells, is preferably above about 0.4, more preferably above about 0.5, more preferably above about 0.6, even more preferably above about 0.7, e.g. between about 0.4 and 1.5, preferably between about 0.65 and about 1.15, more preferably between about 0.7 and 1.0, wherein preferably the total amount of protein produced from said artificial nucleic acid molecule, e.g. within a time span of 72 hours, is at least the total amount of protein produced, e.g. within said time span, from a reference nucleic acid molecule lacking a 3'-UTR or comprising a reference 3'-UTR lacking the optional 3'-UTR element, such as a 3'-UTR naturally occurring with the ORF of the artificial nucleic acid molecule.

In a preferred embodiment, the at least one further 3'-UTR element, which may optionally be comprised in the 3'-UTR of the artificial nucleic acid molecule and which is distinct from a poly(A) sequence, increases or enhances the protein expression from the artificial nucleic acid molecule as defined herein.

Said increase in stability of the artificial nucleic acid molecule, said increase in stability of protein production, said prolongation of protein production and/or said increase/enhancement in protein expression and/or total protein production is preferably determined by comparison with a respective reference nucleic acid molecule lacking a 3'-UTR, e.g. an mRNA lacking a 3'-UTR, or a reference nucleic acid molecule comprising a reference 3'-UTR lacking the optional 3'-UTR element, such as a 3'-UTR naturally occurring with the ORF as describe above.

The mRNA and/or protein production stabilizing effect and efficiency and/or the protein production increasing effect and efficiency of the at least one (optional) 3'-UTR element of the artificial nucleic acid molecule according to the present invention may be determined by any method suitable for this purpose known to skilled person. For example, artificial mRNA molecules may be generated comprising a coding sequence/open reading frame (ORF) for a reporter protein, such as luciferase, and no 3'-UTR, a 3'-UTR lacking the optional 3'-UTR element, such as a 3'-UTR derived from a naturally occurring gene or a 3'-UTR derived from a reference gene (i.e., a reference 3'-UTR, such as a 3'-UTR naturally occurring with the ORF). Such mRNAs may be generated, for example, by in vitro transcription of respective vectors such as plasmid vectors, e.g. comprising a T7 promoter and a sequence encoding the respective mRNA sequences. The generated mRNA molecules may be transfected into cells by any transfection method suitable for transfecting mRNA, for example they may be electroporated into mammalian cells, such as HELA cells, and samples may be analyzed certain time points after transfection, for example, 6 hours, 24 hours, 48 hours, and 72 hours post transfection. Said samples may be analyzed for mRNA quantities and/or protein quantities by methods well known to the skilled person. For example, the quantities of reporter mRNA present in the cells at the sample time points may be determined by quantitative PCR methods. The quantities of reporter protein encoded by the respective mRNAs may be determined, e.g., by Western Blot, ELISA assays, FACS analysis or reporter assays such as luciferase assays depending on the reporter protein used. The effect of stabilizing protein expression and/or prolonging protein expression may be, for example, analyzed by determining the ratio of the protein level observed 48 hours post transfection and the protein level observed 6 hours post transfection. The closer said value is to 1, the more stable the protein expression is within this time period. Such measurements may of course also be performed at 72 or more hours and the ratio of the protein level observed 72 hours post transfection and the protein level observed 6 hours post transfection may be determined to determine stability of protein expression.

In some embodiments, the 3'-UTR of the artificial nucleic acid molecule may comprise a histone stem-loop in addition to the at least one poly(A) sequence and the optional 3'-UTR element as described herein. Such 3'-UTR of the artificial nucleic acid molecule according to the present invention may comprise, for example, in 5'-to-3'-direction, an optional 3'-UTR element as described herein, at least one poly(A) sequence, an optional poly(C) sequence, an optional histone stem-loop sequence, and optionally a further poly(A) sequence or a polyadenylation signal.

In a preferred embodiment, the artificial nucleic acid molecule according to the invention comprises at least one histone stem-loop sequence.

Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

Formula (I) (Stem-Loop Sequence without Stem Bordering Elements):

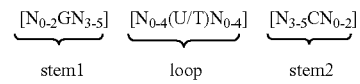

Formula (II) (Stem-Loop Sequence with Stem Bordering Elements):

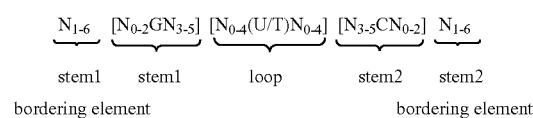

wherein:
stem1 or stem2 bordering element $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;
stem1 $[N_{0-92} GN_{3-5}]$ is reverse complementary or partially reverse complementary with element stem2, and is a consecutive sequence between of 5 to 7 nucleotides;
  wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;
  wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence [$N_{0-4}$ (U/T)$N_{0-4}$] is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 [$N_{3-5}$ $CN_{0-2}$] is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment, the histone stem-loop sequence may be selected according to at least one of the following specific formulae (Ia) or (IIa):

Formula (Ia) (Stem-Loop Sequence without Stem Bordering Elements):

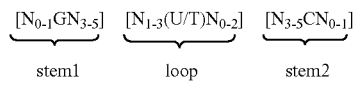

Formula (IIa) (Stem-Loop Sequence with Stem Bordering Elements):

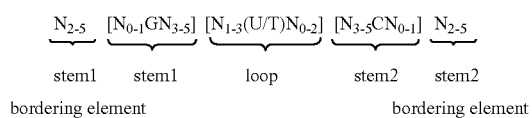

wherein:

N, C, G, T and U are as defined above.

According to a further more particularly preferred embodiment of the first aspect, the artificial nucleic acid molecule sequence may comprise at least one histone stem-loop sequence according to at least one of the following specific formulae (Ib) or (IIb):

Formula (Ib) (Stem-Loop Sequence without Stem Bordering Elements):

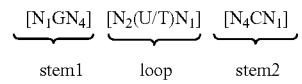

Formula (IIb) (Stem-Loop Sequence with Stem Bordering Elements):

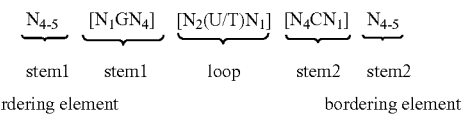

wherein:

N, C, G, T and U are as defined above.

A particular preferred histone stem-loop sequence is the sequence according to SEQ ID NO: 11: CAAAGGCTCTTTTCAGAGCCACCA or more preferably the corresponding RNA sequence of the nucleic acid sequence according to SEQ ID NO: 11.

In some embodiments, the artificial nucleic acid molecule comprises further elements such as a 5'-cap, a poly(C) sequence and/or an IRES-motif. A 5'-cap may be added to the 5'end of an RNA during transcription or post-transcriptionally. Furthermore, the inventive artificial nucleic acid molecule, particularly if the nucleic acid is in the form of an mRNA or encodes an mRNA, may be modified by a sequence of at least 10 cytidines, preferably at least 20 cytidines, more preferably at least 30 cytidines (so-called "poly(C) sequence"). In particular, the inventive artificial nucleic acid molecule may contain, especially if the nucleic acid is in the form of an (m)RNA or encodes an mRNA, a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides. Most preferably, the inventive nucleic acid comprises a poly(C) sequence of 30 cytidine residues. Thus, preferably the artificial nucleic acid molecule according to the present invention comprises, preferably in 5'-to-3' direction, an ORF, at least one 3'-UTR element as described above, at least one poly(A) sequence, a poly(C) sequence, a histone stem-loop sequence and, optionally, a further poly(A) sequence.

An internal ribosome entry site (IRES) sequence or IRES-motif may separate several open reading frames, for example if the artificial nucleic acid molecule encodes two or more peptides or proteins. An IRES-sequence may be particularly helpful if the artificial nucleic acid molecule is a bi- or multicistronic nucleic acid molecule.

Furthermore, the artificial nucleic acid molecule may comprise additional 5'-elements, preferably a 5'-UTR, a promoter, or a 5'-UTR and a promoter containing-sequence. The promoter may drive and/or regulate transcription of the artificial nucleic acid molecule according to the present invention, for example of an artificial DNA-molecule according to the present invention. Furthermore, the 5'-UTR may consist of or may comprise the 5'-UTR of a gene as defined herein. Furthermore, the 5'-UTR may interact with the 3'-UTR of the inventive artifical nucleic acid molecule and thus may support the effect of the 3'-UTR of the inventive nucleic acid molecule. Such elements may further support stability and translational efficiency.

In a particularly preferred embodiment of the present invention, the artificial nucleic acid molecule comprises at least one 5'-untranslated region element (5'UTR element), which comprises or consists of a nucleic acid sequence, which is derived from the 5'UTR of a TOP gene or which is derived from a fragment, homolog or variant of the 5'UTR of a TOP gene.

It is particularly preferred that the 5'UTR element does not comprise a TOP-motif or a 5'TOP, as defined above.

The nucleic acid sequence, which is derived from the 5'UTR of a TOP gene, is preferably derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element is preferably selected from 5'-UTR elements comprising or consisting of a nucleic acid sequence, which is derived from a nucleic acid sequence selected from the group consisting of SEQ ID NOs. 1-1363, SEQ ID NO. 1395, SEQ ID NO. 1421 and SEQ ID NO. 1422 of the patent application WO2013/143700, whose disclosure is incorporated herein by reference, from the homologs of SEQ ID NOs. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID NOs. 1-1363, SEQ ID NO. 1395, SEQ ID NO. 1421 and SEQ ID NO. 1422 of the patent application WO2013/143700" refers to sequences of other species than *homo sapiens*, which are homologous to the sequences according to SEQ ID NOs. 1-1363, SEQ ID NO. 1395, SEQ ID NO. 1421 and SEQ ID NO. 1422 of the patent application WO2013/143700.

In a preferred embodiment, the 5'UTR element comprises or consists of a nucleic acid sequence, which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 and SEQ ID NO. 1422 of the patent application WO2013/143700, from the homologs of SEQ ID NOs. 1-1363, SEQ ID NO. 1395, SEQ ID NO. 1421 and SEQ ID NO. 1422 of the patent application WO2013/143700, from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 and SEQ ID NO. 1422 of the patent application WO2013/143700, from the homologs of SEQ ID NOs. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'UTR element comprises or consists of a nucleic acid sequence, which is derived from a 5'UTR of a TOP gene encoding a ribosomal protein or from a variant of a 5'UTR of a TOP gene encoding a ribosomal protein. For example, the 5'UTR element comprises or consists of a nucleic acid sequence, which is derived from a 5'UTR of a nucleic acid sequence according to any of SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3'end of the sequences) corresponds to the 5'UTR of said sequences.

Preferably, the 5'UTR element comprises or consists of a nucleic acid sequence, which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence, which is derived from a 5'UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'UTR element comprises or consists of a nucleic acid sequence, which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'UTR element does not comprise the 5'TOP of said gene.

Accordingly, in a particularly preferred embodiment, the 5'UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 12 (5'-UTR of human ribosomal protein Large 32 lacking the 5' terminal oligopyrimidine tract: GGCGCTGCCTACGGAGGTGGCAGCCATCTCCT-TCTCGGCATC; corresponding to SEQ ID No. 1368 of the patent application WO2013/143700) or preferably to a corresponding RNA sequence, or wherein the at least one 5'UTR element comprises or consists of a fragment of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 12 or more preferably to a corresponding RNA sequence, wherein, preferably, the fragment is as described above, i.e. being a continuous stretch of nucleotides representing at least 20%, preferably at least 30%, more preferably at least 40% of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the artificial nucleic acid molecule comprises a 5'UTR element, which comprises or consists of a nucleic acid sequence, which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3E1P, EIF4A2, PABPC1, HNRNPA1, TPT1, TUBB1, UBA52, NPM1, ATP5G2, GNB2L1, NME2, UQCRB or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5'terminal oligopyrimidine tract (TOP) and wherein further optionally the 5'UTR element, which is derived from a 5'UTR of a TOP gene, terminates at its 3'-end with a nucleotide located at position 1, 2, 3, 4, 5, 6, 7, 8, 9 or 10 upstream of the start codon (A(U/T)G) of the gene it is derived from.

Accordingly, in some embodiments, the invention provides artificial nucleic acid molecules, preferably mRNA molecules, comprising in 5'-to-3'-direction at least one of the following structures
ORF—poly(A) sequence;
ORF—poly(A) sequence—poly(A) sequence;
ORF—IRES—ORF—poly(A) sequence;
ORF—3'-UTR element—poly(A) sequence;
ORF—poly(A) sequence—3'-UTR element;
ORF—3'-UTR element—poly(A) sequence—poly(C) sequence—histone stem-loop;
ORF—3'-UTR element—poly(A) sequence—poly(C) sequence—poly(A) sequence;
ORF—3'-UTR element—poly(A) sequence—histone stem-loop—poly(A) sequence;
ORF—3'-UTR element—poly(A) sequence—poly(C) sequence—histone stem-loop—poly(A) sequence;
5'-UTR—ORF—3'-UTR element—poly(A) sequence—poly(C) sequence—histone stem-loop—poly(A) sequence; or 5'-cap—5'-UTR—ORF—3'-UTR element—poly(A) sequence—poly(C) sequence-histone stem-loop—poly(A) sequence.

Preferably, the artificial nucleic acid molecule according to the present invention, preferably the open reading frame thereof, is at least partially G/C modified. Thus, the inventive artificial nucleic acid molecule may be thermodynamically stabilized by modifying the G (guanosine) and/or C (cytidine) content (G/C content) of the molecule. The G/C content of the open reading frame of an artificial nucleic acid molecule according to the present invention may be increased compared to the G/C content of the open reading frame of a corresponding wild type sequence, preferably by using the degeneration of the genetic code. Thus, the encoded amino acid sequence of the artificial nucleic acid molecule is preferably not modified by the G/C modification compared to the coded amino acid sequence of the particular wild type sequence. The codons of the coding sequence or the whole artificial nucleic acid molecule, e.g. an mRNA, may therefore be varied compared to the wild type coding sequence, such that they include an increased amount of G/C nucleotides while the translated amino acid sequence is maintained. Due to the fact that several codons encode one and the same amino acid (so-called degeneration of the genetic code), it is feasible to alter codons while not altering the encoded peptide/protein sequence (so-called alternative codon usage). Hence, it is possible to specifically introduce certain codons (in exchange for the respective wild-type codons encoding the same amino acid), which are more favourable with respect to stability of RNA and/or with respect to codon usage in a subject (so-called codon optimization).

Depending on the amino acid to be encoded by the coding region of the inventive artificial nucleic acid molecule as defined herein, there are various possibilities for modification of the nucleic acid sequence, e.g. the open reading frame, compared to its wild type coding region. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U/T is present.

In contrast, codons, which contain A and/or U/T nucleotides may be modified by substitution of other codons, which encode the same amino acids but contain no A and/or U/T. For example
the codons for Pro can be modified from CC(U/T) or CCA to CCC or CCG;
the codons for Arg can be modified from CG(U/T) or CGA or AGA or AGG to CGC or CGG;
the codons for Ala can be modified from GC(U/T) or GCA to GCC or GCG;
the codons for Gly can be modified from GG(U/T) or GGA to GGC or GGG.

In other cases, although A or (U/T) nucleotides cannot be eliminated from the codons, it is however possible to decrease the A and (U/T) content by using codons, which contain a lower content of A and/or (U/T) nucleotides. Examples of these are:
The codons for Phe can be modified from (U/T)(U/T)(U/T) to (U/T) (U/T)C;
the codons for Leu can be modified from (U/T) (U/T)A, (U/T) (U/T)G, C(U/T) (U/T) or C(U/T)A to C(U/T)C or C(U/T)G;
the codons for Ser can be modified from (U/T)C(U/T) or (U/T)CA or AG(U/T) to (U/T)CC, (U/T)CG or AGC;

the codon for Tyr can be modified from (U/T)A(U/T) to (U/T)AC;
the codon for Cys can be modified from (U/T)G(U/T) to (U/T)GC;
the codon for His can be modified from CA(U/T) to CAC;
the codon for Gln can be modified from CAA to CAG;
the codons for Ile can be modified from A(U/T)(U/T) or A(U/T)A to A(U/T)C;
the codons for Thr can be modified from AC(U/T) or ACA to ACC or ACG;
the codon for Asn can be modified from AA(U/T) to AAC;
the codon for Lys can be modified from AAA to AAG;
the codons for Val can be modified from G(U/T)(U/T) or G(U/T)A to G(U/T)C or G(U/T)G;
the codon for Asp can be modified from GA(U/T) to GAC;
the codon for Glu can be modified from GAA to GAG;
the stop codon (U/T)AA can be modified to (U/T)AG or (U/T)GA.

In the case of the codons for Met (A(U/T)G) and Trp ((U/T)GG), on the other hand, there is no possibility of sequence modification without altering the encoded amino acid sequence.

The substitutions listed above can be used either individually or in all possible combinations to increase the G/C content of the open reading frame of the inventive artificial nucleic acid molecule as defined herein, compared to its particular wild type open reading frame (i.e. the original sequence). Thus, for example, all codons for Thr occurring in the wild type sequence can be modified to ACC (or ACG).

Preferably, the G/C content of the open reading frame of the inventive artificial nucleic acid molecule as defined herein is increased by at least 7%, more preferably by at least 15%, particularly preferably by at least 20%, compared to the G/C content of the wild type coding region without altering the encoded amino acid sequence, i.e. using the degeneracy of the genetic code. According to a specific embodiment at least 5%, 10%, 20%, 30%, 40%, 50%, 60%, more preferably at least 70 %, even more preferably at least 80% and most preferably at least 90%, 95% or even 100% of the substitutable codons in the open reading frame of the inventive artificial nucleic acid molecule or a fragment, variant or derivative thereof are substituted, thereby increasing the G/C content of said open reading frame.

In this context, it is particularly preferable to increase the G/C content of the open reading frame of the inventive artificial nucleic acid molecule as defined herein, to the maximum (i.e. 100% of the substitutable codons), compared to the wild type open reading frame, without altering the encoded amino acid sequence.

Furthermore, the open reading frame is preferably at least partially codon-optimized. Codon-optimization is based on the finding that the translation efficiency may be determined by a different frequency in the occurrence of transfer RNAs (tRNAs) in cells. Thus, if so-called "rare codons" are present in the coding region of the inventive artificial nucleic acid molecule as defined herein, to an increased extent, the translation of the corresponding modified nucleic acid sequence is less efficient than in the case, where codons coding for relatively "frequent" tRNAs are present.

Thus, the open reading frame of the inventive artificial nucleic acid molecule is preferably modified compared to the corresponding wild type coding region such that at least one codon of the wild type sequence, which is recognized by a tRNA, which is relatively rare in the cell, is exchanged for a codon, which is recognized by a tRNA, which is comparably frequent in the cell and carries the same amino acid as the relatively rare tRNA. By this modification, the open reading frame of the inventive artificial nucleic acid molecule as defined herein, is modified such that codons, for which frequently occurring tRNAs are available, may replace codons, which correspond to rare tRNAs. In other words, according to the invention, by such a modification all codons of the wild type open reading frame, which are recognized by a rare tRNA, may be exchanged for a codon, which is recognized by a tRNA, which is more frequent in the cell and which carries the same amino acid as the rare tRNA. Which tRNAs occur relatively frequently in the cell and which, in contrast, occur relatively rarely, is known to a person skilled in the art; cf. e.g. Akashi, Curr. Opin. Genet. Dev. 2001, 11(6): 660-666. Accordingly, preferably, the open reading frame is codon-optimized, preferably with respect to the system, in which the artificial nucleic acid molecule according to the present invention is to be expressed, preferably with respect to the system, in which the artificial nucleic acid molecule according to the present invention is to be translated. Preferably, the codon usage of the open reading frame is codon-optimized according to mammalian codon usage, more preferably according to human codon usage. Preferably, the open reading frame is codon-optimized and G/C-content modified.

For further improving degradation resistance, e.g. resistance to in vivo degradation by an exo- or endonuclease, and/or for further improving stability of protein expression from the artificial nucleic acid molecule according to the present invention, the artificial nucleic acid molecule may further comprise modifications, such as backbone modifications, sugar modifications and/or base modifications, e.g., lipid-modifications or the like. Preferably, the transcription and/or the translation of the artificial nucleic acid molecule according to the present invention is not significantly impaired by said modifications.

Generally, the artificial nucleic acid molecule of the present invention may comprise any native (=naturally occurring) nucleotide, e.g. guanosine, uracil, adenosine, and/or cytosine or an analogue thereof. In this respect, nucleotide analogues are defined as natively and non-natively occurring variants of the naturally occurring nucleotides adenosine, cytosine, thymidine, guanosine and uridine. Accordingly, analogues are e.g. chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone (see above) of the RNA sequence. Analogues of guanosine, uridine, adenosine, thymidine and cytosine include, without implying any limitation, any natively occurring or non-natively occurring guanosine, uridine, adenosine, thymidine or cytosine that has been altered e.g. chemically, for example by acetylation, methylation, hydroxylation, etc., including 1-methyl-adenosine, 1-methyl-guanosine, 1-methylinosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymehtylaminomethyl-2-thio-uracil, 5-carboxymethylamonomethyl-uracil, 5-Chloro-Ara-cytosine, 5-Fluorouridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromoadenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642. In the case of an analogue as described above, particular preference may be given according to certain embodiments of the invention to those analogues that increase the protein expression of the encoded peptide or protein or that increase the immunogenicity of the artificial nucleic acid molecule of the invention and/or do not interfere with a further modification of the artificial nucleic acid molecule that has been introduced.

According to a particular embodiment, the artificial nucleic acid molecule of the present invention can contain a lipid modification.

In a preferred embodiment, the artificial nucleic acid molecule according to the invention comprises, preferably from 5' to 3' direction, the following elements:
an ORF;
an optional 3'-UTR element as described herein;
a poly(A) sequence, preferably comprising or consisting of 64 adenosine residues;
a poly(C) sequence, preferably comprising or consisting of 30 cytosine residues;
a histone stem-loop sequence, preferably comprising or consisting of the nucleic acid sequence according to SEQ ID NO: 11; and
a poly(A) sequence, preferably comprising at least 160 adenosine residues.

Preferably, the artificial nucleic acid molecule, which is preferably an mRNA, optionally further comprises a 5'-UTR, preferably comprising a 5'-UTR element comprising or consisting of a nucleic acid, which is derived from a 5'-UTR of a TOP gene encoding a ribosomal Large protein (RPL) or from a homolog, a fragment or variant thereof, preferably lacking the 5' TOP motif. Even more preferably, the inventive artificial nucleic acid molecule further comprises a 5'-cap structure.

In a preferred embodiment, the at least one open reading frame of the inventive artificial nucleic acid molecule encodes a therapeutic protein or peptide. In another embodiment, an antigen is encoded by the at least one open reading frame, such as a pathogenic antigen, a tumour antigen, an allergenic antigen or an autoimmune antigen. Therein, the administration of the artificial nucleic acid molecule encoding the antigen is used in a genetic vaccination approach against a disease involving said antigen.

In an alternative embodiment, an antibody is encoded by the at least one open reading frame of the artificial nucleic acid molecule according to the invention.

Antigens:
Pathogenic Antigens:

The artificial nucleic acid molecule according to the present invention may encode a protein or a peptide, which comprises a pathogenic antigen or a fragment, variant or derivative thereof. Such pathogenic antigens are derived from pathogenic organisms, in particular bacterial, viral or protozoological (multicellular) pathogenic organisms, which evoke an immunological reaction in a subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease which are preferably selected from antigens derived from the pathogens *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, Astroviridae, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, *Bunyaviridae* family, *Burkholderia cepacia* and other *Burkholderia* species, *Burkholderia mallei*, *Burkholderia pseudomallei*, *Caliciviridae* family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, *Kingella kingae*, *Klebsiella granulomatis*, *Kuru prion*, Lassa virus, *Legionella pneumophila*, *Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, *Microsporidia phylum*, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia* spp, *Onchocerca volvulus*, *Orientia tsutsugamushi*, Orthomyxoviridae family (Influenza), *Paracoccidioides brasiliensis*, *Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, and *Yersinia pseudotuberculosis*.

In this context, particularly preferred are antigens from the pathogens selected from Influenza virus, respiratory syncytial virus (RSV), Herpes simplex virus (HSV), human Papilloma virus (HPV), Human immunodeficiency virus (HIV), *Plasmodium*, *Staphylococcus aureus*, *Dengue virus*, *Chlamydia trachomatis*, Cytomegalovirus (CMV), Hepatitis B virus (HBV), *Mycobacterium tuberculosis*, Rabies virus, and Yellow Fever Virus.

Tumour Antigens:

In a further embodiment the artificial nucleic acid molecule according to the present invention may encode a protein or a peptide, which comprises a peptide or protein comprising a tumour antigen, a fragment, variant or derivative of said tumour antigen, preferably, wherein the tumour antigen is a melanocyte-specific antigen, a cancer-testis antigen or a tumour-specific antigen, preferably a CT-X antigen, a non-X CT-antigen, a binding partner for a CT-X antigen or a binding partner for a non-X CT-antigen or a tumour-specific antigen, more preferably a CT-X antigen, a binding partner for a non-X CT-antigen or a tumour-specific antigen or a fragment, variant or derivative of said tumour antigen; and wherein each of the nucleic acid sequences encodes a different peptide or protein; and wherein at least one of the nucleic acid sequences encodes for 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, caireticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGFR1, VEGFR-2/FLK-1, WT1 and a immunoglobulin idiotype of a lymphoid blood cell or a T cell receptor idiotype of a lymphoid blood cell, or a fragment, variant or derivative of said tumour antigen; preferably survivin or a homologue thereof, an antigen from the MAGE-family or a binding partner thereof or a fragment, variant or derivative of said tumour antigen. Particularly preferred in this context are the tumour antigens NY-ESO-1, 5T4, MAGE-C1, MAGE-C2, Survivin, Muc-1, PSA, PSMA, PSCA, STEAP and PAP.

In a preferred embodiment, the artificial nucleic acid molecule encodes a protein or a peptide, which comprises a therapeutic protein or a fragment, variant or derivative thereof.

Therapeutic proteins as defined herein are peptides or proteins, which are beneficial for the treatment of any inherited or acquired disease or which improves the condition of an individual. Particularly, therapeutic proteins play an important role in the creation of therapeutic agents that could modify and repair genetic errors, destroy cancer cells or pathogen infected cells, treat immune system disorders, treat metabolic or endocrine disorders, among other functions. For instance, Erythropoietin (EPO), a protein hormone can be utilized in treating patients with erythrocyte deficiency, which is a common cause of kidney complications. Furthermore adjuvant proteins, therapeutic antibodies are encompassed by therapeutic proteins and also hormone replacement therapy which is e.g. used in the therapy of women in menopause. In more recent approaches, somatic cells of a patient are used to reprogram them into pluripotent stem cells, which replace the disputed stem cell therapy. Also these proteins used for reprogramming of somatic cells or used for differentiating of stem cells are defined herein as therapeutic proteins. Furthermore, therapeutic proteins may be used for other purposes, e.g. wound healing, tissue regeneration, angiogenesis, etc. Furthermore, antigen-specific B cell receptors and fragments and variants thereof are defined herein as therapeutic proteins.

Therefore therapeutic proteins can be used for various purposes including treatment of various diseases like e.g. infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired.

In this context, particularly preferred therapeutic proteins, which can be used inter alia in the treatment of metabolic or endocrine disorders, are selected from (in brackets the particular disease for which the therapeutic protein is used in the treatment): Acid sphingomyelinase (Niemann-Pick disease), Adipotide (obesity), Agalsidase-beta (human galactosidase A) (Fabry disease; prevents accumulation of lipids that could lead to renal and cardiovascular complications), Alglucosidase (Pompe disease (glycogen storage disease type II)), alpha-galactosidase A (alpha-GAL A, Agalsidase alpha) (Fabry disease), alpha-glucosidase (Glycogen storage disease (GSD), Morbus Pompe), alpha-L-iduronidase (mucopolysaccharidoses (MPS), Hurler syndrome, Scheie syndrome), alpha-N-acetylglucosaminidase (Sanfilippo syndrome), Amphiregulin (cancer, metabolic disorder), Angiopoietin ((Ang1, Ang2, Ang3, Ang4, ANGPTL2, ANGPTL3, ANGPTL4, ANGPTL5, ANGPTL6, ANGPTL7) (angiogenesis, stabilize vessels), Betacellulin (metabolic disorder), Beta-glucuronidase (Sly syndrome), Bone morphogenetic protein BMPs (BMP1, BMP2, BMP3, BMP4, BMP5, BMP6, BMP7, BMP8a, BMP8b, BMP10, BMP15) (regenerative effect, bone-related conditions, chronic kidney disease (CKD)), CLN6 protein (CLN6 disease—Atypical Late Infantile, Late Onset variant, Early Juvenile, Neuronal Ceroid Lipofuscinoses (NCL)), Epidermal growth factor (EGF) (wound healing, regulation of cell growth, proliferation, and differentiation), Epigen (metabolic disorder), Epiregulin (metabolic disorder), Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23) (wound healing, angiogenesis, endocrine disorders, tissue regeneration), Galsulphase (Mucopolysaccharidosis VI), Ghrelin (irritable bowel syndrome (IBS), obesity, Prader-Willi syndrome, type II diabetes mellitus), Glucocerebrosidase (Gaucher's disease), GM-CSF (regenerative effect, production of white blood cells, cancer), Heparin-binding EGF-like growth factor (HB-EGF) (wound healing, cardiac hypertrophy and heart development and function), Hepatocyte growth factor HGF (regenerative effect, wound healing), Hepcidin (iron metabolism disorders, Beta-thalassemia), Human albumin (Decreased production of albumin (hypoproteinaemia), increased loss of albumin (nephrotic syndrome), hypovolaemia, hyperbilirubinaemia), Idursulphase (Iduronate-2-sulphatase) (Mucopolysaccharidosis II (Hunter syndrome)), Integrins αVβ3, αVβ5 and α5β1 (Bind matrix macromolecules and proteinases, angiogenesis), Iduronate sulfatase (Hunter syndrome), Laronidase (Hurler and Hurler-Scheie forms of mucopolysaccharidosis I), N-acetylgalactosamine-4-sulfatase (rhASB; galsulfase, Arylsulfatase A (ARSA), Arylsulfatase B (ARSB)) (arylsulfatase B deficiency, Maroteaux-Lamy syndrome, mucopolysaccharidosis VI), N-acetylglucosamine-6-sulfatase (Sanfilippo syndrome), Nerve growth factor (NGF, Brain-Derived Neurotrophic Factor (BDNF), Neurotrophin-3 (NT-3), and Neurotrophin 4/5 (NT-4/5) (regenerative effect, cardiovascular diseases, coronary atherosclerosis, obesity, type 2 diabetes, metabolic syndrome, acute coronary syndromes, dementia, depression, schizophrenia, autism, Rett syndrome, anorexia nervosa, bulimia nervosa, wound healing, skin ulcers, corneal ulcers, Alzheimer's disease), Neuregulin (NRG1, NRG2, NRG3, NRG4) (metabolic disorder, schizophrenia), Neuropilin (NRP-1, NRP-2) (angiogenesis, axon guidance, cell survival, migration), Obestatin (irritable bowel syndrome (IBS), obesity, Prader-Willi syndrome, type II diabetes mellitus), Platelet Derived Growth factor (PDGF (PDFF-A, PDGF-B, PDGF-C, PDGF-D) (regenerative effect, wound healing, disorder in angiogenesis, Arteriosclerosis, Fibrosis, cancer), TGF beta receptors (endoglin, TGF-beta 1 receptor, TGF-beta 2 receptor, TGF-beta 3 receptor) (renal fibrosis, kidney disease, diabetes, ultimately end-stage renal disease (ESRD), angiogenesis), Thrombopoietin (THPO) (Megakaryocyte growth and development factor (MGDF)) (platelets disorders, platelets for donation, recovery of platelet counts after myelosuppressive chemotherapy), Transforming Growth factor (TGF (TGF-alpha, TGF-beta (TGFbeta1, TGFbeta2, and TGFbeta3))) (regenerative effect, wound healing, immunity, cancer, heart disease, diabetes, Marian syndrome, Loeys-Dietz syndrome), VEGF (VEGF-A, VEGF-B, VEGF-C, VEGF-D, VEGF-E, VEGF-F and PIGF) (regenerative effect, angiogenesis, wound healing, cancer, permeability), Nesiritide (Acute decompensated congestive heart failure), Trypsin (Decubitus ulcer, varicose ulcer, debridement of eschar, dehiscent wound, sunburn, meconium ileus), adrenocorticotrophic hormone (ACTH) ("Addison's disease, Small cell carcinoma, Adrenoleukodystrophy, Congenital adrenal hyperplasia, Cushing's syndrome, Nelson's syndrome, Infantile spasms), Atrial-natriuretic peptide (ANP) (endocrine disorders), Cholecystokinin (diverse), Gastrin (hypogastrinemia), Leptin (Diabetes, hypertriglyceridemia, obesity), Oxytocin (stimulate breastfeeding, non-progression of parturition), Somatostatin (symptomatic treatment of carcinoid syndrome, acute variceal bleeding, and acromegaly, polycystic diseases of the liver and kidney, acromegaly and symptoms caused by neuroendocrine tumors), Vasopressin (antidiuretic hormone) (diabetes insipidus), Calcitonin (Postmenopausal osteoporosis, Hypercalcaemia, Paget's disease, Bone metastases, Phantom limb pain, Spinal Stenosis), Exenatide (Type 2 diabetes resistant to treatment with metformin and a sulphonylurea), Growth hormone (GH), somatotropin (Growth failure due to GH deficiency or chronic renal insufficiency, Prader-Willi syndrome, Turner syndrome, AIDS wasting or cachexia with antiviral therapy), Insulin (Diabetes mellitus, diabetic ketoacidosis, hyperkalaemia), Insulin-like growth factor 1 IGF-1 (Growth failure in children with GH gene deletion or severe primary IGF1 deficiency, neurodegenerative disease, cardiovascular diseases, heart failure), Mecasermin rinfabate, IGF-1 analog (Growth failure in children with GH gene deletion or severe primary IGF1 deficiency, neurodegenerative disease, cardiovascular diseases, heart failure), Mecasermin, IGF-1 analog (Growth failure in children with GH gene deletion or severe primary IGF1 deficiency, neurodegenerative disease, cardiovascular diseases, heart failure), Pegvisomant (Acromegaly), Pramlintide (Diabetes mellitus, in combination with insulin), Teriparatide (human parathyroid hormone residues 1-34) (Severe osteoporosis), Becaplermin (Debridement adjunct for diabetic ulcers), Dibotermin-alpha (Bone morphogenetic protein 2) (Spinal fusion surgery, bone injury repair), Histrelin acetate (gonadotropin releasing hormone; GnRH) (Precocious puberty), Octreotide (Acromegaly, symptomatic relief of VIP-secreting adenoma and metastatic carcinoid tumours), and Palifermin (keratinocyte growth factor; KGF) (Severe oral mucositis in patients undergoing chemotherapy, wound healing).

These and other proteins are understood to be therapeutic, as they are meant to treat the subject by replacing its defective endogenous production of a functional protein in sufficient amounts. Accordingly, such therapeutic proteins are typically mammalian, in particular human proteins.

For the treatment of blood disorders, diseases of the circulatory system, diseases of the respiratory system, cancer or tumour diseases, infectious diseases or immunedeficiencies following therapeutic proteins may be used: Alteplase (tissue plasminogen activator; tPA) (Pulmonary embolism, myocardial infarction, acute ischaemic stroke, occlusion of central venous access devices), Anistreplase (Thrombolysis), Antithrombin III (AT-III) (Hereditary AT-III deficiency, Thromboembolism), BivalirudinI (Reduce blood-clotting risk in coronary angioplasty and heparin-induced thrombocytopaenia), Darbepoetin-alpha (Treatment of anaemia in patients with chronic renal insufficiency and chronic renal failure (+/−dialysis)), Drotrecogin-alpha (activated protein C) (Severe sepsis with a high risk of death), Erythropoietin, Epoetin-alpha, erythropoetin, erthropoyetin (Anaemia of chronic disease, myleodysplasia, anaemia due to renal failure or chemotherapy, preoperative preparation), Factor IX (Haemophilia B), Factor Vila (Haemorrhage in patients with haemophilia A or B and inhibitors to factor VIII or factor IX), Factor VIII (Haemophilia A), Lepirudin (Heparin-induced thrombocytopaenia), Protein C concentrate (Venous thrombosis, Purpura fulminans), Reteplase (deletion mutein of tPA) (Management of acute myocardial infarction, improvement of ventricular function), Streptokinase (Acute evolving transmural myocardial infarction, pulmonary embolism, deep vein thrombosis, arterial thrombosis or embolism, occlusion of arteriovenous cannula), Tenecteplase (Acute myocardial infarction), Urokinase (Pulmonary embolism), Angiostatin (Cancer), Anti-CD22 immunotoxin (Relapsed CD33+acute myeloid leukaemia), Denileukin diftitox (Cutaneous T-cell lymphoma (CTCL)), Immunocyanin (bladder and prostate cancer), MPS (Metallopanstimulin) (Cancer), Aflibercept (Non-small cell lung cancer (NSCLC), metastatic colorectal cancer (mCRC), hormone-refractory metastatic prostate cancer, wet macular degeneration), Endostatin (Cancer, inflammatory diseases like rheumatoid arthritis as well as Crohn's disease, diabetic retinopathy, psoriasis, and endometriosis), Collagenase (Debridement of chronic dermal ulcers and severely burned areas, Dupuytren's contracture, Peyronie's disease), Human deoxy-ribonuclease I, dornase (Cystic fibrosis; decreases respiratory tract infections in selected patients with FVC greater than 40% of predicted), Hyaluronidase (Used as an adjuvant to increase the absorption and dispersion of injected drugs, particularly anaesthetics in ophthalmic surgery and certain imaging agents), Papain (Debridement of necrotic tissue or liquefication of slough in acute and chronic lesions, such as pressure ulcers, varicose and diabetic ulcers, burns, postoperative wounds, pilonidal cyst wounds, carbuncles, and other wounds), L-Asparaginase (Acute lymphocytic leukaemia, which requires exogenous asparagine for proliferation), Peg-asparaginase (Acute lymphocytic leukaemia, which requires exogenous asparagine for proliferation), Rasburicase (Paediatric patients with leukaemia, lymphoma, and solid tumours who are undergoing anticancer therapy that may cause tumour lysis syndrome), Human chorionic gonadotropin (HCG) (Assisted reproduction), Human follicle-stimulating hormone (FSH) (Assisted reproduction), Lutropin-alpha (Infertility with luteinizing hormone deficiency), Prolactin (Hypoprolactinemia, serum prolactin deficiency, ovarian dysfunction in women, anxiety, arteriogenic erectile dysfunction, premature ejaculation, oligozoospermia, asthenospermia, hypofunction of seminal vesicles, hypoandrogenism in men), alpha-1-Proteinase inhibitor (Congenital antitrypsin deficiency), Lactase (Gas, bloating, cramps and diarrhoea due to inability to digest lactose), Pancreatic enzymes (lipase, amylase, protease) (Cystic fibrosis, chronic pancreatitis, pancreatic insufficiency, post-Billroth II gastric bypass surgery, pancreatic duct obstruction, steatorrhoea, poor digestion, gas, bloating), Adenosine deaminase (pegademase bovine, PEG-ADA) (Severe combined immunodeficiency disease due to adenosine deaminase deficiency), Abatacept (Rheumatoid arthritis (especially when refractory to TNFalpha inhibition)), Alefacept (Plaque Psoriasis), Anakinra (Rheumatoid arthritis), Etanercept (Rheumatoid arthritis, polyarticular-course juvenile rheumatoid arthritis, psoriatic arthritis, ankylosing spondylitis, plaque psoriasis, ankylosing spondylitis), Interleukin-1 (IL-1) receptor antagonist, Anakinra (inflammation and cartilage degradation associated with rheumatoid arthritis), Thymulin (neurodegenerative diseases, rheumatism, anorexia nervosa), TNF-alpha antagonist (autoimmune disorders such as rheumatoid arthritis, ankylosing spondylitis, Crohn's disease, psoriasis, hidradenitis suppurativa, refractory asthma), Enfuvirtide (HIV-1 infection), and Thymosin al (Hepatitis B and C).

(in brackets is the particular disease for which the therapeutic protein is used in the treatment)

In a further aspect, the present invention provides a vector comprising an artificial nucleic acid molecule comprising an ORF and a 3'-UTR, the 3'-UTR comprising at least one poly(A) sequence as defined herein, wherein the at least one poly(A) sequence comprises at least 70 adenine nucleotides. In a preferred embodiment, the artificial nucleic acid molecule comprises a 3'-UTR that comprises at least two poly(A) sequences as defined herein.

The 3'-UTR and the ORF are as described above for the artificial nucleic acid molecule according to the present invention. The cloning site may be any sequence that is suitable for introducing an open reading frame or a sequence comprising an open reading frame, such as one or more restriction sites. Thus, the vector comprising a cloning site is preferably suitable for inserting an open reading frame into the vector, preferably for inserting an open reading frame 5' to the 3'-UTR. Preferably the cloning site or the ORF is located 5' to the 3'-UTR, preferably in close proximity to the 5'-end of the 3'-UTR. For example, the cloning site or the ORF may be directly connected to the 5'-end of the 3'-UTR or they may be connected via a stretch of nucleotides, such as by a stretch of 2, 4, 6, 8, 10, 20 etc. nucleotides as described above for the artificial nucleic acid molecule according to the present invention.

Preferably, the vector according to the present invention is suitable for producing the artificial nucleic acid molecule according to the present invention, preferably for producing an artificial mRNA according to the present invention, for example, by optionally inserting an open reading frame or a sequence comprising an open reading frame into the vector and transcribing the vector. Thus, preferably, the vector comprises elements needed for transcription, such as a promoter, e.g. an RNA polymerase promoter. Preferably, the vector is suitable for transcription using eukaryotic, prokaryotic, viral or phage transcription systems, such as eukaryotic cells, prokaryotic cells, or eukaryotic, prokaryotic, viral or phage in vitro transcription systems. Thus, for example, the vector may comprise a promoter sequence, which is recognized by a polymerase, such as by an RNA polymerase, e.g. by a eukaryotic, prokaryotic, viral, or phage RNA polymerase. In a preferred embodiment, the vector comprises a phage RNA polymerase promoter such as an SP6, T3 or T7, preferably a T7 promoter. Preferably, the vector is suitable for in vitro transcription using a phage based in vitro transcription system, such as a T7 RNA polymerase based in vitro transcription system.

In another preferred embodiment, the vector may be used directly for expression of the encoded peptide or protein in cells or tissue. For this purpose, the vector comprises particular elements, which are necessary for expression in those cells/tissue e.g. particular promoter sequences, such as a CMV promoter.

The vector may further comprise a polyadenylation signal as described above for the artificial nucleic acid molecule according to the present invention.

The vector may be an RNA vector or a DNA vector. Preferably, the vector is a DNA vector. The vector may be any vector known to the skilled person, such as a viral vector or a plasmid vector. Preferably, the vector is a plasmid vector, preferably a DNA plasmid vector.

In a preferred embodiment of the invention, the present invention provides a vector comprising the artificial nucleic acid molecule according to the invention.

Preferably, the vector is a circular molecule. Preferably, the vector is a double-stranded molecule, such as a double-stranded DNA molecule. Such circular, preferably double stranded DNA molecule may be used conveniently as a storage form for the inventive artificial nucleic acid molecule. Furthermore, it may be used for transfection of cells, for example, cultured cells. Also it may be used for in vitro transcription for obtaining an artificial RNA molecule according to the invention.

Preferably, the vector, preferably the circular vector, is linearizable, for example, by restriction enzyme digestion. In a preferred embodiment, the vector comprises a cleavage site, such as a restriction site, preferably a unique cleavage site, located immediately 3' to the 3'-UTR, or located 3' to the poly(A) sequence or—if present—to a polyadenylation signal, or—if present—located 3' to the poly(C) sequence, or—if present—located 3' to the histone stem-loop. Thus, preferably, the product obtained by linearizing the vector terminates at the 3'end with the 3'-end of the 3'-UTR, or with the 3'-end of the poly(A) sequence or—if present—polyadenylation signal, or—if present—with the 3'-end of the poly(C) sequence, or—if present—with the 3'-end of the histone stem-loop. In the embodiment, wherein the vector according to the present invention comprises the artificial nucleic acid molecule according to the present invention, a restriction site, preferably a unique restriction site, is preferably located immediately 3' to the 3'-end of the artificial nucleic acid molecule. Preferably, a restriction site for linearization of the circular vector molecule is located on the 3' side of the 3'-UTR of the coding strand.

In a further aspect, the present invention relates to a cell comprising the artificial nucleic acid molecule according to the present invention or the vector according to present invention. The cell may be any cell, such as a bacterial cell, insect cell, plant cell, vertebrate cell, e.g. a mammalian cell. Such cell may be, e.g., used for replication of the vector of the present invention, for example, in a bacterial cell. Furthermore, the cell may be used for transcribing the artificial nucleic acid molecule or the vector according to the present invention and/or translating the open reading frame of the artificial nucleic acid molecule or the vector according to the present invention. For example, the cell may be used for recombinant protein production.

The cells according to the present invention are, for example, obtainable by standard nucleic acid transfer methods, such as standard transfection, transduction or transformation methods. For example, the artificial nucleic acid molecule or the vector according to the present invention may be transferred into the cell by electroporation, lipofection, e.g. based on cationic lipids and/or liposomes, calcium phosphate precipitation, nanoparticle based transfection, virus based transfection, or based on cationic polymers, such as DEAE-dextran or polyethylenimine etc.

Preferably, the cell is a mammalian cell, such as a cell of human subject, a domestic animal, a laboratory animal, such as a mouse or rat cell. Preferably, the cell is a human cell. The cell may be a cell of an established cell line, such as a CHO, BHK, 293T, COS-7, HELA, HEK, etc. or the cell may be a primary cell, such as a human dermal fibroblast (HDF) cell etc., preferably a cell isolated from an organism. In a preferred embodiment, the cell is an isolated cell of a mammalian subject, preferably of a human subject. For example, the cell may be an immune cell, such as a dendritic cell, a cancer or tumor cell, or any somatic cell etc., preferably of a mammalian subject, preferably of a human subject.

In a further aspect, the present invention provides a pharmaceutical composition comprising the artificial nucleic acid molecule according to the present invention, the vector according the present invention, or the cell according to the present invention. The pharmaceutical composition according to the invention may be used, e.g., as a vaccine, for example, for genetic vaccination. Thus, the ORF may, e.g., encode an antigen to be administered to a patient for vaccination. Thus, in a preferred embodiment, the pharmaceutical composition according to the present invention is a vaccine. Furthermore, the pharmaceutical composition according to the present invention may be used, e.g., for gene therapy.

Preferably, the pharmaceutical composition further comprises one or more pharmaceutically acceptable vehicles, diluents and/or excipients and/or one or more adjuvants. In the context of the present invention, a pharmaceutically acceptable vehicle typically includes a liquid or non-liquid basis for the inventive pharmaceutical composition. In one embodiment, the pharmaceutical composition is provided in liquid form. In this context, preferably, the vehicle is based on water, such as pyrogen-free water, isotonic saline or buffered (aqueous) solutions, e.g phosphate, citrate etc. buffered solutions. The buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of mammalian cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

One or more compatible solid or liquid fillers or diluents or encapsulating compounds suitable for administration to a patient may be used as well for the inventive pharmaceutical composition. The term "compatible" as used herein preferably means that these components of the inventive pharmaceutical composition are capable of being mixed with the inventive artificial nucleic acid, vector or cells as defined herein in such a manner that no interaction occurs which would substantially reduce the pharmaceutical effectiveness of the inventive pharmaceutical composition under typical use conditions.

The pharmaceutical composition according to the present invention may optionally further comprise one or more additional pharmaceutically active components. A pharmaceutically active component in this context is a compound that exhibits a therapeutic effect to heal, ameliorate or prevent a particular indication or disease. Such compounds include, without implying any limitation, peptides or proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions, cell wall components (e.g. polysaccharides), modified, attenuated or de-activated (e.g. chemically or by irradiation) pathogens (virus, bacteria etc.).

Furthermore, the inventive pharmaceutical composition may comprise a carrier for the artificial nucleic acid molecule or the vector. Such a carrier may be suitable for mediating dissolution in physiological acceptable liquids, transport and cellular uptake of the pharmaceutical active artificial nucleic acid molecule or the vector. Accordingly, such a carrier may be a component, which may be suitable for depot and delivery of an artificial nucleic acid molecule or vector according to the invention. Such components may be, for example, cationic or polycationic carriers or compounds, which may serve as transfection or complexation agent.

Particularly preferred transfection or complexation agents in this context are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsl, FGF, Lactoferrin, Transportan, Buforin-2, Bac715-24, SynB, SynB(1), pVEC, hCT-derived peptides, SAP, or histones.

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (I):

$$\{(Arg)_l;(Lys)_m;(His)_n;(Orn)_o;(Xaa)_x\};$$ formula (I)

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context, cationic peptides or proteins in the range of 7-30 amino acids are particular preferred.

Further, the cationic or polycationic peptide or protein, when defined according to formula $\{(Arg)_l;(Lys)_m;(His)_n;(Orn)_o;(Xaa)_x\}$ (formula (I)) as shown above and which comprise or are additionally modified to comprise at least one —SH moeity, may be, without being restricted thereto, selected from subformula (Ia):

$$\{(Arg)_l;(Lys)_m;(His)_n;(Orn)_o;(Xaa')_x(Cys)_y\}$$ subformula (Ia)

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (Ib):

$$Cys_1\{(Arg)_l;(Lys)_m;(His)_n;(Orn)_o;(Xaa)_x\}Cys_2$$ subformula (Ib)

wherein empirical formula $\{(Arg)_l(Lys)_m;(His)_n;(Orn)_o;(Xaa)_x\}$ (formula (III)) is as defined herein and forms a core of an amino acid sequence according to (semiempirical) formula (III) and wherein $Cys_1$ and $Cys_2$ are Cysteines proximal to, or terminal to $(Arg)_l(Lys)_m;(His)_n;(Orn)_o;(Xaa)_x$.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propy]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]-trimethyl-ammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly (N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly (ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

According to another embodiment, the pharmaceutical composition according to the invention may comprise an adjuvant in order to enhance the immunostimulatory properties of the pharmaceutical composition. In this context, an adjuvant may be understood as any compound, which is suitable to support administration and delivery of the components such as the artificial nucleic acid molecule or vector comprised in the pharmaceutical composition according to the invention. Furthermore, such an adjuvant may, without being bound thereto, initiate or increase an immune response of the innate immune system, i.e. a non-specific immune response. With other words, when administered, the pharmaceutical composition according to the invention typically initiates an adaptive immune response directed to the antigen encoded by the artificial nucleic acid molecule. Additionally, the pharmaceutical composition according to the invention may generate an (supportive) innate immune response due to addition of an adjuvant as defined herein to the pharmaceutical composition according to the invention.

Such an adjuvant may be selected from any adjuvant known to a skilled person and suitable for the present case, i.e. supporting the induction of an immune response in a mammal. Preferably, the adjuvant may be selected from the group consisting of, without being limited thereto, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i)N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT oral adjuvant (*E. coli* labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and D-MURAPALMITINE™ (Nac-Mur-L-Thr-D-isoGln-sn-glycerol-dipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5 c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Suitable adjuvants may also be selected from cationic or polycationic compounds wherein the adjuvant is preferably prepared upon complexing the artificial nucleic acid molecule or the vector of the pharmaceutical composition with the cationic or polycationic compound. Association or complexing the artificial nucleic acid molecule or the vector of the pharmaceutical composition with cationic or polycationic compounds as defined herein preferably provides adjuvant properties and confers a stabilizing effect to the artificial nucleic acid molecule or the vector of the pharmaceutical composition. Particularly such preferred, such cationic or polycationic compounds are selected from cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsl, FGF, Lactoferrin, Transportan, Buforin-2, Bac715-24, SynB, SynB(1), pVEC, hCT-derived peptides, SAP, protamine, spermine, spermidine, or histones. Further preferred cationic or polycationic compounds may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicyl-spermin, DIMRI: Dimyristo-oxypropyl dimethyl hydroxy-ethyl ammonium bromide, DOTAP: dioleoyloxy-3-(trimethylammonio)propane, DC-6-14: O,O-ditetradecanoyl-N-(a-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxy-propyl-oxymethyloxy)ethyl]-trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amido-amine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Blockpolymers consisting of a combination of one or more cationic blocks (e.g. selected of a cationic polymer as mentioned above) and of one or more hydrophilic- or hydrophobic blocks (e.g polyethyleneglycole); etc.

Additionally, preferred cationic or polycationic proteins or peptides, which can be used as an adjuvant by complexing the artificial nucleic acid molecule or the vector, preferably an RNA, of the composition, may be selected from following proteins or peptides having the following total formula (I): $(Arg)_l;(Lys)_m;(His)_n;(Orn)_o;(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred oligoarginines in this context are e.g. $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc.

In a preferred embodiment, the artificial nucleic acid molecule, preferably an RNA molecule, is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w:w) or of about 3:1 (w/w) to about 1:1 (w/w), and most preferably a ratio of about 3:1 (w/w) to about 2:1 (w/w) of RNA to cationic or polycationic compound and/or with a polymeric carrier; or optionally in a nitrogen/phosphate ratio of RNA to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9.

The ratio of the artificial nucleic acid or the vector to the cationic or polycationic compound may be calculated on the basis of the nitrogen/phosphate ratio (N/P-ratio) of the entire nucleic acid complex. For example, 1 µg RNA typically contains about 3 nmol phosphate residues, provided the RNA exhibits a statistical distribution of bases. Additionally, 1 µg peptide typically contains about x nmol nitrogen residues, dependent on the molecular weight and the number of basic amino acids. When exemplarily calculated for $(Arg)_9$ (molecular weight 1424 g/mol, 9 nitrogen atoms), 1 µg $(Arg)_9$ contains about 700 pmol $(Arg)_9$ and thus 700× 9=6300 pmol basic amino acids=6.3 nmol nitrogen atoms. For a mass ratio of about 1:1 RNA/$(Arg)_9$ an N/P ratio of about 2 can be calculated. When exemplarily calculated for protamine (molecular weight about 4250 g/mol, 21 nitrogen atoms, when protamine from salmon is used) with a mass ratio of about 2:1 with 2 µg RNA, 6 nmol phosphate are to be calulated for the RNA; 1 µg protamine contains about 235 pmol protamine molecues and thus 235×21=4935 pmol basic nitrogen atoms=4.9 nmol nitrogen atoms. For a mass ratio of about 2:1 RNA/protamine an N/P ratio of about 0.81 can be calculated. For a mass ratio of about 8:1 RNA/protamine an N/P ratio of about 0.2 can be calculated. In the context of the present invention, an N/P-ratio is preferably in the range of about 0.1-10, preferably in a range of about 0.3-4 and most preferably in a range of about 0.5-2 or 0.7-2 regarding the ratio of nucleic acid:peptide in the complex, and most preferably in the range of about 0.7-1.5.

Patent application WO2010/037539, the disclosure of which is incorporated herein by reference, describes an immunostimulatory composition and methods for the preparation of an immunostimulatory composition. Accordingly, in a preferred embodiment of the invention, the composition is obtained in two separate steps in order to obtain both, an efficient immunostimulatory effect and efficient translation of the artificial nucleic acid molecule according to the invention. Therein, a so called "adjuvant component" is prepared by complexing—in a first step—the artificial nucleic acid molecule or vector, preferably an RNA, of the adjuvant component with a cationic or polycationic compound in a specific ratio to form a stable complex. In this context, it is important, that no free cationic or polycationic compound or only a neglibly small amount remains in the adjuvant component after complexing the nucleic acid. Accordingly, the ratio of the nucleic acid and the cationic or polycationic compound in the adjuvant component is typically selected in a range that the nucleic acid is entirely complexed and no free cationic or polycationic compound or only a neclectably small amount remains in the composition.

Preferably the ratio of the adjuvant component, i.e. the ratio of the nucleic acid to the cationic or polycationic compound is selected from a range of about 6:1 (w/w) to about 0,25:1 (w/w), more preferably from about 5:1 (w/w) to about 0,5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

According to a preferred embodiment, the artificial nucleic acid molecule or vector, preferably an RNA molecule, according to the invention is added in a second step to the complexed nucleic acid molecule, preferably an RNA, of the adjuvant component in order to form the (immunostimulatory) composition of the invention. Therein, the artificial acid molecule or vector, preferably an RNA, of the invention is added as free nucleic acid, i.e. nucleic acid, which is not complexed by other compounds. Prior to addition, the free artificial nucleic acid molecule or vector is not complexed and will preferably not undergo any detectable or significant complexation reaction upon the addition of the adjuvant component.

Suitable adjuvants may furthermore be selected from nucleic acids having the formula (II): $G_lX_mG_n$, wherein: G is guanosine, uracil or an analogue of guanosine or uracil; X is guanosine, uracil, adenosine, thymidine, cytosine or an analogue of the above-mentioned nucleotides; l is an integer from 1 to 40, wherein when l=1 G is guanosine or an analogue thereof, when l>1 at least 50% of the nucleotides are guanosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 G is guanosine or an analogue thereof, when n>1 at least 50% of the nucleotides are guanosine or an analogue thereof.

Other suitable adjuvants may furthermore be selected from nucleic acids having the formula (III): $C_lX_mC_n$, wherein: C is cytosine, uracil or an analogue of cytosine or uracil; X is guanosine, uracil, adenosine, thymidine, cytosine or an analogue of the above-mentioned nucleotides; l is an integer from 1 to 40, wherein when l=1 C is cytosine or an analogue thereof, when l>1 at least 50% of the nucleotides are cytosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 C is cytosine or an analogue thereof, when n>1 at least 50% of the nucleotides are cytosine or an analogue thereof.

The pharmaceutical composition according to the present invention preferably comprises a "safe and effective amount" of the components of the pharmaceutical composition, particularly of the inventive artificial nucleic acid molecule, the vector and/or the cells as defined herein. As used herein, a "safe and effective amount" means an amount sufficient to significantly induce a positive modification of a disease or disorder as defined herein. At the same time, however, a "safe and effective amount" preferably avoids serious side-effects and permits a sensible relationship between advantage and risk. The determination of these limits typically lies within the scope of sensible medical judgment.

In a further aspect, the present invention provides the artificial nucleic acid molecule according to the present invention, the vector according to the present invention, the cell according to the present invention, or the pharmaceutical composition according to the present invention for use as a medicament, for example, as vaccine (in genetic vaccination) or in gene therapy.

The artificial nucleic acid molecule according to the present invention, the vector according to the present invention, the cell according to the present invention, or the pharmaceutical composition according to the present invention are particularly suitable for any medical application, which makes use of the therapeutic action or effect of peptides, polypeptides or proteins, or where supplementation of a particular peptide or protein is needed. Thus, the present invention provides the artificial nucleic acid molecule according to the present invention, the vector according to the present invention, the cell according to the present invention, or the pharmaceutical composition according to the present invention for use in the treatment or prevention of diseases or disorders amenable to treatment by the therapeutic action or effect of peptides, polypeptides or proteins or amenable to treatment by supplementation of a particular peptide, polypeptide or protein. For example, the artificial nucleic acid molecule according to the present invention, the vector according to the present invention, the cell according to the present invention, or the pharmaceutical composition according to the present invention may be used for the treatment or prevention of genetic diseases, autoimmune diseases, cancerous or tumour-related diseases, infectious diseases, chronic diseases or the like, e.g., by genetic vaccination or gene therapy.

In particular, such therapeutic treatments, which benefit from a stable and prolonged presence of therapeutic peptides, polypeptides or proteins in a subject to be treated, are especially suitable as medical application in the context of the present invention, since the inventive artificial nucleic acid molecule provides for a stable, increased and/or prolonged expression of the peptide or protein encoded by the inventive artificial nucleic acid molecule or vector. Thus, a particularly suitable medical application for the artificial nucleic acid molecule according to the present invention, the vector according to the present invention, the cell according to the present invention, or the pharmaceutical composition according to the present invention is vaccination. Thus, the present invention provides the artificial nucleic acid molecule according to the present invention, the vector according to the present invention, the cell according to the present invention, or the pharmaceutical composition according to the present invention for vaccination of a subject, preferably a mammalian subject, more preferably a human subject. Preferred vaccination treatments are vaccination against infectious diseases, such as bacterial, protozoal or viral infections, and anti-tumour-vaccination. Such vaccination treatments may be prophylactic or therapeutic.

Depending on the disease to be treated or prevented, the ORF may be selected. For example, the open reading frame may encode a protein that has to be supplied to a patient suffering from total lack or at least partial loss of function of a protein, such as a patient suffering from a genetic disease. Additionally the open reading frame may be chosen from an ORF encoding a peptide or protein, which beneficially influences a disease or the condition of a subject. Furthermore, the open reading frame may encode a peptide or protein, which results in the downregulation of a pathological overproduction of a natural peptide or protein or elimination of cells expressing pathologically a protein or peptide. Such lack, loss of function or overproduction may, e.g., occur in the context of tumour and neoplasia, autoimmune diseases, allergies, infections, chronic diseases or the like. Furthermore, the open reading frame may encode an antigen or immunogen, e.g. an epitope of a pathogen or a tumour antigen. Thus, in preferred embodiments, the artificial nucleic acid molecule or the vector according to the present invention comprises an ORF encoding an amino acid sequence comprising or consisting of an antigen or immunogen, e.g. an epitope of a pathogen or a tumour-associated antigen, and a 3'-UTR as described above.

In the context of medical applications, particularly in the context of vaccination, it is preferred that the artificial nucleic acid molecule according to the present invention is RNA, preferably mRNA, since DNA harbours the risk of eliciting an anti-DNA immune response and tends to insert into genomic DNA. However, in some embodiments, for example, if a viral delivery vehicle, such as an adenoviral delivery vehicle is used for delivery of the artificial nucleic acid molecule or the vector according to the present invention, e.g., in the context of gene therapeutic treatments, it may be desirable that the artificial nucleic acid molecule or the vector is a DNA molecule.

The artificial nucleic acid molecule according to the present invention, the vector according to the present invention, the cell according to the present invention, or the pharmaceutical composition according to the present invention are administered orally, parenterally, by inhalation spray, topically, rectally, nasally, buccally, vaginally, via an implanted reservoir or via jet injection. The term parenteral as used herein includes subcutaneous, intravenous, intramuscular, intra-articular, intrasynovial, intrasternal, intrathecal, intrahepatic, intralesional, intracranial, transdermal, intradermal, intrapulmonal, intraperitoneal, intracardial, intraarterial, and sublingual injection or infusion techniques. In a preferred embodiment, the artificial nucleic acid molecule according to the present invention, the vector according to the present invention, the cell according to the present invention, or the pharmaceutical composition according to the present invention is administered intramuscularly, preferably via conventional needle injection or via needle-free injection (e.g. jet injection).

Preferably, the artificial nucleic acid molecule according to the present invention, the vector according to the present invention, the cell according to the present invention, or the pharmaceutical composition according to the present invention is administered parenterally, e.g. by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, sublingual injection or via infusion techniques. Particularly preferred is intramuscular injection. Sterile injectable forms of the inventive pharmaceutical composition may be aqueous or oleaginous suspension. These suspensions may be formulated according to techniques known in the art using suitable dispersing or wetting agents and suspending agents. Preferably, the solutions or suspensions are administered via conventional needle injection or via needle-free injection (e.g. jet injection).

The artificial nucleic acid molecule according to the present invention, the vector according to the present invention, the cell according to the present invention, or the pharmaceutical composition according to the present invention may also be administered orally in any orally acceptable dosage form including, but not limited to, capsules, tablets, aqueous suspensions or solutions.

The artificial nucleic acid molecule according to the present invention, the vector according to the present invention, the cell according to the present invention, or the pharmaceutical composition according to the present invention may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the artificial nucleic acid molecule according to the present invention, the vector according to the present invention, the cell according to the present invention, or the pharmaceutical composition according to the present invention may be formulated in a suitable ointment suspended or dissolved in one or more carriers.

In one embodiment, the use as a medicament comprises the step of transfection of mammalian cells, preferably in vitro or ex vivo transfection of mammalian cells, more preferably in vitro transfection of isolated cells of a subject to be treated by the medicament. If the use comprises the in vitro transfection of isolated cells, the use as a medicament may further comprise the readministration of the transfected cells to the patient. The use of the inventive artificial nucleic acid molecules or the vector as a medicament may further comprise the step of selection of successfully transfected isolated cells. Thus, it may be beneficial if the vector further comprises a selection marker. Also, the use as a medicament may comprise in vitro transfection of isolated cells and purification of an expression-product, i.e. the encoded peptide or protein from these cells. This purified peptide or protein may subsequently be administered to a subject in need thereof.

The present invention also provides a method for treating or preventing a disease or disorder as described above comprising administering the artificial nucleic acid molecule according to the present invention, the vector according to the present invention, the cell according to the present invention, or the pharmaceutical composition according to the present invention to a subject in need thereof. Therein, the artificial nucleic acid molecule, the vector, the cell or the pharmaceutical composition are administered by any route as described herein. Particularly preferred, in this context, is the intramuscular administration of the artificial nucleic acid molecule, the vector, the cell or the pharmaceutical composition.

According to a preferred embodiment, the inventive artificial nucleic acid molecule, the inventive vector, the inventive cell, the inventive vaccine or the inventive pharmaceutical composition is administered to subject intramuscularly. Advantageously, intramuscular administration of the inventive nucleic acid molecule, vector, vaccine or composition results in an increased expression of the peptide or protein encoded by the at least one open reading frame of the artificial nucleic acid molecule as defined herein. In a particularly preferred embodiment, the expression of the artificial nucleic acid molecule as defined herein, preferably of the artificial nucleic acid molecule comprising a 3'-UTR comprising at least one, more preferably at least two, poly(A) sequences as defined herein, is enhanced when administered intramuscularly. Most preferably, the intramuscular administration of the inventive artificial nucleic acid molecule, preferably of the inventive artificial nucleic acid molecule comprising at least two poly(A) sequences, results in increased expression and in an improved immune response against an antigen, preferably a pathogenic antigen as defined herein, more preferably an antigen associated with an infectious disease.

Furthermore, the present invention provides a method for treating or preventing a disease or disorder comprising transfection of a cell with an artificial nucleic acid molecule according to the present invention or with the vector according to the present invention. Said transfection may be performed in vitro, ex vivo or in vivo. In a preferred embodiment, transfection of a cell is performed in vitro and the transfected cell is administered to a subject in need thereof, preferably to a human patient. Preferably, the cell, which is to be transfected in vitro, is an isolated cell of the subject, preferably of the human patient. Thus, the present invention provides a method of treatment comprising the steps of isolating a cell from a subject, preferably from a human patient, transfecting the isolated cell with the artificial nucleic acid according to the present invention or the vector according to the present invention, and administering the transfected cell to the subject, preferably the human patient.

The method of treating or preventing a disorder according to the present invention is preferably a vaccination method or a gene therapy method as described above.

As described above, the inventive 3'-UTR is capable of increasing the protein production from an artificial nucleic acid molecule. Thus, in a further aspect, the present invention relates to a method for increasing protein production from an artificial nucleic acid molecule, preferably from an mRNA molecule or a vector, the method comprising the step of associating the nucleic acid molecule, preferably the mRNA molecule or the vector, with a 3'-untranslated region (3'-UTR), wherein the 3'-UTR comprises at least one poly (A) sequence, wherein the at least one poly(A) sequence comprises at least 70 adenosine residues, or a polyadenylation signal. In a preferred embodiment, the method comprises associating the nucleic acid molecule, preferably the mRNA or the vector, with a 3'-UTR comprising at least two poly(A) sequences as described herein.

The term "associating the artificial nucleic acid molecule or the vector with a 3'-UTR" in the context of the present invention preferably means functionally associating or functionally combining the artificial nucleic acid molecule or the vector with the 3'-UTR. This means that the artificial nucleic acid molecule or the vector and the 3'-UTR, preferably the 3'-UTR as described above, are associated or coupled such that the function of the 3'-UTR, e.g., the protein production increasing function, is exerted. Typically, this means that the 3'-UTR is integrated into the artificial nucleic acid molecule or the vector, preferably the mRNA molecule, 3' to an open reading frame, preferably immediately 3' to an open reading frame, preferably between the open reading frame and a polyadenylation signal. Preferably, the 3'-UTR is integrated into the artificial nucleic acid molecule or the vector, preferably the mRNA, as 3'-UTR, i.e. such that the 3'-UTR is the 3'-UTR of the artificial nucleic acid molecule or the vector, preferably the mRNA, i.e., such that it extends from the 3'-side of the open reading frame to the 5'-terminus of the molecule or to the 5'-side of a poly(A) sequence or a polyadenylation signal, optionally connected via a short linker, such as a sequence comprising or consisting of one or more restriction sites. Thus, preferably, the term "associating the artificial nucleic acid molecule or the vector with a 3'-UTR" means functionally associating the 3'-UTR with an open reading frame located within the artificial nucleic acid molecule or the vector, preferably within the mRNA molecule. The 3'-UTR and the ORF are as described above for the artificial nucleic acid molecule according to the present invention, for example, preferably the ORF and the 3'-UTR are heterologous, e.g. derived from different genes, as described above.

In a preferred embodiment of the inventive method for increasing protein production from an artificial nucleic acid molecule, preferably from an mRNA molecule or a vector, the at least one poly(A) sequence is produced by a chemical or enzymatic polyadenylation reaction. Preferably, a bacterial enzyme, such as *E. coli* poly(A) polymerase, is employed therein. In a preferred embodiment, the length of the at least one poly(A) sequence is—amongst other parameters—regulated by the duration of the polyadenylation reaction, i.e. longer incubation of a nucleic acid with a suitable enzyme typically leads to a longer poly(A) sequence. Preferably, the nucleic acid molecule is incubated with a suitable enzyme for at least 5, 10, 15, 20, 25, 30, 35, 40, 45, 50, 55, 60, 65, 70, 75, 80, 85 or 90 minutes, preferably at a temperature suitable for the respective enzyme, e.g. 37° C. More preferably, the polyadenylation reaction lasts from about 10 to about 120 minutes, preferably from about 15, 20, 25 or 30 to about 90 minutes, more preferably from about 30 to about 60 minutes. In order to obtain a population of nucleic acid molecules, which share approximately the same degree of polyadenylation, i.e. which have approximately the same number of adenylates attached to their 3'-ends, the skilled person can choose from standard separation techniques (e.g. based on molecular weight or charge), such as chromatographic methods, that are well-known in the art and that are typically employed after polyadenylation in order to separate or purify the reaction products. A population of artificial nucleic acid molecules is preferably used according to the invention, which is more or less homogenous with respect to the length of the 3'-terminal poly(A) sequence. Preferably, a population of artificial nucleic acid molecules is used, wherein at least 80%, more preferably at least 85%, 90%, 95% or 98% of the molecules are characterized by the same length of the 3'-terminal poly(A) sequence. In this context, the same length' refers to a situation, where the number of adenylates in the 3'-terminal poly(A) sequence varies from a given value (such as 160 adenylates, 380 adenylates, 430 adenylates, 1000 adenylates, etc.) by not more than 10%, more preferably not more than 9%, 8%, 7%, 6% 5%, 4%, 3%, 2% or not more than 1%.

In a further aspect, the present invention provides the use of a 3'-UTR for increasing protein production from an artificial nucleic acid molecule as described herein, preferably from an mRNA molecule or a vector, wherein the 3'-UTR comprises at least one poly(A) sequence, wherein the at least one poly(A) sequence comprises at least 70 adenosine residues, or a polyadenylation signal. In a preferred embodiment of the use according to the invention, a 3'-UTR comprising at least two poly(A) sequences, preferably as described herein, is used for increasing protein production from a nucleic acid molecule, preferably from an artificial nucleic acid molecule as described herein.

The compounds and ingredients of the inventive pharmaceutical composition may also be manufactured and traded separately of each other. Thus, the invention relates further to a kit or kit of parts comprising an artificial nucleic acid molecule according to the invention, a vector according to the invention, a cell according to the invention, and/or a pharmaceutical composition according to the invention. Preferably, such kit or kits of parts may, additionally, comprise instructions for use, cells for transfection, an adjuvant, a means for administration of the pharmaceutical composition, a pharmaceutically acceptable carrier and/or a pharmaceutically acceptable solution for dissolution or dilution of the artificial nucleic acid molecule, the vector, the cells or the pharmaceutical composition.

BRIEF DESCRIPTION OF THE FIGURES

The figures shown in the following are merely illustrative and shall describe the present invention in a further way. These figures shall not be construed to limit the present invention thereto.

FIG. 1: DNA sequence (SEQ ID NO: 13) encoding the mRNA sequence, which has been used in the experiments and which comprises the sequences encoding the following elements:

rpl32-PpLuc(GC)-albumin7-A64-C30-histone stem-loop.

Within the DNA sequence, the sequence elements corresponding to the following elements in the mRNA are highlighted: PpLuc(GC) (ORF) in italics, rpl32 (5'-UTR) underlined and albumin7 (3'-UTR) underlined.

FIG. 2: Polyadenylation of the mRNA sequence corresponding to SEQ ID NO: 13:

A. Ca. 160 adenylates were added to one lot of mRNA (Lot 1). Ca. 380 adenylates were added to a different lot of mRNA (Lot 2). mRNA corresponding to SEQ ID NO: 13 was loaded onto the left lane, the respective adenylated mRNA was loaded onto the right line. A molecular size marker was loaded on the outermost lanes for size comparison (the numbers in FIG. 2A indicate the number of nucleotides comprised in the marker molecules; the same marker was used in FIG. 2B and FIG. 2C). B. Ca. 430 adenylates were added to the mRNA corresponding to SEQ ID NO: 13. C. Ca. 1000 adenylates were added to the mRNA corresponding to SEQ ID NO: 13.

Figure 3:
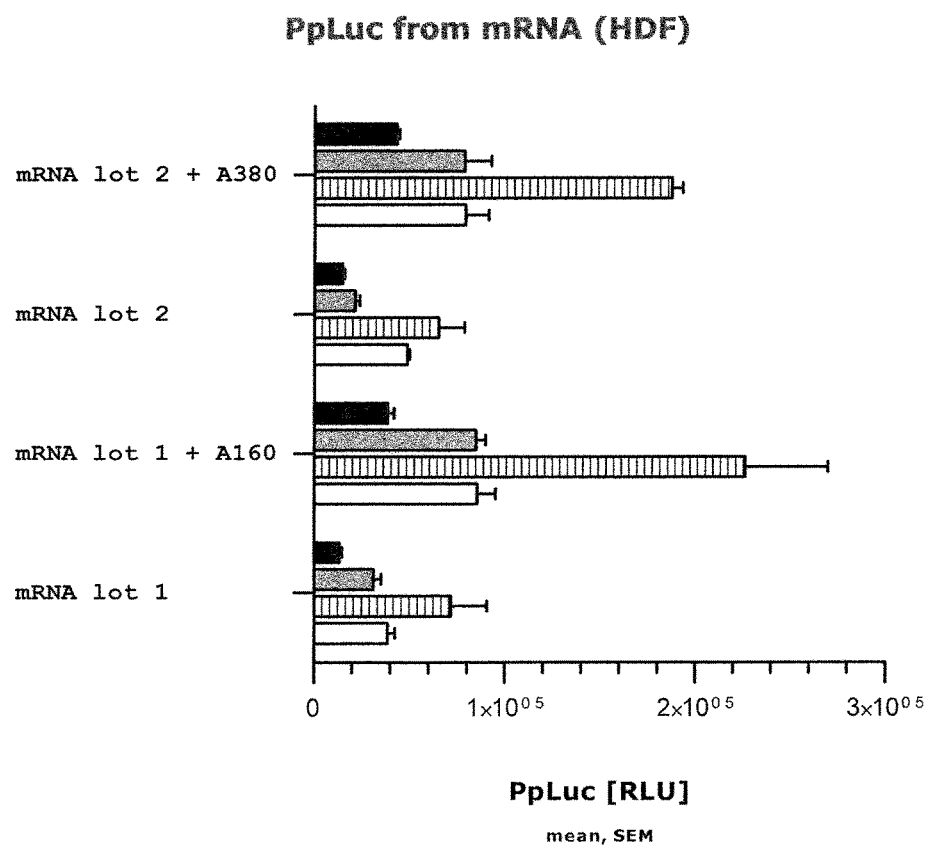

FIG. 3: Protein expression from polyadenylated mRNA in cultured cells:

mRNA corresponding to SEQ ID NO: 13, to which ca. 160 (mRNA lot 1) or ca. 380 (mRNA lot 2) adenylates have been added by polyadenylation, was transfected into human dermal fibroblasts (HDF) and luciferase levels were measured at the indicated time points. FIG. 3 shows the results as mean RLU (relative light units)+/−SEM (standard error) for triplicate transfections.

Figure 4:
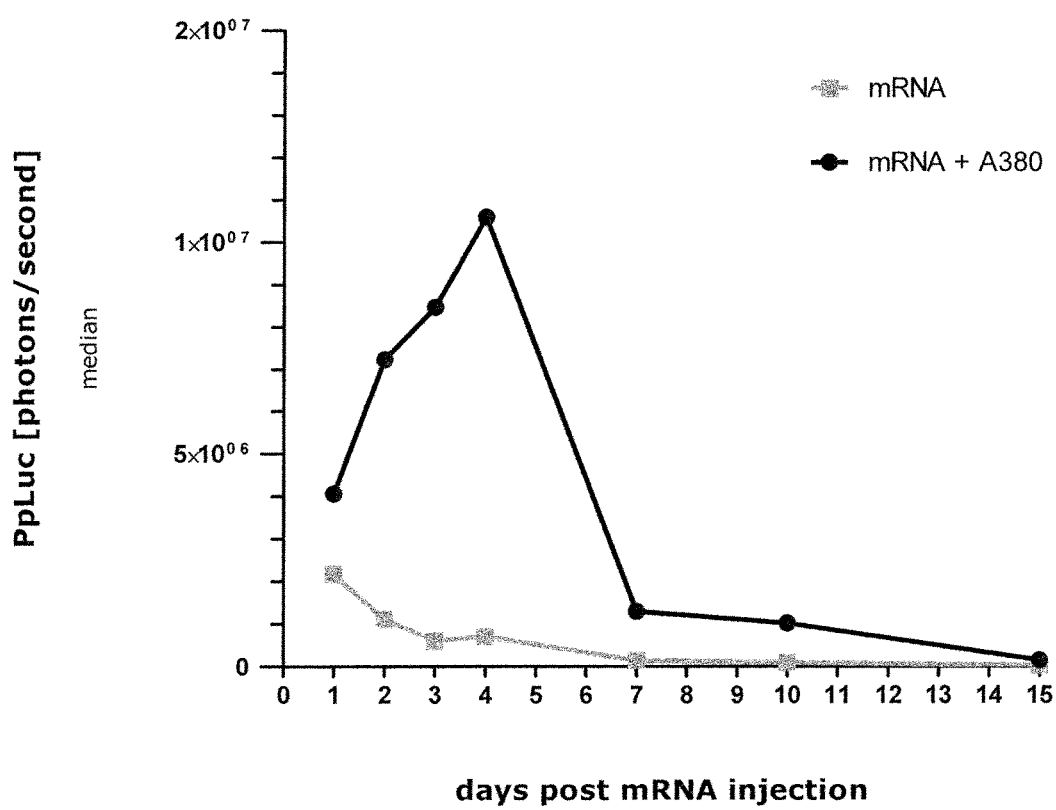

FIG. 4: Protein expression from polyadenylated mRNA after intramuscular injection into mice:

2 µg of mRNA corresponding to SEQ ID NO: 13, to which ca. 380 adenylates have been added by polyadenylation, were intramuscularly injected into mice. FIG. 4 shows the results as the median of up to 10 replicates.

Figure 5:
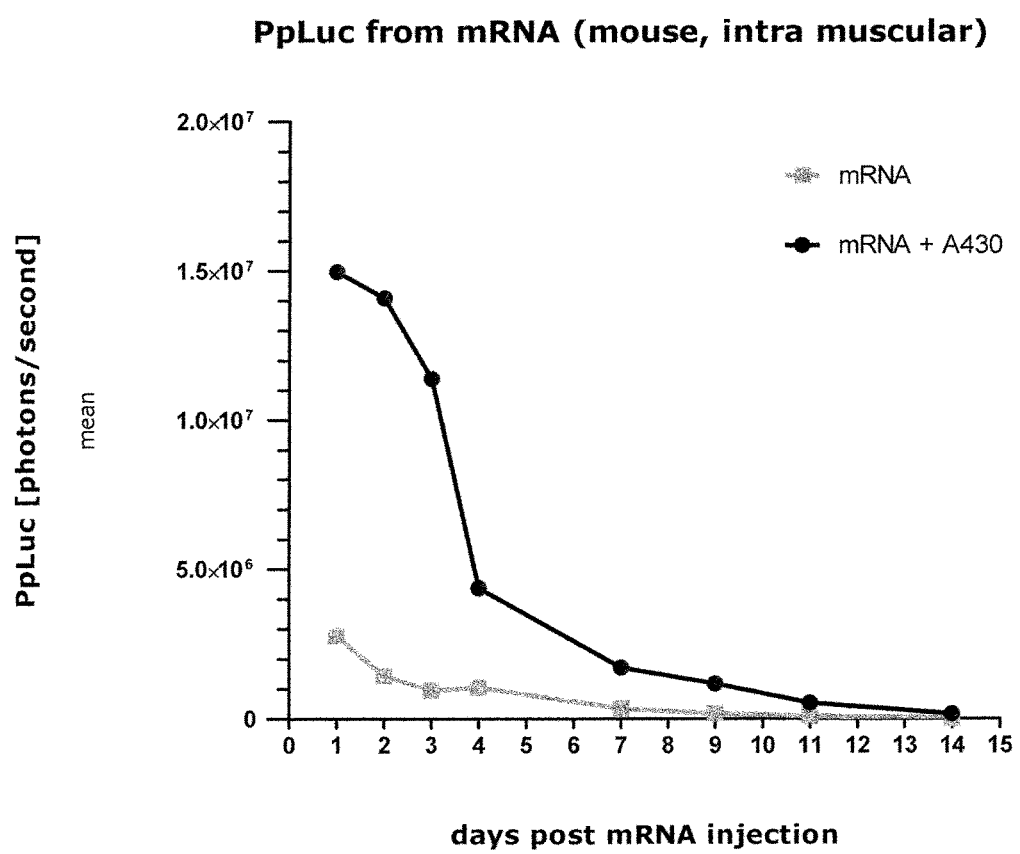

FIG. 5: Protein expression from polyadenylated mRNA after intramuscular injection into mice:

10 µg of mRNA corresponding to SEQ ID NO: 13, to which ca. 430 adenylates have been added by polyadenylation, were intramuscularly injected into mice. FIG. 5 shows the results as the median of up to 10 replicates.

Figure 6:
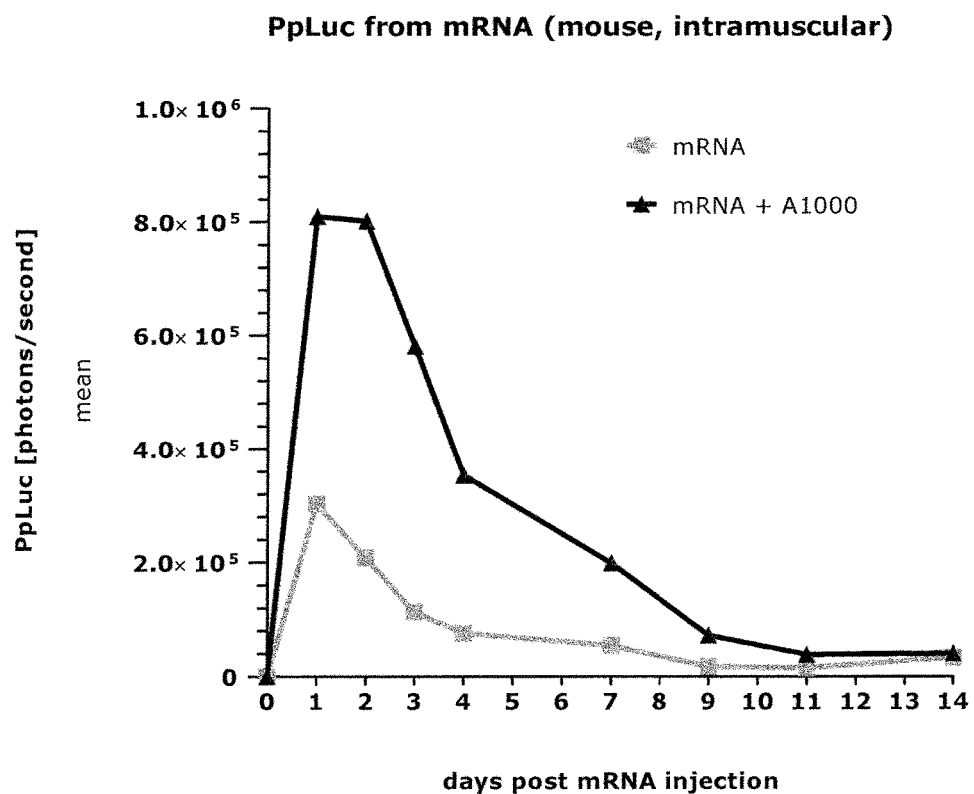

FIG. 6: Protein expression from polyadenylated mRNA after intramuscular injection into mice:

1 µg of mRNA corresponding to SEQ ID NO: 13, to which ca. 1000 adenylates have been added by polyadenylation, was intramuscularly injected into mice. FIG. 6 shows the results as the median of up to 10 replicates.

Figure 7:
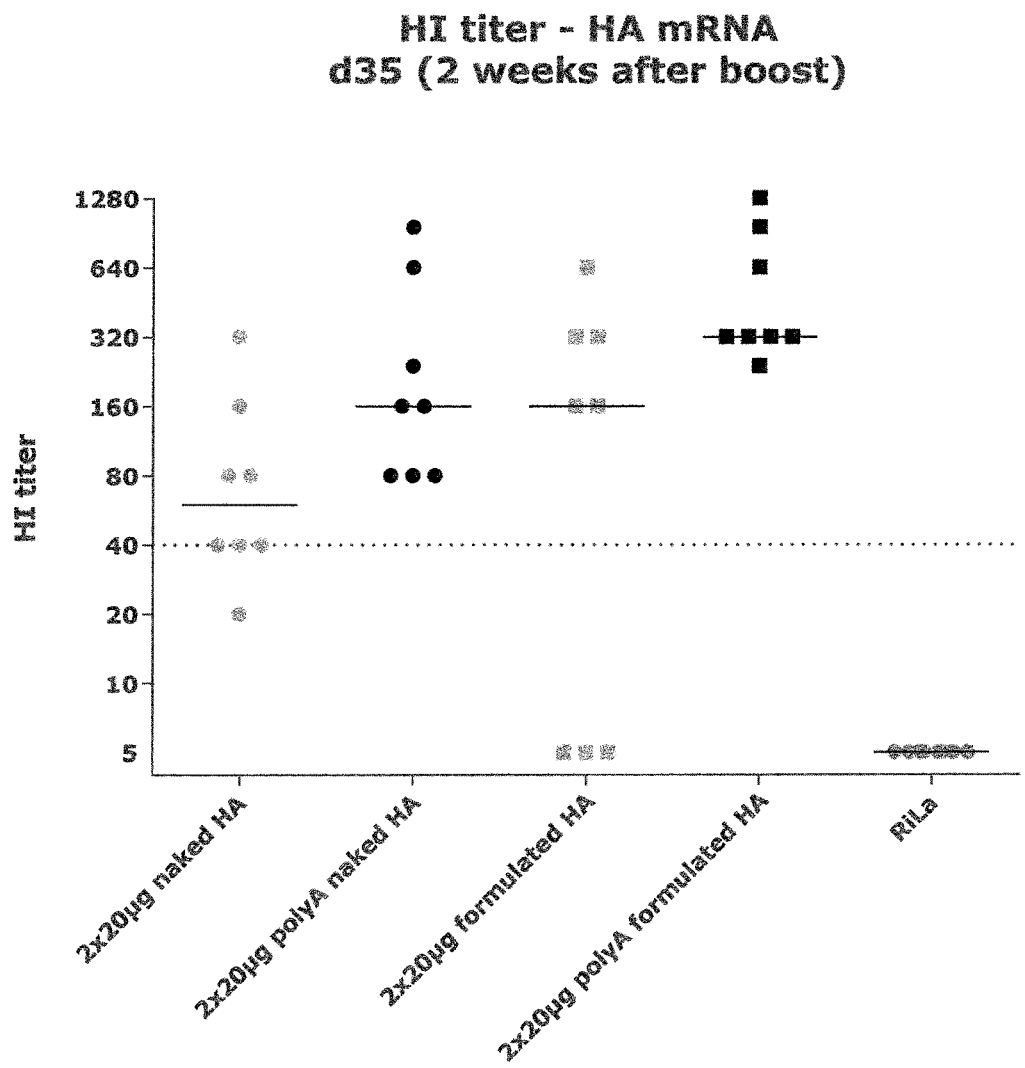

FIG. 7: Induction of HA neutralizing antibodies by polyadenylated mRNA after intramuscular injection into mice:

FIG. 8: DNA sequence (SEQ ID NO: 14) encoding the mRNA sequence, which has been used in the experiments and which comprises the sequences encoding the following elements:

32L4-H1N1(Netherlands2009)-HA(GC)-albumin7-A64-N5-C30-histoneSL

Figure 9:
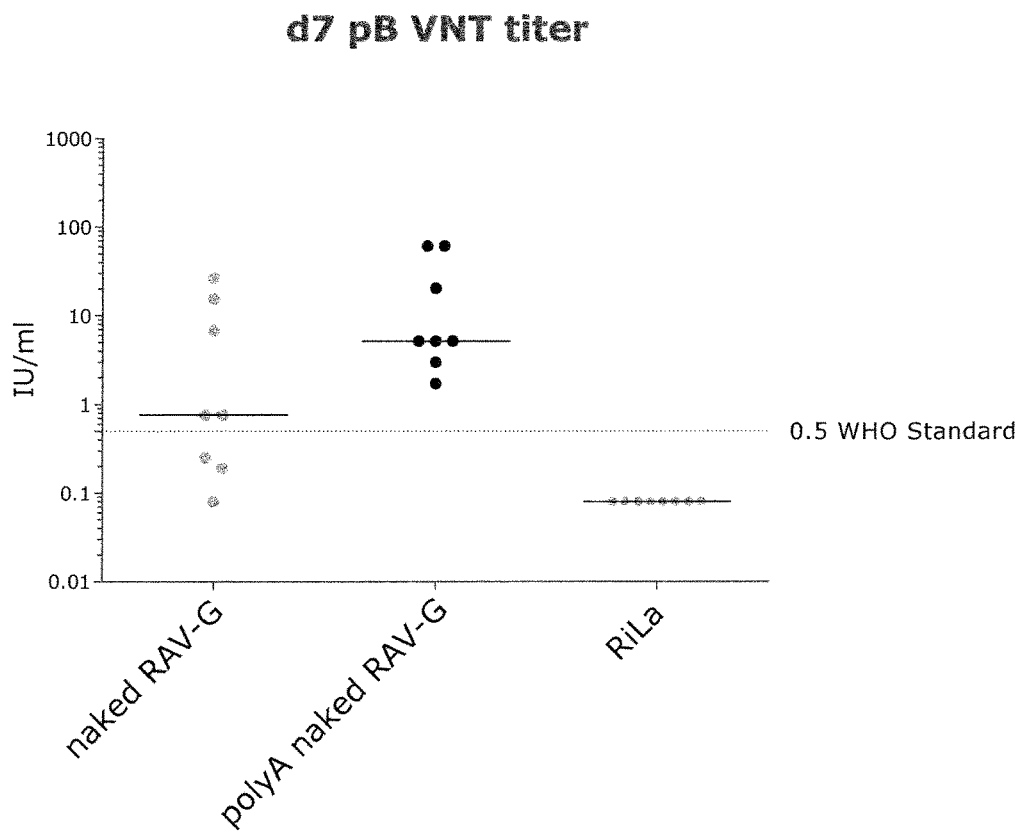

FIG. 9: Induction of virus neutralizing titers by polyadenylated mRNA after intramuscular injection into mice.

FIG. 10: DNA sequence (SEQ ID NO: 15) encoding the mRNA sequence, which has been used in the experiments and which comprises the sequences encoding the following elements:

32L4-RAVG(GC)-albumin7-A64-N5-C30-histoneSL

EXAMPLES

The Examples shown in the following are merely illustrative and shall describe the present invention in a further way. These Examples shall not be construed to limit the present invention thereto.

1. Preparation of DNA-Templates

A vector for in vitro transcription was constructed containing a T7 promoter and a GC-enriched sequence encoding *Photinus pyralis* luciferase (PpLuc(GC)). The 5' untranslated region (5'-UTR) of ribosomal protein Large 32 was inserted 5' of PpLuc(GC). A 3'-UTR derived from human albumin (albumin7) was inserted 3' of PpLuc(GC). Furthermore, an A64 poly(A) sequence, followed by C30 and a histone stem-loop sequence, was inserted 3' of albumin7. The histone stem-loop sequence was followed by a restriction site used for linearization of the vector prior to in vitro transcription. mRNA obtained from this vector accordingly by in vitro transcription is designated as "rpl32-PpLuc(GC)-albumin7-A64-C30-histoneSL".

In summary, a vector was generated that comprises the sequence, which encodes the mRNA, which was used in further experiments. The DNA sequence (SEQ ID NO: 13) encoding said mRNA is shown in FIG. 1. The mRNA corresponding to said DNA sequence is characterized by the following elements:

rpl32-PpLuc(GC)-albumin7-A64-C30-histoneSL

Therein, the following abbreviations are used:

PpLuc (GC): GC-enriched mRNA sequence encoding Photinus pyralis luciferase rpl32: 5'-UTR of human ribosomal protein Large 32 lacking the 5' terminal oligopyrimidine tract albumin7: 3'-UTR of human albumin with three single point mutations introduced to remove a T7 termination signal as well as a HindIII and a XbaI restriction site A64: poly(A)-sequence with 64 adenylates C30: poly(C)-sequence with 30 cytidylates histoneSL: histone stem-loop sequence according to SEQ ID NO: 11.

Further constructs used in the experiments:

32L4-H1N1(Netherlands2009)-HA(GC)-albumin7-A64-N5-C30-histoneSL (SEQ ID NO: 14)

32L4-RAV-G(GC)-albumin7-A64-N5-C30-histoneSL (SEQ ID NO: 15)

The templates were prepared as described for rpl32-PpLuc(GC)-albumin7-A64-C30-histoneSL.

2. In Vitro Transcription

The DNA template prepared in Example 1 was linearized and transcribed in vitro using T7 polymerase. The DNA template was then digested by DNase treatment. mRNA transcripts contained a 5'-cap structure obtained by adding an excess of N7-methyl-guanosine-5'-triphosphate-5'-guanosine to the transcription reaction. mRNA thus obtained was purified and resuspended in water.

3. Enzymatic Adenylation

RNA was reacted with *E. coli* poly(A) polymerase (Cellscript) using 1 mM ATP at 37° C. for 30 or 60 min. Immediately afterwards, RNA was purified using a spin column (RNeasy mini column, Quiagen). RNA was run on a gel to assess RNA extension.

For vaccination experiments the mRNA was optionally complexed with protamine. mRNA complexation consisted of a mixture of 50% naked mRNA and 50% mRNA complexed with protamine at a weight ratio of 2:1. First, mRNA was complexed with protamine by addition of protamine-Ringer's lactate solution to mRNA. After incubation for 10 minutes, when the complexes were stably generated, naked mRNA was added, and the final concentration of the vaccine was adjusted with Ringer's lactate solution. The obtained formulated mRNA vaccine was used for in vivo experiments.

4. Protein Expression by mRNA Lipofection

Human dermal fibroblasts (HDF) were seeded in 96-well plates three days before transfection at a density of $10^4$ cells per well. Immediately before lipofection, cells were washed in Opti-MEM. Cells were lipofected with 25 ng of PpLuc-encoding mRNA per well complexed with Lipofectamine2000. mRNA encoding Renilla reniformis luciferase (RrLuc) was transfected together with PpLuc mRNA to control for transfection efficiency (2.5 ng of RrLuc mRNA per well). 90 minutes after initiation of the transfection, Opti-MEM was exchanged for medium. 6, 24, 48, and 72 hours after transfection, medium was aspirated and cells were lysed in 100 µl of lysis buffer (Passive Lysis Buffer, Promega). Lysates were stored at −80° C. until luciferase activity was measured.

5. Luminescence Measurement in Cell Lysate

Luciferase activity was measured as relative light units (RLU) in a Hidex Chameleon plate reader. PpLuc activity was measured at 2 seconds measuring time using 20 µl of lysate and 50 µl of luciferin buffer (Beetle-Juice, PJK GmbH). RrLuc activity was measured at 2 seconds measuring time using 20 µl of lysate and 50 µl of coelenterazin buffer (Renilla-Juice, PJK GmbH).

6. Protein Expression by Intramuscular mRNA Injection

Mice were anaesthetized by intraperitoneal injection of a Ketavet and Rompun mixture. After shaving the lower leg of the animal, 2 µg of PpLuc-encoding mRNA in 20 µl of Ringer's lactate (80%) were injected intramuscularly (M. tibialis or M. gastrocnemius).

7. In Vivo Luminescence Imaging

Mice were anaesthetized by intraperitoneal injection of a Ketavet and Rompun mixture. 150 µl of Luciferin solution (20 g/l) were injected intraperitoneally. 10 minutes after Luciferin injection, luminescence was recorded on an IVIS Lumina II Imaging System.

Results 8.1 Additional Polyadenylation of the Artificial mRNA Increases Protein Expression from the Artificial mRNA In Vitro To investigate the effect of additional polyadenylation of the artificial mRNA on protein expression from the mRNA, the artificial mRNA was synthesized by in vitro transcription (rpl32-PpLuc(GC)-albumin7-A64-C30-histoneSL). Part of one lot of mRNA was enzymatically adenylated to add a poly(A) tail of ca. 160 adenylates (Lot 1). Part of a different lot of mRNA was enzymatically adenylated to add a poly(A) tail of ca. 380 adenylates (Lot 2) (see FIG. 2).

Luciferase-encoding mRNAs were transfected into human dermal fibroblasts (HDF) in triplicate. Luciferase levels were measured at 6, 24, 48, and 72 hours after transfection. From these data, total protein expressed from 0 to 72 hours was calculated as the area under the curve (AUC) (see following Table 1 and FIG. 3).

TABLE 1

Luciferase activity measured in human dermal fibroblasts (HDF)

| Poly(A) tail | RLU at 6 hours | RLU at 24 hours | RLU at 48 hours | RLU at 72 hours | AUC |
|---|---|---|---|---|---|
| Lot 1 incl. A64 | 37252 | 59085 | 29825 | 14612 | 2579000 |
| Lot 1 incl. A64 plus ca. A160 (A224) | 81043 | 246102 | 89506 | 41308 | 8784000 |
| Lot 2 incl. A64 | 47959 | 61053 | 23001 | 14053 | 2578000 |
| Lot 2 incl. A64 plus ca. A380 (A444) | 69780 | 188560 | 69269 | 44478 | 6993000 |

Total Luciferase expression was identical from both mRNA lots containing an in vitro transcribed A64 sequence. The addition of ca. 160 adenylates to the 3' end of the mRNA (resulting in a 3'-UTR comprising ca. 224 adenylates that are comprised in a poly(A) sequence) increased luciferase expression by factor 3.4. Addition of ca. 380 adenylates to the 3' end of the mRNA (resulting in a 3'-UTR comprising ca. 444 adenyates that are comprised in a poly(A) sequence) increased luciferase expression only to a similar extent, by factor 2.7.

Thus, addition of (further) adenylates to the 3' end of the mRNA markedly increases the in vitro expression of the protein encoded by the mRNA. In particular, a 3'-UTR comprising more than 64 adenylates that are comprised in a poly(A) sequence markedly increases protein expression in vitro.

8.2 Additional Polyadenylation of the Artificial mRNA Strongly Increases Protein Expression from the Artificial mRNA after Intramuscular Injection To investigate the effect of additional polyadenylation of the artificial mRNA on protein expression from the intramuscularly injected mRNA, the artificial mRNA was synthesized by in vitro transcription (rpl32-PpLuc(GC)-albumin7-A64-C30-histoneSL). Part of this mRNA was enzymatically adenylated to add a poly(A) tail of ca. 380 adenylates.

2 µg of luciferase-encoding mRNAs were injected intramuscularly (M. tibialis or M. gastrocnemius) in BALB/c mice (10 replicates per group). In vivo luminescence was recorded the following days (see FIG. 4). From these data, total protein expressed from 0 to 15 days was calculated as the area under the curve. Luciferase was clearly expressed from intramuscularly injected mRNA containing an A64 sequence. Strikingly, however, additional polyadenylation of the artificial mRNA with 380 adenylates increased luciferase expression very strongly, raising total luciferase expressed eightfold. The magnitude of the rise in expression due to the (additional) poly(A) tail was unanticipated considering the much smaller effect observed in cultured cells. Thus, the addition of (further) adenylates comprised in a poly(A) sequence increases protein expression from intramuscularly injected mRNA very strongly to an unanticipated extent. In parallel, the effect of the additional polyadenylation of the artificial mRNA with about 430 adenylates (see FIG. 5) and about 1000 adenylates (see FIG. 6), respectively, was tested. While the both of the mRNAs that were polyadenylated with about 430 adenylates and about 1000 adenylates, respectively, led to increased protein expression as compared to non-polyadenlyated mRNA, no further increase was observed with respect to the artificial mRNA polyadenylated with 380 adenylates.

9. Vaccination with mRNA Encoding HA:

Balb/c mice were vaccinated 2 times (d0 and d21) into both M. tibialis. 8 mice were vaccinated with 40 μg R2564 (naked HA mRNA), 8 animals were vaccinated with 40 μg polyadenylated R2564 (SEQ ID NO: 14; naked, polyadenylated HA), 8 animals were vaccinated with 40 μg R2630 (formulated HA mRNA) and 8 animals were vaccinated with 40 μg first polyadenylated and then formulated R2564. 8 mice injected with RiLa served as controls. Blood was collected on d35.

9.1. Hemagglutination Inhibition Assay (HI)

In a 96-well plate, the obtained sera were mixed with HA H1N1 antigen (A/California/07/2009 (H1N1); NIBSC) and red blood cells (4% erythrocytes; Lohmann Tierzucht). In the presence of HA neutralizing antibodies, an inhibition of hemagglutination of erythrocytes can be observed. The lowest level of titered serum that resulted in a visible inhibition of hemagglutination was the assay result.

Results:

The results show that higher HI titers could be reached by polyadenylation of the mRNA. All mice treated with polyadenylated mRNA reached a level over potentially protective virus neutralizing titers (>40).

10. Vaccination with mRNA Encoding RAV G:

Balb/c mice were vaccinated 2 times (d0 and d21) with 20 μg RAV-G mRNA into both *M. tibialis*. 8 animals were vaccinated i.m. with R2506 (SEQ ID NO: 15; naked RAV-G mRNA), 8 animals were vaccinated i.m. with polyadenylated R2506 (naked RNA) and 8 mice were injected with RiLa as controls. Blood was collected 28 days after prime. Serum was analyzed for VNTs.

10.1. Virus Neutralization Test

Detection of the virus neutralizing antibody response (specific B-cell immune response) was carried out by a virus neutralisation assay. The result of that assay is referred to as virus neutralization titer (VNT). According to WHO standards, an antibody titer is considered protective if the respective VNT is at least 0.5 IU/ml. Therefore, blood samples were taken from vaccinated mice on day 28 and sera were prepared. These sera were used in fluorescent antibody virus neutralisation (FAVN) test using the cell culture adapted challenge virus strain (CVS) of rabies virus as recommended by the OIE (World Organisation for Animal Health) and first described in Cliquet F., Aubert M. & Sagne L. (1998); J. Immunol. Methods, 212, 79-87. In brief, heat inactivated sera were tested as quadruplicates in serial two-fold dilutions with respect to their potential to neutralise 100 TCID50 (tissue culture infectious doses 50%) of CVS in 50 μl of volume. Therefore, sera dilutions were incubated with virus for 1 hour at 37° C. (in humid incubator with 5% CO2) and subsequently trypsinized BHK-21 cells were added (4×105 cells/ml; 50 μl per well). Infected cell cultures were incubated for 48 hours in humid incubator at 37° C. and 5% CO2. Infection of cells was analysed after fixation of cells using 80% acetone at room temperature using FITC anti-rabies conjugate. Plates were washed twice using PBS and excess of PBS was removed. Cell cultures were scored as positive or as negative with regard to the presence of rabies virus. Negatively scored cells in sera treated wells represent neutralization of rabies virus. Each FAVN tests included WHO or OIE standard serum (positive reference serum) that served as reference for standardisation of the assay. Neutralization activity of test sera was calculated with reference to the standard serum provided by the WHO and displayed as International Units/ml (IU/m1).

Results

As can be seen in FIG. 9, the polyadenylated RAV-G mRNA induces higher neutralizing antibody titers, well above the WHO standard of 0.5 IU/ml.

The invention claimed is:

1. A method for treating or preventing an infectious disease, the method comprising administering an RNA molecule comprising:
   a) at least one open reading frame (ORF) encoding an antigen from a pathogen associated with the infectious disease; and
   b) a 3'-untranslated region (3'-UTR) comprising at least two poly(A) sequences, wherein at least one of the poly(A) sequences comprises at least 70 adenine nucleotides, wherein the at least two poly(A) sequence elements are separated by a nucleic acid sequence comprising from 10 to 90 nucleotides,
   wherein the RNA molecule is administered intramuscularly.

2. The method of claim 1, wherein the at least two poly(A) sequence elements are separated by a nucleic acid sequence comprising a poly(C) element and/or a histone stem-loop element.

3. The method of claim 1, wherein the pathogen is selected from the group consisting of a bacterial, a viral, a fungal, and a protozoan pathogen.

4. The method of claim 1, wherein at least one of the poly(A) sequences comprises at least 150 adenine nucleotides.

5. The method of claim 1, wherein at least one of the poly(A) sequences is located at the 3' terminus of the RNA molecule.

6. The method of claim 1, wherein the 3'-UTR further comprises at least one 3'-UTR element that is not a poly(A) sequence.

7. The method of claim 1, wherein the RNA molecule further comprises a 5'-cap structure, a poly(C) sequence, a histone stem-loop, and/or an IRES motif.

8. The method of claim 7, wherein the histone stem-loop comprises a sequence according to SEQ ID NO: 11.

9. The method of claim 1, wherein the RNA molecule further comprises a 5'-UTR and/or a promoter containing-sequence.

10. The method of claim 9, wherein the 5'-UTR comprises at least a portion of a 5'-UTR of a 5' Terminal Oligopyrimidine Tract (TOP) gene.

11. The method of claim 1, wherein the open reading frame is at least partially G/C modified, wherein the encoded antigen sequence is not altered.

12. The method of claim 11, wherein the G/C content of the open reading frame is increased compared to a wild type open reading frame, wherein the encoded antigen sequence is not altered.

13. The method of claim 1, wherein the open reading frame is at least partially codon-optimized.

14. The method of claim 13, wherein the RNA molecule comprises at least one nucleotide analogue.

15. The method of claim 14, wherein the at least one nucleotide analogue is a modified form of uridine.

16. The method of claim 15, wherein the modified form of uridine is chemically altered by methylation.

17. The method of claim 16, wherein the modified form of uridine is a naturally occurring variant of uridine.

18. The method of claim 17, wherein the RNA molecule is associated or complexed with a cationic carrier or a polycationic carrier.

19. The method of claim 1, wherein the at least two poly(A) sequence elements are separated by a nucleic acid sequence comprising a poly(C) element and a histone stem-loop element.

20. The method of claim 1, wherein the RNA molecule is associated with or complexed with a cationic or polycationic compound or polymeric carrier.

* * * * *

UNITED STATES PATENT AND TRADEMARK OFFICE
CERTIFICATE OF CORRECTION

PATENT NO. : 11,149,278 B2
APPLICATION NO. : 15/534496
DATED : October 19, 2021
INVENTOR(S) : Andreas Thess, Thomas Schlake and Stefanie Grund It is certified that error appears in the above-identified patent and that said Letters Patent is hereby corrected as shown below:

On the Title Page

Item (56), References Cited - Foreign Patent Documents, delete "WO WO 2016-107877 7/1916" and insert --WO WO 2016-107877 7/2016-- therefor.

Item (56), References Cited - Foreign Patent Documents, delete "WO WO 2016-165825 10/1916" and insert --WO WO 2016-165825 10/2016-- therefor.

Item (56), References Cited - Foreign Patent Documents, delete "WO WO 2016-165831 10/1916" and insert --WO WO 2016-165831 10/2016-- therefor.

Item (56), References Cited - Foreign Patent Documents, delete "WO WO 2016-184576 11/1916" and insert --WO WO 2016-184576 11/2016-- therefor.

Item (56), References Cited - Foreign Patent Documents, delete "WO WO 2016-184822 11/1916" and insert --WO WO 2016-184822 11/2016-- therefor.

Item (56), References Cited - Foreign Patent Documents, delete "WO WO 2016474227 11/1916" and insert --WO WO 2016-474227 11/2016-- therefor.

Item (56), References Cited - Foreign Patent Documents, delete "WO WO 2016474271 11/1916" and insert --WO WO 2016-474271 11/2016-- therefor.

Item (56), References Cited - Foreign Patent Documents, delete "WO WO 2016484575 12/1916" and insert --WO WO 2016-484575 12/2016-- therefor.

Item (56), References Cited - Foreign Patent Documents, delete "WO WO 2016493206 12/1916" and insert --WO WO 2016-493206 12/2016-- therefor.

Signed and Sealed this
Seventh Day of June, 2022

Katherine Kelly Vidal
*Director of the United States Patent and Trademark Office*

CERTIFICATE OF CORRECTION (continued)
U.S. Pat. No. 11,149,278 B2

Item (56), References Cited - Foreign Patent Documents, delete "WO WO 2016-203025 12/1916" and insert --WO WO 2016-203025 12/2016-- therefor.

Item (56), References Cited - Foreign Patent Documents, delete "WO WO 2016493226 12/1916" and insert --WO WO 2016-493226 12/2016-- therefor.

Item (56), References Cited - Foreign Patent Documents, delete "WO WO 2017-001058 1/1917" and insert --WO WO 2017-001058 1/2017-- therefor.

Item (56), References Cited - Foreign Patent Documents, delete "WO WO 2017-009376 1/1917" and insert --WO WO 2017-009376 1/2017-- therefor.

Item (56), References Cited - Foreign Patent Documents, delete "WO WO 2017-021546 2/1917" and insert --WO WO 2017-021546 2/2017-- therefor.

Item (56), References Cited - Foreign Patent Documents, delete "WO WO 2017-0025120 2/1917" and insert --WO WO 2017-0025120 2/2017-- therefor.

Item (56), References Cited - Foreign Patent Documents, delete "WO WO 2017-025447 2/1917" and insert --WO WO 2017-025447 2/2017-- therefor.

Item (56), References Cited - Foreign Patent Documents, delete "WO WO 2017-036580 3/1917" and insert --WO WO 2017-036580 3/2017-- therefor.

Item (56), References Cited - Foreign Patent Documents, delete "WO WO 2013443700 10/2013" and insert --WO WO 2013-443700 10/2013-- therefor.